(12) United States Patent
Ben-Haim et al.

(10) Patent No.: US 10,321,954 B2
(45) Date of Patent: *Jun. 18, 2019

(54) APPLICATOR AND TISSUE INTERFACE MODULE FOR DERMATOLOGICAL DEVICE

(71) Applicant: MIRADRY, INC., Santa Clara, CA (US)

(72) Inventors: Yoav Ben-Haim, San Francisco, CA (US); Peter J. Bentley, San Jose, CA (US); Donghoon Chun, Sunnvyale, CA (US); Daniel E. Francis, Mountain View, CA (US); Jessi E. Johnson, Sunnyvale, CA (US); Kevin Shan, Pasadena, CA (US); Ted Y. Su, Sunnyvale, CA (US); Steven W. Kim, Los Altos, CA (US)

(73) Assignee: MIRADRY, INC., Santa Clara, CA (US)

( * ) Notice: Subject to any disclaimer, the term of this patent is extended or adjusted under 35 U.S.C. 154(b) by 250 days.

This patent is subject to a terminal disclaimer.

(21) Appl. No.: 15/090,273

(22) Filed: Apr. 4, 2016

(65) Prior Publication Data
US 2016/0213426 A1 Jul. 28, 2016

Related U.S. Application Data

(62) Division of application No. 13/563,656, filed on Jul. 31, 2012, now Pat. No. 9,314,301.
(Continued)

(51) Int. Cl.
*A61B 18/18* (2006.01)
*A61N 5/04* (2006.01)
(Continued)

(52) U.S. Cl.
CPC ............ *A61B 18/1815* (2013.01); *A61N 5/04* (2013.01); *A61B 2017/00681* (2013.01);
(Continued)

(58) Field of Classification Search
CPC ...... A61B 18/1815; A61B 2018/00023; A61B 2018/00291; A61B 2018/00452; A61B 2018/00821; A61N 5/04
See application file for complete search history.

(56) References Cited

U.S. PATENT DOCUMENTS

| 2,407,690 A | 9/1946 | Southworth |
| 3,307,553 A | 3/1967 | Liebner |

(Continued)

FOREIGN PATENT DOCUMENTS

| AU | 297299 A | 9/1999 |
| CN | 1688363 A | 10/2005 |

(Continued)

OTHER PUBLICATIONS

Deem et al.; U.S. Appl. No. 15/406,496 entitled "Systems and methods for creating an effect using microwave energy to specified tissue," filed Jan. 13, 2017.

(Continued)

*Primary Examiner* — Daniel W Fowler
(74) *Attorney, Agent, or Firm* — Shay Glenn LLP

(57) ABSTRACT

A tissue interface module has an applicator chamber on a proximal side of the tissue interface module and a tissue acquisition chamber on a distal side of the tissue interface module. The applicator chamber may include: an opening adapted to receive the applicator; an attachment mechanism positioned in the applicator chamber and adapted to attach the tissue interface module to the applicator; a sealing member positioned at a proximal side of the applicator chamber; and a vacuum interface positioned at a proximal (Continued)

side of the applicator chamber and adapted to receive a vacuum inlet positioned on a distal end of the applicator. The invention also includes corresponding methods.

5 Claims, 33 Drawing Sheets

Related U.S. Application Data

(60) Provisional application No. 61/513,834, filed on Aug. 1, 2011, provisional application No. 61/555,410, filed on Nov. 3, 2011, provisional application No. 61/673,697, filed on Jul. 19, 2012, provisional application No. 61/676,833, filed on Jul. 27, 2012.

(51) Int. Cl.
A61B 18/00 (2006.01)
A61B 17/00 (2006.01)

(52) U.S. Cl.
CPC ............... A61B 2018/00023 (2013.01); A61B 2018/00291 (2013.01); A61B 2018/00452 (2013.01); A61B 2018/00821 (2013.01)

(56) References Cited

U.S. PATENT DOCUMENTS

| | | |
|---|---|---|
| 3,527,227 A | 9/1970 | Fritz |
| 3,693,623 A | 9/1972 | Harte et al. |
| 3,845,267 A | 10/1974 | Fitzmayer |
| 4,069,827 A | 1/1978 | Dominy |
| 4,095,602 A | 6/1978 | Leveen |
| 4,108,147 A | 8/1978 | Kantor |
| 4,140,130 A | 2/1979 | Storm, III |
| 4,174,713 A | 11/1979 | Mehl |
| 4,190,053 A | 2/1980 | Sterzer |
| 4,190,056 A | 2/1980 | Tapper et al. |
| 4,197,860 A | 4/1980 | Sterzer |
| 4,228,809 A | 10/1980 | Paglione |
| 4,375,220 A | 3/1983 | Matvias |
| 4,378,806 A | 4/1983 | Cohn |
| 4,388,924 A | 6/1983 | Weissman et al. |
| 4,397,313 A | 8/1983 | Vaguine |
| 4,397,314 A | 8/1983 | Vaguine |
| 4,446,874 A | 5/1984 | Vaguine |
| 4,528,991 A | 7/1985 | Dittmar et al. |
| 4,589,424 A | 5/1986 | Vaguine |
| 4,597,379 A | 7/1986 | Kihn et al. |
| 4,614,191 A | 9/1986 | Perler |
| 4,617,926 A | 10/1986 | Sutton |
| 4,632,128 A | 12/1986 | Paglione et al. |
| 4,641,649 A | 2/1987 | Walinsky et al. |
| 4,669,475 A | 6/1987 | Turner |
| 4,672,980 A | 6/1987 | Turner |
| 4,690,156 A | 9/1987 | Kikuchi et al. |
| 4,702,262 A | 10/1987 | Andersen et al. |
| 4,744,372 A | 5/1988 | Kikuchi et al. |
| 4,747,416 A | 5/1988 | Kikuchi et al. |
| 4,794,930 A | 1/1989 | Machida et al. |
| 4,798,215 A | 1/1989 | Turner |
| 4,800,899 A | 1/1989 | Elliott |
| 4,825,880 A | 5/1989 | Stauffer et al. |
| 4,841,989 A | 6/1989 | Kikuchi et al. |
| 4,841,990 A | 6/1989 | Kikuchi et al. |
| 4,860,752 A | 8/1989 | Turner |
| 4,881,543 A | 11/1989 | Trembly et al. |
| 4,891,483 A | 1/1990 | Kikuchi et al. |
| 4,945,912 A | 8/1990 | Langberg |
| 4,974,587 A | 12/1990 | Turner et al. |
| 5,059,192 A | 10/1991 | Zaias |
| 5,097,846 A | 3/1992 | Larsen |
| 5,101,836 A | 4/1992 | Lee |
| 5,107,832 A | 4/1992 | Guibert et al. |
| 5,143,063 A | 9/1992 | Fellner |
| 5,186,181 A | 2/1993 | Franconi et al. |
| 5,190,518 A | 3/1993 | Takasu |
| 5,198,776 A | 3/1993 | Carr |
| 5,226,907 A | 7/1993 | Tankovich |
| 5,234,004 A | 8/1993 | Hascoet et al. |
| 5,246,438 A | 9/1993 | Langberg |
| 5,272,301 A | 12/1993 | Finger et al. |
| 5,295,955 A | 3/1994 | Rosen et al. |
| 5,301,692 A | 4/1994 | Knowlton |
| 5,305,748 A | 4/1994 | Wilk |
| 5,315,994 A | 5/1994 | Guibert et al. |
| 5,316,000 A | 5/1994 | Chapelon et al. |
| 5,364,336 A | 11/1994 | Carr |
| 5,364,394 A | 11/1994 | Mehl |
| 5,383,917 A | 1/1995 | Desai et al. |
| 5,385,544 A | 1/1995 | Edwards et al. |
| 5,405,346 A | 4/1995 | Grundy et al. |
| 5,407,440 A | 4/1995 | Zinreich et al. |
| 5,409,484 A | 4/1995 | Erlich et al. |
| 5,421,819 A | 6/1995 | Edwards et al. |
| 5,425,728 A | 6/1995 | Tankovich |
| 5,431,650 A | 7/1995 | Cosmescu |
| 5,433,740 A | 7/1995 | Yamaguchi |
| 5,441,532 A | 8/1995 | Fenn |
| 5,443,487 A | 8/1995 | Guibert et al. |
| 5,462,521 A | 10/1995 | Brucker et al. |
| 5,474,071 A | 12/1995 | Chapelon et al. |
| 5,503,150 A | 4/1996 | Evans |
| 5,507,741 A | 4/1996 | L'Esperance, Jr. |
| 5,507,790 A | 4/1996 | Weiss |
| 5,509,929 A | 4/1996 | Hascoet et al. |
| 5,522,814 A | 6/1996 | Bernaz |
| 5,531,662 A | 7/1996 | Carr |
| 5,540,681 A | 7/1996 | Strul et al. |
| 5,549,639 A | 8/1996 | Ross |
| 5,553,612 A | 9/1996 | Lundback |
| 5,569,237 A | 10/1996 | Beckenstein |
| 5,571,154 A | 11/1996 | Ren |
| 5,575,789 A | 11/1996 | Bell et al. |
| 5,584,830 A | 12/1996 | Ladd et al. |
| 5,586,981 A | 12/1996 | Hu |
| 5,595,568 A | 1/1997 | Anderson et al. |
| 5,649,973 A | 7/1997 | Tierney et al. |
| 5,660,836 A | 8/1997 | Knowlton |
| 5,662,110 A | 9/1997 | Carr |
| 5,669,916 A | 9/1997 | Anderson |
| 5,674,219 A | 10/1997 | Monson et al. |
| 5,683,381 A | 11/1997 | Carr et al. |
| 5,683,382 A | 11/1997 | Lenihan et al. |
| 5,690,614 A | 11/1997 | Carr et al. |
| 5,707,403 A | 1/1998 | Grove et al. |
| 5,724,966 A | 3/1998 | Lundback |
| 5,733,269 A | 3/1998 | Fuisz |
| 5,735,844 A | 4/1998 | Anderson et al. |
| 5,742,392 A | 4/1998 | Anderson et al. |
| 5,743,899 A | 4/1998 | Zinreich |
| 5,755,753 A | 5/1998 | Knowlton |
| 5,769,879 A | 6/1998 | Richards et al. |
| 5,776,127 A | 7/1998 | Anderson et al. |
| 5,782,897 A | 7/1998 | Carr |
| 5,810,801 A | 9/1998 | Anderson et al. |
| 5,810,804 A | 9/1998 | Gough et al. |
| 5,814,996 A | 9/1998 | Winter |
| 5,824,023 A | 10/1998 | Anderson |
| 5,830,208 A | 11/1998 | Muller |
| 5,836,999 A | 11/1998 | Eckhouse et al. |
| 5,868,732 A | 2/1999 | Waldman et al. |
| 5,879,346 A | 3/1999 | Waldman et al. |
| 5,891,094 A | 4/1999 | Masterson et al. |
| 5,897,549 A | 4/1999 | Tankovich |
| 5,902,263 A | 5/1999 | Patterson et al. |
| 5,904,709 A | 5/1999 | Arndt et al. |
| 5,919,218 A | 7/1999 | Carr |
| 5,928,797 A | 7/1999 | Vineberg |
| 5,931,860 A | 8/1999 | Reid et al. |
| 5,949,845 A | 9/1999 | Sterzer |
| 5,971,982 A | 10/1999 | Betsill et al. |
| 5,979,454 A | 11/1999 | Anvari et al. |
| 5,983,124 A | 11/1999 | Carr |

(56) References Cited

U.S. PATENT DOCUMENTS

| | | |
|---|---|---|
| 5,983,900 A | 11/1999 | Clement et al. |
| 5,989,245 A | 11/1999 | Pescott |
| 6,015,404 A | 1/2000 | Altshuler et al. |
| 6,024,095 A | 2/2000 | Stanley, III |
| 6,026,331 A | 2/2000 | Feldberg et al. |
| 6,026,816 A | 2/2000 | McMillan et al. |
| 6,030,378 A | 2/2000 | Stewart |
| 6,036,632 A | 3/2000 | Whitmore, III et al. |
| 6,047,215 A | 4/2000 | McClure et al. |
| 6,050,990 A | 4/2000 | Tankovich et al. |
| 6,077,294 A | 6/2000 | Cho et al. |
| 6,080,146 A | 6/2000 | Altshuler et al. |
| 6,093,186 A | 7/2000 | Goble |
| 6,097,985 A | 8/2000 | Kasevich et al. |
| 6,104,959 A | 8/2000 | Spertell |
| 6,106,514 A | 8/2000 | O'Donnell, Jr. |
| 6,113,559 A | 9/2000 | Klopotek |
| 6,113,593 A | 9/2000 | Tu et al. |
| 6,126,636 A | 10/2000 | Naka |
| 6,129,696 A | 10/2000 | Sibalis |
| 6,139,569 A | 10/2000 | Ingle et al. |
| 6,149,644 A | 11/2000 | Xie |
| 6,162,212 A | 12/2000 | Kreindel et al. |
| 6,162,218 A | 12/2000 | Elbrecht et al. |
| 6,171,301 B1 | 1/2001 | Nelson et al. |
| 6,175,768 B1 | 1/2001 | Arndt et al. |
| 6,181,970 B1 | 1/2001 | Kasevich |
| 6,183,773 B1 | 2/2001 | Anderson |
| 6,187,001 B1 | 2/2001 | Azar et al. |
| 6,197,020 B1 | 3/2001 | O'Donnell, Jr. |
| 6,208,903 B1 | 3/2001 | Richards et al. |
| 6,210,367 B1 | 4/2001 | Carr |
| 6,214,034 B1 | 4/2001 | Azar |
| 6,223,076 B1 | 4/2001 | Tapper |
| 6,231,569 B1 | 5/2001 | Bek et al. |
| 6,235,016 B1 | 5/2001 | Stewart |
| 6,241,753 B1 | 6/2001 | Knowlton |
| 6,245,062 B1 | 6/2001 | Berube et al. |
| 6,264,652 B1 | 7/2001 | Eggers et al. |
| 6,273,884 B1 | 8/2001 | Altshuler et al. |
| 6,277,104 B1 | 8/2001 | Lasko et al. |
| 6,277,111 B1 | 8/2001 | Clement et al. |
| 6,277,116 B1 | 8/2001 | Utely et al. |
| 6,280,441 B1 | 8/2001 | Ryan |
| 6,283,956 B1 | 9/2001 | McDaniel |
| 6,283,987 B1 | 9/2001 | Laird et al. |
| 6,287,302 B1 | 9/2001 | Berube |
| 6,290,699 B1 | 9/2001 | Hall et al. |
| 6,293,941 B1 | 9/2001 | Strul et al. |
| 6,306,128 B1 | 10/2001 | Waldman et al. |
| 6,306,130 B1 | 10/2001 | Anderson et al. |
| 6,319,211 B1 | 11/2001 | Ito et al. |
| 6,322,584 B2 | 11/2001 | Ingle et al. |
| 6,325,769 B1 | 12/2001 | Klopotek |
| 6,325,796 B1 | 12/2001 | Berube et al. |
| 6,330,479 B1 | 12/2001 | Stauffer |
| 6,334,074 B1 | 12/2001 | Spertell |
| 6,347,251 B1 | 2/2002 | Deng |
| 6,350,263 B1 | 2/2002 | Wetzig et al. |
| 6,350,276 B1 | 2/2002 | Knowlton |
| 6,361,531 B1 | 3/2002 | Hissong |
| 6,364,876 B1 | 4/2002 | Erb et al. |
| 6,383,176 B1 | 5/2002 | Connors et al. |
| 6,387,103 B2 | 5/2002 | Shadduck |
| 6,402,739 B1 | 6/2002 | Neev |
| 6,409,720 B1 | 6/2002 | Hissong et al. |
| 6,409,722 B1 | 6/2002 | Hoey et al. |
| 6,413,253 B1 | 7/2002 | Koop et al. |
| 6,413,254 B1 | 7/2002 | Hissong et al. |
| 6,413,255 B1 | 7/2002 | Stern |
| 6,427,089 B1 | 7/2002 | Knowlton |
| 6,428,532 B1 | 8/2002 | Doukas et al. |
| 6,430,446 B1 | 8/2002 | Knowlton |
| 6,436,094 B1 | 8/2002 | Reuter |
| 6,436,127 B1 | 8/2002 | Anderson et al. |
| 6,443,914 B1 | 9/2002 | Costantino |
| 6,443,946 B2 | 9/2002 | Clement et al. |
| 6,451,013 B1 | 9/2002 | Bays et al. |
| 6,451,015 B1 | 9/2002 | Rittman, III et al. |
| 6,456,865 B2 | 9/2002 | Samson |
| 6,457,476 B1 | 10/2002 | Elmer et al. |
| 6,461,378 B1 | 10/2002 | Knowlton |
| 6,468,235 B2 | 10/2002 | Ito et al. |
| 6,470,216 B1 | 10/2002 | Knowlton |
| 6,471,662 B1 | 10/2002 | Jaggy et al. |
| 6,471,696 B1 | 10/2002 | Berube et al. |
| 6,475,179 B1 | 11/2002 | Wang et al. |
| 6,475,211 B2 | 11/2002 | Chess et al. |
| 6,480,746 B1 | 11/2002 | Ingle et al. |
| 6,485,484 B1 | 11/2002 | Connors et al. |
| 6,485,703 B1 | 11/2002 | Coté et al. |
| 6,500,141 B1 | 12/2002 | Irion et al. |
| 6,508,813 B1 | 1/2003 | Altshuler |
| 6,514,250 B1 | 2/2003 | Jahns et al. |
| 6,517,532 B1 | 2/2003 | Altshuler et al. |
| 6,529,778 B2 | 3/2003 | Prutchi |
| 6,558,382 B2 | 5/2003 | Jahns et al. |
| 6,575,969 B1 | 6/2003 | Rittman, III et al. |
| 6,577,903 B1 | 6/2003 | Cronin et al. |
| 6,584,360 B2 | 6/2003 | Francischelli et al. |
| 6,585,733 B2 | 7/2003 | Wellman |
| 6,595,934 B1 | 7/2003 | Hissong et al. |
| 6,600,951 B1 | 7/2003 | Anderson |
| 6,605,080 B1 | 8/2003 | Altshuler et al. |
| 6,607,498 B2 | 8/2003 | Eshel |
| 6,626,854 B2 | 9/2003 | Friedman et al. |
| 6,628,990 B1 | 9/2003 | Habib et al. |
| 6,629,974 B2 | 10/2003 | Penny et al. |
| 6,645,162 B2 | 11/2003 | Friedman et al. |
| 6,648,904 B2 | 11/2003 | Altshuler et al. |
| 6,652,518 B2 | 11/2003 | Wellman et al. |
| 6,653,618 B2 | 11/2003 | Zenzie |
| 6,662,054 B2 | 12/2003 | Kreindel et al. |
| 6,663,659 B2 | 12/2003 | McDaniel |
| 6,676,654 B1 | 1/2004 | Balle Petersen et al. |
| 6,676,655 B2 | 1/2004 | McDaniel |
| 6,682,501 B1 | 1/2004 | Nelson et al. |
| 6,692,450 B1 | 2/2004 | Coleman |
| 6,723,090 B2 | 4/2004 | Altshuler et al. |
| 6,725,095 B2 | 4/2004 | Fenn et al. |
| 6,736,810 B2 | 5/2004 | Hoey et al. |
| 6,743,222 B2 | 6/2004 | Durkin et al. |
| 6,763,836 B2 | 7/2004 | Tasto et al. |
| 6,766,202 B2 | 7/2004 | Underwood et al. |
| 6,807,446 B2 | 10/2004 | Fenn et al. |
| 6,808,532 B2 | 10/2004 | Andersen et al. |
| 6,821,274 B2 | 11/2004 | McHale et al. |
| 6,823,216 B1 | 11/2004 | Salomir et al. |
| 6,824,542 B2 | 11/2004 | Jay |
| 6,856,839 B2 | 2/2005 | Litovitz |
| 6,861,954 B2 | 3/2005 | Levin |
| 6,878,144 B2 | 4/2005 | Altshuler et al. |
| 6,878,147 B2 | 4/2005 | Prakash et al. |
| 6,881,212 B1 | 4/2005 | Clement et al. |
| 6,887,239 B2 | 5/2005 | Elstrom et al. |
| 6,887,260 B1 | 5/2005 | McDaniel |
| 6,888,319 B2 | 5/2005 | Inochkin et al. |
| 6,897,238 B2 | 5/2005 | Anderson |
| 6,907,879 B2 | 6/2005 | Drinan et al. |
| 6,916,316 B2 | 7/2005 | Jay |
| 6,918,908 B2 | 7/2005 | Bonner et al. |
| 6,939,344 B2 | 9/2005 | Kreindel |
| 6,939,346 B2 | 9/2005 | Kannenberg et al. |
| 6,955,672 B2 | 10/2005 | Cense et al. |
| 6,974,415 B2 | 12/2005 | Cerwin et al. |
| 6,976,984 B2 | 12/2005 | Cense et al. |
| 6,997,923 B2 | 2/2006 | Anderson et al. |
| 7,006,874 B2 | 2/2006 | Knowlton et al. |
| 7,022,121 B2 | 4/2006 | Stern et al. |
| 7,029,469 B2 | 4/2006 | Vasily |
| 7,033,352 B1 | 4/2006 | Gauthier et al. |
| 7,044,959 B2 | 5/2006 | Anderson et al. |
| 7,056,318 B2 | 6/2006 | Black |
| 7,066,929 B1 | 6/2006 | Azar et al. |

(56) References Cited

U.S. PATENT DOCUMENTS

| | | |
|---|---|---|
| 7,074,218 B2 | 7/2006 | Washington et al. |
| 7,081,111 B2 | 7/2006 | Svaasand et al. |
| 7,089,054 B2 | 8/2006 | Palti |
| 7,107,997 B1 | 9/2006 | Moses et al. |
| 7,115,123 B2 | 10/2006 | Knowlton et al. |
| 7,118,590 B1 | 10/2006 | Cronin |
| 7,122,029 B2 | 10/2006 | Koop et al. |
| 7,128,739 B2 | 10/2006 | Prakash et al. |
| 7,135,033 B2 | 11/2006 | Altshuler et al. |
| 7,136,699 B2 | 11/2006 | Palti |
| 7,141,049 B2 | 11/2006 | Stern et al. |
| 7,151,964 B2 | 12/2006 | Desai et al. |
| 7,153,256 B2 | 12/2006 | Riehl et al. |
| 7,153,285 B2 | 12/2006 | Lauman et al. |
| 7,162,291 B1 | 1/2007 | Nachaliel |
| 7,163,536 B2 | 1/2007 | Godara |
| 7,175,950 B2 | 2/2007 | Anderson et al. |
| 7,189,230 B2 | 3/2007 | Knowlton |
| 7,192,429 B2 | 3/2007 | Trembly |
| 7,204,832 B2 | 4/2007 | Altshuler et al. |
| 7,217,265 B2 | 5/2007 | Hennings et al. |
| 7,220,254 B2 | 5/2007 | Altshuler et al. |
| 7,220,778 B2 | 5/2007 | Anderson et al. |
| 7,229,436 B2 | 6/2007 | Stern et al. |
| 7,234,739 B2 | 6/2007 | Saitoh et al. |
| 7,238,182 B2 | 7/2007 | Swoyer et al. |
| 7,241,291 B2 | 7/2007 | Kreindel et al. |
| 7,247,155 B2 | 7/2007 | Hoey et al. |
| 7,250,047 B2 | 7/2007 | Anderson et al. |
| 7,252,628 B2 | 8/2007 | Van Hal et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,290,326 B2 | 11/2007 | Dutton |
| 7,309,335 B2 | 12/2007 | Altshuler et al. |
| 7,311,674 B2 | 12/2007 | Gingrich et al. |
| 7,329,273 B2 | 2/2008 | Altshuler et al. |
| 7,329,274 B2 | 2/2008 | Altshuler et al. |
| 7,331,951 B2 | 2/2008 | Eshel et al. |
| 7,344,587 B2 | 3/2008 | Khan et al. |
| 7,347,855 B2 | 3/2008 | Eshel et al. |
| 7,351,252 B2 | 4/2008 | Altshuler et al. |
| 7,354,448 B2 | 4/2008 | Altshuler et al. |
| 7,367,341 B2 | 5/2008 | Anderson et al. |
| 7,377,917 B2 | 5/2008 | Trembly |
| 7,399,297 B2 | 7/2008 | Ikadai et al. |
| 7,422,586 B2 | 9/2008 | Morris et al. |
| 7,422,598 B2 | 9/2008 | Altshuler et al. |
| 7,431,718 B2 | 10/2008 | Ikadai |
| 7,470,270 B2 | 12/2008 | Azar et al. |
| 7,479,101 B2 | 1/2009 | Hunter et al. |
| 7,481,807 B2 | 1/2009 | Knudsen et al. |
| 7,491,171 B2 | 2/2009 | Barthe et al. |
| 7,524,328 B2 | 4/2009 | Connors et al. |
| 7,530,356 B2 | 5/2009 | Slayton et al. |
| 7,530,958 B2 | 5/2009 | Slayton et al. |
| 7,540,869 B2 | 6/2009 | Altshuler et al. |
| 7,544,204 B2 | 6/2009 | Krespi et al. |
| 7,565,207 B2 | 7/2009 | Turner et al. |
| 7,568,619 B2 | 8/2009 | Todd et al. |
| 7,588,547 B2 | 9/2009 | Deem et al. |
| 7,599,745 B2 | 10/2009 | Palti |
| 7,601,128 B2 | 10/2009 | Deem et al. |
| 7,613,523 B2 | 11/2009 | Eggers et al. |
| 7,630,774 B2 | 12/2009 | Karni et al. |
| 7,643,883 B2 | 1/2010 | Kreindel |
| 7,682,321 B2 | 3/2010 | Naldoni |
| 7,713,234 B2 | 5/2010 | Karanzas |
| 7,722,535 B2 | 5/2010 | Randlov et al. |
| 7,722,600 B2 | 5/2010 | Connors et al. |
| 7,722,656 B1 | 5/2010 | Segal |
| 7,736,360 B2 | 6/2010 | Mody et al. |
| 7,740,600 B2 | 6/2010 | Slatkine et al. |
| 7,740,651 B2 | 6/2010 | Barak et al. |
| 7,749,260 B2 | 7/2010 | Da Silva et al. |
| 7,758,524 B2 | 7/2010 | Barthe et al. |
| 7,758,537 B1 | 7/2010 | Brunell et al. |
| 7,762,964 B2 | 7/2010 | Slatkine |
| 7,763,060 B2 | 7/2010 | Baumann |
| 7,771,421 B2 | 8/2010 | Stewart et al. |
| 7,799,019 B2 | 9/2010 | Turovskiy et al. |
| 7,805,201 B2 | 9/2010 | Palti |
| 7,815,570 B2 | 10/2010 | Eshel et al. |
| 7,815,633 B2 | 10/2010 | Zanelli et al. |
| 7,824,394 B2 | 11/2010 | Manstein |
| 7,828,734 B2 | 11/2010 | Azhari et al. |
| 7,837,694 B2 | 11/2010 | Tethrake et al. |
| 7,842,029 B2 | 11/2010 | Anderson et al. |
| 7,854,754 B2 | 12/2010 | Ting et al. |
| 7,857,773 B2 | 12/2010 | Desilets et al. |
| 7,857,775 B2 | 12/2010 | Rosenberg et al. |
| 7,862,564 B2 | 1/2011 | Goble |
| 7,864,129 B2 | 1/2011 | Konishi |
| 7,891,362 B2 | 2/2011 | Domankevitz et al. |
| 7,905,844 B2 | 3/2011 | Desilets et al. |
| 8,073,550 B1 | 12/2011 | Spertell |
| 8,211,099 B2 | 7/2012 | Buysse et al. |
| 8,343,145 B2 | 1/2013 | Brannan |
| 8,367,959 B2 | 2/2013 | Spertell |
| 8,394,092 B2 | 3/2013 | Brannan |
| 8,401,668 B2 | 3/2013 | Deem et al. |
| 8,406,894 B2 | 3/2013 | Johnson et al. |
| 8,469,951 B2 | 6/2013 | Ben-Haim et al. |
| 8,535,302 B2 | 9/2013 | Ben-Haim et al. |
| 8,688,228 B2 | 4/2014 | Johnson et al. |
| 8,825,176 B2 | 9/2014 | Johnson et al. |
| 8,853,600 B2 | 10/2014 | Spertell |
| 8,939,914 B2 | 1/2015 | Turnquist et al. |
| 9,028,477 B2 | 5/2015 | Ben-Haim et al. |
| 9,149,331 B2 | 10/2015 | Deem et al. |
| 9,216,058 B2 | 12/2015 | Spertell |
| 9,241,763 B2 | 1/2016 | Kim et al. |
| 9,314,301 B2 | 4/2016 | Ben-Haim et al. |
| 2001/0016761 A1 | 8/2001 | Rudie et al. |
| 2001/0050083 A1 | 12/2001 | Marchitto et al. |
| 2002/0062124 A1 | 5/2002 | Keane |
| 2002/0087151 A1 | 7/2002 | Mody et al. |
| 2002/0156471 A1 | 10/2002 | Stern et al. |
| 2002/0165529 A1 | 11/2002 | Danek |
| 2002/0193851 A1 | 12/2002 | Silverman et al. |
| 2003/0004082 A1 | 1/2003 | Masschelein et al. |
| 2003/0120269 A1 | 6/2003 | Bessette et al. |
| 2003/0130575 A1 | 7/2003 | Desai |
| 2003/0130711 A1 | 7/2003 | Pearson et al. |
| 2003/0158566 A1 | 8/2003 | Brett |
| 2003/0212393 A1 | 11/2003 | Knowlton et al. |
| 2003/0216728 A1 | 11/2003 | Stern et al. |
| 2003/0220639 A1 | 11/2003 | Chapelon et al. |
| 2004/0000316 A1 | 1/2004 | Knowlton et al. |
| 2004/0002705 A1 | 1/2004 | Knowlton et al. |
| 2004/0049251 A1 | 3/2004 | Knowlton |
| 2004/0073115 A1 | 4/2004 | Horzewski et al. |
| 2004/0092875 A1 | 5/2004 | Kochamba |
| 2004/0140028 A1 | 7/2004 | Clark et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0230260 A1 | 11/2004 | Macfarland et al. |
| 2004/0243182 A1 | 12/2004 | Cohen et al. |
| 2004/0243200 A1 | 12/2004 | Turner et al. |
| 2004/0249426 A1 | 12/2004 | Hoenig et al. |
| 2005/0010271 A1 | 1/2005 | Merchant |
| 2005/0137654 A1 | 6/2005 | Hoenig et al. |
| 2005/0215901 A1 | 9/2005 | Anderson et al. |
| 2005/0215987 A1 | 9/2005 | Slatkine |
| 2005/0251117 A1 | 11/2005 | Anderson et al. |
| 2005/0251120 A1 | 11/2005 | Anderson et al. |
| 2005/0288666 A1 | 12/2005 | Bertolero et al. |
| 2006/0020309 A1 | 1/2006 | Altshuler et al. |
| 2006/0036300 A1 | 2/2006 | Kreindel |
| 2006/0111744 A1 | 5/2006 | Makin et al. |
| 2006/0112698 A1 | 6/2006 | Cazzini et al. |
| 2006/0129209 A1 | 6/2006 | McDaniel |
| 2006/0151485 A1 | 7/2006 | Cronin |

(56) References Cited

U.S. PATENT DOCUMENTS

| | | |
|---|---|---|
| 2006/0161228 A1 | 7/2006 | Lach |
| 2006/0167498 A1 | 7/2006 | Dilorenzo |
| 2006/0184205 A1 | 8/2006 | Schuler et al. |
| 2006/0189964 A1 | 8/2006 | Anderson et al. |
| 2006/0206110 A1 | 9/2006 | Knowlton et al. |
| 2006/0259102 A1 | 11/2006 | Slatkine |
| 2006/0264926 A1 | 11/2006 | Kochamba |
| 2006/0265034 A1 | 11/2006 | Aknine et al. |
| 2006/0271028 A1 | 11/2006 | Altshuler et al. |
| 2006/0276860 A1 | 12/2006 | Ferren et al. |
| 2007/0010810 A1 | 1/2007 | Kochamba |
| 2007/0016032 A1 | 1/2007 | Aknine |
| 2007/0020355 A1 | 1/2007 | Schlebusch et al. |
| 2007/0049918 A1 | 3/2007 | Van Der Weide et al. |
| 2007/0060989 A1 | 3/2007 | Deem et al. |
| 2007/0078290 A1 | 4/2007 | Esenaliev |
| 2007/0078502 A1 | 4/2007 | Weber et al. |
| 2007/0088413 A1 | 4/2007 | Weber et al. |
| 2007/0179482 A1 | 8/2007 | Anderson |
| 2007/0179535 A1 | 8/2007 | Morrissey et al. |
| 2007/0208399 A1 | 9/2007 | Turner et al. |
| 2007/0233226 A1 | 10/2007 | Kochamba et al. |
| 2007/0237620 A1 | 10/2007 | Mühlhoff et al. |
| 2007/0239140 A1 | 10/2007 | Chechelski et al. |
| 2007/0255355 A1 | 11/2007 | Altshuler et al. |
| 2007/0255362 A1 | 11/2007 | Levinson et al. |
| 2007/0265585 A1 | 11/2007 | Joshi et al. |
| 2007/0270925 A1 | 11/2007 | Levinson |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0091183 A1 | 4/2008 | Knopp et al. |
| 2008/0119830 A1 | 5/2008 | Ramstad et al. |
| 2008/0154259 A1 | 6/2008 | Gough et al. |
| 2008/0167585 A1 | 7/2008 | Khen et al. |
| 2008/0195000 A1 | 8/2008 | Spooner et al. |
| 2008/0228526 A1 | 9/2008 | Locke et al. |
| 2008/0269851 A1 | 10/2008 | Deem et al. |
| 2008/0294152 A1 | 11/2008 | Altshuler et al. |
| 2008/0319437 A1 | 12/2008 | Turner et al. |
| 2009/0221999 A1 | 9/2009 | Shahidi |
| 2009/0299361 A1 | 12/2009 | Flyash et al. |
| 2009/0299364 A1 | 12/2009 | Batchelor et al. |
| 2009/0306647 A1 | 12/2009 | Leyh et al. |
| 2009/0306659 A1 | 12/2009 | Buysse |
| 2009/0318917 A1 | 12/2009 | Leyh et al. |
| 2010/0010480 A1 | 1/2010 | Mehta et al. |
| 2010/0016782 A1 | 1/2010 | Oblong |
| 2010/0114086 A1 | 5/2010 | Deem et al. |
| 2010/0211059 A1 | 8/2010 | Deem et al. |
| 2011/0015687 A1 | 1/2011 | Nebrigic et al. |
| 2011/0028898 A1 | 2/2011 | Clark, III et al. |
| 2011/0112520 A1 | 5/2011 | Kreindel |
| 2011/0196365 A1 | 8/2011 | Kim et al. |
| 2011/0313412 A1 | 12/2011 | Kim et al. |
| 2012/0078141 A1 | 3/2012 | Knowlton |
| 2012/0265277 A1 | 10/2012 | Unetich |
| 2013/0150844 A1 | 6/2013 | Deem et al. |
| 2014/0180271 A1 | 6/2014 | Johnson et al. |
| 2015/0148792 A1 | 5/2015 | Kim et al. |
| 2015/0351838 A1 | 12/2015 | Deem et al. |
| 2016/0045755 A1 | 2/2016 | Chun et al. |
| 2016/0135888 A1 | 5/2016 | Kim et al. |
| 2017/0252105 A1 | 9/2017 | Deem et al. |

FOREIGN PATENT DOCUMENTS

| | | | |
|---|---|---|---|
| CN | 1781462 A | | 6/2006 |
| EP | 0139607 B1 | | 4/1990 |
| EP | 0370890 B1 | | 11/1995 |
| EP | 1346753 A2 | | 9/2003 |
| JP | 61-364 A | | 1/1986 |
| JP | 62-149347 | | 9/1987 |
| JP | S-63177856 A | | 7/1988 |
| JP | 07-503874 A | | 4/1995 |
| JP | H09-239040 A | | 9/1997 |
| JP | 2001-514921 A | | 9/2001 |
| JP | 2006503618 | | 2/2006 |
| JP | 2006-289098 | | 10/2006 |
| JP | 2007191192 A | | 8/2007 |
| JP | 2010524587 A | | 7/2010 |
| JP | 54-079994 B2 | | 11/2013 |
| WO | WO 89/02292 A1 | | 3/1989 |
| WO | WO 92/07622 A1 | | 5/1992 |
| WO | WO 96/23447 A1 | | 8/1996 |
| WO | WO 96/41579 A1 | | 12/1996 |
| WO | WO 99/46005 A1 | | 9/1999 |
| WO | WO 00/24463 A2 | | 5/2000 |
| WO | WO 01/58361 A1 | | 8/2001 |
| WO | WO 03/039385 A2 | | 5/2003 |
| WO | WO 2004/034925 A2 | | 4/2004 |
| WO | WO 2005/060354 A2 | | 7/2005 |
| WO | WO 2005/099369 A2 | | 10/2005 |
| WO | WO 2005/112807 A2 | | 12/2005 |
| WO | WO 2005/120379 A2 | | 12/2005 |
| WO | WO2005/122694 A2 | | 12/2005 |
| WO | WO 2006/089227 A2 | | 8/2006 |
| WO | WO 2006/090217 A1 | | 8/2006 |
| WO | WO 2006/117682 A2 | | 11/2006 |
| WO | WO 2006/122136 A2 | | 11/2006 |
| WO | WO 2007/015247 A2 | | 2/2007 |
| WO | WO 2007/030367 A2 | | 3/2007 |
| WO | WO 2007/038567 A1 | | 4/2007 |
| WO | WO 2007/050572 A2 | | 5/2007 |
| WO | WO2007/093998 A1 | | 8/2007 |
| WO | WO 2007/106339 A2 | | 9/2007 |
| WO | WO 2007/108516 A1 | | 9/2007 |
| WO | WO 2007/131112 A2 | | 11/2007 |
| WO | WO 2007/140469 A2 | | 12/2007 |
| WO | WO2008/068485 A2 | | 6/2008 |
| WO | WO 2009/072108 A2 | | 6/2009 |
| WO | WO2009/075879 A1 | | 6/2009 |
| WO | WO2010/047818 A1 | | 4/2010 |
| WO | WO 2011/087852 A2 | | 7/2011 |
| WO | WO 2012/072250 A1 | | 6/2012 |
| WO | WO2012/138056 A1 | | 10/2012 |
| WO | WO2013/074664 A1 | | 5/2013 |

OTHER PUBLICATIONS

Deem et al.; U.S. Appl. No. 15/252,109 entitled "Systems and methods for creating an effect using microwave energy to specified tissue," filed Aug. 30, 2016.

Deem et al.; U.S. Appl. No. 15/288,949 entitled "Methods, devices, and systems for non-invasive delivery of microwave therapy," filed Oct. 7, 2016.

Abraham et al.; Monopolar radiofrequency skin tightening; Facial Plast Surg Clin N Am; 15(2); pp. 169-177; May 2007.

Absar et al.; Efficacy of botulinum toxin type A in the treatment of focal axillary hyperhidrosis; Dermatol Surg; 34(6); pp. 751-755; Jun. 2008.

Acculis; Microwave Ablation for Healthcare Professionals; 2 pgs.; accessed Jun. 24, 2008; (http://www.acculis.com/mta).

Aesthera US—How it Works; 2 pgs.; accessed Jul. 8, 2008 (http://www.aesthera.com/go/aestheralUS/patients/how_it_works/index.cfm).

Allergan Pharmaceuticals; Botox® (product insert); 16 pgs.; Oct. 2006.

Alster et al.; Improvement of neck and cheek laxity with a non-ablative radiofrequency device: a lifting experience; Dermatol Surg; 30(4); pp. 503-507; Apr. 2004.

Ananthanarayanan et al.; 2.5 GHz microwave thermal ablation for performing thermosensitive polymer-chemotherapy for cancer; Antennas and Propagation Society Int. Symp. (APSURSI), 2010 IEEE; Toronto, ON, Canada; pp. 1-4; Jul. 11-17, 2010.

Arneja et al.; Axillary hyperhidrosis: a 5-year review of treatment efficacy and recurrence rates using a new arthroscopic shaver technique; Plast. Reconstr. Surg.; vol. 119; pp. 562-567; Feb. 2007.

Ashby et al.; Cryosurgery for Axillary Hyperhidrosis; British Medical Journal Short Reports; London; pp. 1173-1174; Nov. 13, 1976.

(56) References Cited

OTHER PUBLICATIONS

Atkins et al.; Hyperhidrosis: A Review of Current Management; Plast Reconstr Surg; 110(1); pp. 222-228; Jul. 2002.

Avedro; Keraflex KXL—A new treatment option in European clinical trials; 1 pg.; Sep. 2009; printed Jun. 18, 2012 from website (http://www.nkcf.org/research/research-update/139-kxl-clinical-trials.html).

Ball, P.; Radio sweat gland—90 GHz; Nature; 452(7188); p. 676; Apr. 9, 2008; printed Jun. 18, 2012 from website (http://www.nature.com/news/2008/080409/full/452676a.html).

Basra et al.; The dermatology life quality index 1994R2007: A comprehensive review of validation data and clinical results; Br J Dermatol;159(5); pp. 997-1035; Nov. 2008.

Bechara et al.; Histological and clinical findings in different surgical strategies for focal axillary hyperhidrosis; Dermatol Surg; vol. 34; pp. 1001-1009; Aug. 2008.

Beer et al., Immunohistochemical Differentiation and Localization Analysis of Sweat Glands in the Adult Human Axilla, Plastic and Reconstructive Surgery, vol. 117, No. 6, pp. 2043-2049, May 2006.

Bentel et al.; Variability of the depth of supraclavicular and axillary lymph nodes in patients with breast cancer: is a posterior axillary boost field necessary?; Int J Radiation Oncology Biol Phys; vol. 47(3); pp. 755-758; Jun. 2000.

Bindu et al.; Microwave characterization of breast-phantom materials; Microwave and Optical Tech. Letters; 43(6); pp. 506-508; Dec. 20, 2004.

Bioportfolio; Tenex Health Receives FDA clearance for innovative TX1} tissue removal system; 2 pgs.; release dated Mar. 9, 2011; printed on Jun. 18, 2012 from website (http://www.bioportfolio.com/news/article/519143/Tenex-Health-Receives-Fda-Clearance-For-Innovative-Tx1-Tissue-Removal-System.html).

Blanchard et al.; Relapse and morbidity in patients undergoing sentinel lymph node biopsy alone or with axillary dissection for breast cancer; Arch Surg; vol. 138; pp. 482-488; May 2003.

Brace et al., Microwave Ablation with a Trixial Antenna: Results in ex vivo Bovine Liver, IEEE transactions on Microwave Theory and Techniques, vol. 53, No. 1, pp. 215-220 (Jan. 2005).

BSD Medical Corporation; Hyperthermia therapy contributes to 85 percent survival rate from childhood cancers; 2 pgs.; Jan. 13, 2009; printed Jun. 18, 2009 from website (http://www.irconnect.com/noc/press/pages/news_releases.html?d=157551).

Bu-Lin et al.; A polyacrylamide gel phantom for radiofrequency ablation; Int. J. Hyperthermia; 24(7); pp. 568-576; Nov. 2008.

Burns, Jay A.; Thermage: monopolar radiofrequency; Aesthetic Surg J; 25(6); pp. 638-642; Nov./Dec. 2005.

Business Wire; miraDry by Miramar Labs Receives FDA 510(k) Clearance; 2pgs.; Feb. 8, 2011; printed Jun. 18, 2012 from website (http://www.businesswire.com/news/home/20110208005595/en/miraDry-Miramar-Labs-Receives-FDA-510-Clearance).

Campbell et al.; Dielectric properties of female human breast tissue measured in vitro at 3.2 GHz; Phys. Med. Biol.; 37(1); pp. 193-210; Jan. 1992.

Candela Corp.; The Candela SeleroPLUS Laser with Dynamic Cooling Device: The Benefits of Anesthesia without the Risks; Nov. 1998.

Chang et al.; A conductive plastic for simulating biological tissue at microwave frequencies; IEEE Trans on Electromagnetic Compatibility; 42(1); pp. 76-81; Feb. 2000.

Christ et al., Characterization of the Electromagnetic Near-Field Absorption in Layered Biological Tissue in the Frequency Range from 30 MHz to 6000 MHz, Phys. Med. Biol. 51, pp. 4951-4965; Oct. 2006.

Christ et al., The Dependence of Electromagnetic Far-Field Absorption on Body Tissue Composition in the Frequency Range from 300 MHz to 6 GHz, IEEE Transactions on Microwave Theory and Techniques, vol. 54, No. 5, pp. 2188-2195 (May 2006).

CK Electronic GmbH; Scientific Measurements of Skin and Hair (product information); 15 pgs.; published after Sep. 2006.

Cobham; Antenna & Radome Design Aids (product list); 1 pg.; Aug. 2001.

Commons et al.; Treatment of axillary hyperhidrosis/bromidrosis using VASER ultrasound; Aesth Plast Surg; vol. 33(3); pp. 312-323; May 2009 (pub'd online Jan. 3, 2009).

Copty et al., Low-power near-field microwave applicator for localized heating of soft matter, Applied Physics Letters, vol. 84, No. 25, pp. 5109-5111 (Jun. 21, 2004).

Covidien; FDA clears Covidien's Evident) microwave ablation system for use in nonresectable liver tumor ablation; 2 pgs.; Dec. 28, 2008; printed Jun. 18, 2012 from website (http://www.medicalnewstoday.com/releases/133800.php).

Darabaneanu et al.; Long-term efficacy of subcutaneous sweat gland suction curettage for axillary hyperhidrosis: a prospective gravimetrically controlled study; Dermatol Surg; 34(9); pp. 1170-1177; Sep. 2008.

De Bruijne et al., Effects of waterbolus size, shape and configuration on the SAR distribution pattern of the Lucite cone applicator, International Journal of Hyperthermia, 22(1): 15-28 (Feb. 2006).

Dewey; Arrhenius relationships from the molecule and cell to the clinic; Int. J. Hyperthermia; 25(1); pp. 3-20; Feb. 2009.

Diederich et al.; Pre-clinical Evaluation of a Microwave Planar Array Applicator for Superficial Hyperthermia; International Journal of Hyperthermia; vol. 9, No. 2; pp. 227-246; Jan. 1993.

Drozd et al., Comparison of Coaxial Dipole Antennas for Applications in the Near-Field and Far-Field Regions; MW Journal, vol. 47, No. 5 (May 2004), http://www.mwjournal.com/Journal, accessed Dec. 10, 2007.

Duparc et al.; Anatomical basis of the variable aspects of injuries of the axillary nerve (excluding the terminal branches in the deltoid muscle); Surg Radiol Anat; vol. 19(3); pp. 127-132; May 1997.

Eleiwa et al.; Accurate FDTD simulation of biological tissues for bio-electromagnetic applications; IEEE Proc. SoutheastCon 2001; Clemson, SC; Mar. 30-Apr. 1, 2001; pp. 174-178.

Farace et al.; An automated method for mapping human tissue permittivities by MRI in hyperthermia treatment planning; Phys. Med. Biol.; 42(11); pp. 2159-2174; Nov. 1997.

Fitzpatrick et al.; Multicenter study of noninvasive radiofrequency for periorbital tissue tightening; Lasers Surg Med; 33(4); pp. 232-242; Mar. 2003.

Gabriel et al.; Dielectric parameters relevant to microwave dielectric heating; Chem Soc Rev; 27(3); pp. 213-224; May-Jun. 1998.

Gabriel et al.; The dielectric properties of biological tissues: I. Literature survey; Phys Med Biol; 41(11); pp. 2231-2249; Nov. 1996.

Gabriel et al.; The dielectric properties of biological tissues: II. Measurements in the frequency range 10 Hz to 20 GHz; Phys Med Biol; 41(11); pp. 2251-2269; Nov. 1996.

Gabriel et al.; The dielectric properties of biological tissues: III. Parametric models for the dielectric spectrum of tissues; Phys Med Biol; 41(11); pp. 2271-2293; Nov. 1996.

Gabriel, et al.; Comparison of the Dielectric Properties of Normal and Wounded Human Skin Material; Bioelectromagnetics; 8; pp. 23-27; Jan. 1987.

Gabriel; Compilation of the dielectric properties of body tissues at RF and microwave frequencies (Technical Report); Armstrong Laboratory; Doc. No. AL/OE-TR-1996-004; pp. 1-16; Jan. 1996.

Galloway et al.; Ultrasound imaging of the axillary vein—anatomical basis for central venous access; British ournal of Anaesthesia; 90(5); pp. 589-595; May 2003.

Gandhi et al.; Electromagnetic Absorption in the Human Head and Neck for Mobile Telephones at 835 and 1900 MHz; IEEE Transactions on Microwave Theory and Techniques; 44(10); pp. 1884-1897; Oct. 1996.

Gandhi et al.; Electromagnetic Absorption in the Human Head from Experimental 6-GHz Handheld Transceivers; IEEE Trans. on Electromagnetic Compatibility; 37(4); pp. 547-558; Nov. 1995.

Garber, B. B.; Office microwave treatment of enlarged prostate symptoms; 2 pgs.; printed from website (http://www.garber-online.com/microwave-treatment.htm) on Jun. 18, 2012.

Glaser et al.; A randomized, blinded clinical evaluation of a novel microwave device for treating axillary hyperhidrosis: the dermatologic reduction in underarm perspiration study; Dermatol Surg; 38(2); pp. 185-191; Feb. 2012.

(56) References Cited

OTHER PUBLICATIONS

Glaser et al.; A randomized, blinded clinical evaluation of a novel microwave device for treatinment of axillary hyperhidrosis; 2010 ASDS/ASCDAS Joint Annual Meeting; Late Breaking Abstract (GD413); Oct. 2010.
Gold et al.; Treatment of Wrinkles and Skin Tightening Using Aluma(TM) Skin Renewal System with FACES(TM)(Functional Aspiration Controlled Electrothermal Stimulation) Technology; Lumens, Inc. (Oct. 2005).
Goldman et al.; Subdermal Nd—YAG laser for axillary hyperhidrosis; Dermatol Surg; 34(6); pp. 756-762; Jun. 2008.
Guidant Corp.; Guidant microwave surgical ablation system; 1 pg.; © 2004; printed Jun. 18, 2012 from website (http://web.archive.org/web/20070306031424/http://www.ctsnet.org/file/vendors/872/pdf/MicrowaveAblationIFU.pdf).
Guy, Arthur; History of Biological Effects and Medical Applications of Microwave Energy; IEEE Transactions on Microwave Theory and Techniques; 32(9); pp. 1182-1200; Sep. 1984.
Guy, Arthur; Therapeutic Heat and Cold, Fourth Ed.; Chapter 5: Biophysics of High-Frequency Currents and Electromagnetic Radiation; pp. 179-236. Williams and Wilkins (publishers); Apr. 1990.
Guy; Analyses of electromagnetic fields induced in biological tissues by thermographic studies on equivalent phantom models; IEEE Trans on Microwave Theory and Techniques; MTT-19(2); pp. 205-214; Feb. 1971.
Haedersdal et al.; Evidence-based review of hair removal using lasers and light sources; JEADV; vol. 20; pp. 9-20; Jan. 2006.
Hey-Shipton, et al.; The Complex Permittivity of Human Tissue at Microwave Frequencies; Phys. Med. Biol.; 27(8); pp. 1067-1071; Aug. 1982.
Hisada et al.; Hereditary Hemorrhagic Telangiectasia Showing Severe Anemia which was successfully treated with estrogen; International Medicine; vol. 34; No. 6; pp. 589-592; Jun. 1995.
Hodgkinson, D. J.; Clinical applications of radiofrequency: nonsurgical skin tightening (thermage); Clin Plastic Surg; 36(2); pp. 261-268; Apr. 2009.
Hong et al.; Clinical evaluation of a microwave device for treating axillary hyperdrosis; Dermatol Sug; 38(5); pp. 728-735; May 2012.
Hornberger et al.; Recognition, diagnosis, and treatment of primary focal hyperhidrosis; J Am Acad Dermatol; vol. 51; pp. 274-286; Aug. 2004.
Houzen et al.; Implanted antenna for an artificial cardiac pacemaker system; Progress in Electromagnetics Research Symposium 2007; Prague, CZ; pp. 51-54; Aug. 27-30, 2007.
Hu, Da Zhang, Electromagnetic Field in Organism of Skin-Fat-Muscle, China Research Institute of Radiowave Propagation IEEE, pp. 807-812 (Aug. 1998).
Jacobsen et al.; Characteristics of microstrip muscle-loaded single-arm archimedean spiral antennas as investigated by FDTD numerical computations; IEEE Trans. On Biomedical Engineering; 52(2); pp. 321-330; Feb. 2005.
Jacobsen et al.; Characterization of a tranceiving antenna concept for microwave heating and thermometry of superficial tumors; PIER; vol. 18; pp. 105-125; (year of publication is sufficiently earlier than the effective U.S. filing date and any foreign priority date) 1998.
Jacobsen et al.; Dual-mode antenna design for microwave heating and noninvasive thermometry of superficial tissue disease; IEEE Trans. on Biomedical Engineering; 47(11); pp. 1500-1509; Nov. 2000.
Jacobsen et al.; Multifrequency radiometric determination of temperature profiles in a lossy homogeneous phantom using a dual-mode antenna with integral water bolus; IEEE Trans. on Microwave Theory and Techniques; 50(7); pp. 1737-1746; Jul. 2002.
Jacobsen et al.; Nonparametric 1-D temperature restoration in lossy media using tikhonov regularization on sparse radiometry data; IEEE Trans. on Biomedical Engineering; 50(2); pp. 178-188; Feb. 2003.
Jacobsen et al.; Transceiving antenna for homogenious heating and radiometric thermometry during hyperthermia; Electronic Letters; 36(6); pp. 496-497; Mar. 16, 2000.
Johnson et al.; Automatic temperature controller for multielement array hyperthermia systems; IEEE Trans. on Biomedical Engineering; 53(6); pp. 1006-1015; Jun. 2006.
Johnson et al.; Evaluation of a dual-arm Archimedean spiral array for microwave hyperthermia; Int J Hyperthermia; 22(6); pp. 475-490; Sep. 2006.
Johnson et al.; Microwave thermolysis of sweat glands; Lasers in Surgery and Medicine; 44(1); pp. 20-25; Jan. 2012.
Juang et al.; Construction of a conformal water bolus vest applicator for hyperthermia treatment of superficial skin cancer; Proc. of the 26th Ann. Int. Conf. of the IEEE EMBS; San Francisco, CA, USA; Sep. 1-5, 2004; pp. 3467-3470.
Kaminer et al.; First clinical use of a novel microwave device for treatment of axillary hyperhidrosis; 2010 ASDS Annual Meeting; Poster #12; Oct. 2010.
Kawoos et al., Issues in Wireless Intracranial Pressure Monitoring at Microwave Frequencies, PIERS Online, vol. 3, No. 6, pp. 927-931; (year of publication is sufficiently earlier than the effective U.S. filing date and any foreign priority date) 2007.
Kilmer et al.; A randomized, blinded clinical study of a microwave device for treatment of axillary hyperhidrosis; 31st ASLMS Annual Conference; Late-Breaking Abstract; Apr. 1-3, 2011.
Kim et al.; Implanted antennas inside a human body: Simulations, designs, and characterizations; IEEE Trans on Microwave Theory and Techniques; 52(8); pp. 1934-1943; Aug. 2004.
Kirn, T. F.; Researchers seek to quantify thermage efficacy; Dermatologic Surgery; p. 36; Jan. 2007.
Kirsch et al.; Ultrastructure of collagen thermally denatured by microsecond domain pulsed carbon dioxide laser; Arch Dermatol; 134; pp. 1255-1259; Oct. 1998.
Klemm et al.; EM energy absorption in the human body tissues due to UWB antennas; Progress in Electromagnetics Research; PIER; 62; pp. 261-280; (year of pub. sufficiently earlier than effective US filing date and any foreign priority date) 2006.
Kobayashi, T.; Electrosurgery Using Insulated Needles: Treatment of Axillary Bromhidrosis and Hyperhidrosis; Journal of Dermatologic Surgery & Oncology; 14(7) pp. 749-752; Jul. 1988.
Krusen, Frank (M.D.); Samuel Hyde Memorial Lecture: Medical Applications of Microwave Diathermy: Laboratory and Clinical Studies. Proceedings of the Royal Society of Medicine; 43(8); pp. 641-658, May 10, 1950.
Kumaradas et al.; Optimization of a beam shaping bolus for superficial microwave hyperthermia waveguide applicators using a finite element method; Phys. Med. Biol.; 48(1); pp. 1-18; Jan. 7, 2003.
Kushikata, Nobuharu, Histological Assessment of Biopsy Samples Taken Before and After the mireDry Procedure Performed on a Patient with Axillary Hyperhidrosis; Case Report; pp. 1-3; Oct. 2011.
Lagendijk et al; Hyperthermia dough: a fat and bone equivalent phantom to test microwave/radiofrequency hyperthermia heating systems; Phys. Med. Biol.; 30(7); pp. 709-712; Jul. 1985.
Land et al.; A quick accurate method for measuring the microwave dielectric properties of small tissue samples; Phys. Med. Biol.; 37(1); pp. 183-192; Jan. 1992.
Lane et al.; Pressure-Induced Bullae and Sweat Gland Necrosis Following Chemotherapy Induction; The American Journal of Medicine; vol. 117; pp. 441-443; Sep. 15, 2004.
Larson et al.; Microwave treatments for enlarged prostate cause blood pressure surges, study shows; 2 pgs.; Apr. 11, 2008; printed on Jun. 18, 2012 from website (http://web.archive.org/web/20080415000815/http://www.sciencedaily.com/releases/2008/04/080408105820.htm).
Lawrence et al.; Selective Sweat Gland Removal with Minimal Skin Excision in the Treatment of Axillary Hyperhidrosis: A Retrospective Clinical and Histological Review of 15 Patients; British Journal of Dermatology; British Association of Dermatologists; 155(1), pp. 115-118; Jul. 2006.

(56) References Cited

OTHER PUBLICATIONS

Lehmann et al.; Therapeutic Heat; Therapeutic Heat and Cold, Fourth Ed.; Chapter 9; pp. 417-581; Williams & Wilkins (publishers), Baltimore, MD; Apr. 1990.

Lowe et al.; Botulinum toxin type A in the treatment of primary axillary hyperhidrosis: A 52-week multicenter double-blind, randomized, placebo-controlled study of efficacy and safety; J Am Acad Dermatol; vol. 56; pp. 604-611; Apr. 2007.

Lowe et al.; Microwave delivery system for lower leg telangiectasia; Journal of Cutaneous Laser Therapy; 2(1); pp. 3-7; Mar. 2000.

Lumenis Inc.; Aluma RF Skin Renewal System (product information); copyright 2007 (PB-1013670); 8 pgs.; Oct. 2007 (printed version).

Lupin et al.; A Multi-Center Evaluation of the miraDry System to Treat Subjects with Axillary Hyperhidrosis; 31st ASLMS Annual Conference; Abstract # 79; Apr. 1-3, 2011.

Lupin et al.; Long-term evaluation of microwave treatment for axillary hyperhidrosis; 2012 ASLMS Annual Meeting; pp. 6-7; Abstract #19; Apr. 2012.

Lupin et al.; Microwave-based treatment for primary axillary hyperhidrosis: Six months of follow-up; J Am Acad Dermatol; 66(4), supp. 1; p. AB215; Poster #5300; Apr. 2012.

Maccarini et al.; Advances in microwave hyperthermia of large superficial tumors; Microwave Symposium Digest, IEEE MTT-S International; pp. 1797-1800; Jun. 2005.

Maccarini et al.; Electromagnetic optimization of dual mode antennas for radiometry controlled heating of superficial tissue; Proceedings of SPIE; vol. 5698; Bellingham, WA; pp. 71-81; Jan. 2005.

Maccarini et al.; Optimization of a dual concentric conductor antenna for superficial hyperthermia applications; Proc. of the 26th Ann. Int. Conf. of the IEEE EMBS; San Francisco, CA, USA; Sep. 1-5, 2004; pp. 2518-2521.

Mazzurana et al.; A semi-automatic method for developing an anthropomorphic numerical model of dielectric anatomy by MRI; Phys. Med. Biol.; 48(19); pp. 3157-3170; Oct. 7, 2003.

Medgadget; MedGadget's MedTech Monday: Treating excessive underarm sweat with microwaves; 1 pg.; Feb. 14, 2011; printed Jun. 18, 2012 from website (https://www.massdevice.com/blogs/massdevice/medgadgets-medtech-monday-treating-excessive-underarm-sweat-with-microwaves).

Medwaves, Inc.; MedWaves, Inc. sponsors investigational studies to evaluate its patented microwave thermal coagulation-ablation system for treatment of tumors in liver and lung; 4 pgs.; Sep. 18, 2009; printed Jun. 18, 2012 from website (http://www.ereleases.com/pr/medwaves-sponsors-investigational-studies-evaluate-patented-microwave-thermal-coagulationablation-system-treatment-tumors-liver-lung-25870).

Michel et al.; Design and Modeling of Microstrip—Microslot Applicators with Several Patches and Apertures for Microwave Hyperthermia; Microwave and Optical Technology Letters; vol. 14, No. 2; pp. 121-125; Feb. 5, 1997.

Mrozowski et al.; Parameterization of media dispersive properties for FDTD; IEEE Trans on Antennas and Propagation; 45(9); pp. 1438-1439; Sep. 1997.

Nagaoka et al.; Development of realistic high-resolution whole-body voxel models of Japanese adult males and females of average height and weight, and application of models to radio-frequency electromagnetic-field dosimetry; Phys. Med. Biol.; 49(1); pp. 1-15; Jan. 7, 2004.

Neuman; SAR pattern perturbations from resonance effects in water bolus layers used with superficial microwave hyperthermia applicators; Int. J. Hyperthermia; 18(3); pp. 180-193; May-Jun. 2002.

Park et al.; A Comparative Study of the Surgical Treatment of Axillary Osmidrosis by Instrument, Manual, and Combined Subcutaneous Shaving Procedures; 41(5); pp. 488-497; Nov. 1998.

Paulides et al.; A Patch Antenna Design for Application in a Phased-Array Head and Neck Hyperthermia Applicator; IEEE Transactions on Biomedical Engineering; 54(11); pp. 2057-2063; Nov. 2007.

Peyman et al.; Cole-cole parameters for the dielectric properties of porcine tissues as a function of age at microwave frequencies; Phys Med Biol; 55(15); pp. N413RN419; Jul. 2010.

Popovic et al.; Dielectric spectroscopy of breast tissue—improved model of the precision open-ended coaxial probe; Proc of the 25th Ann Int Conf of the IEEE EMBS; Cancun, Mexico; pp. 3791-3793; Sep. 17-21, 2003.

Popovic et al.; Response characterization of the precision open-ended coaxial probe for dielectric spectroscopy of breast tissue; 2003 IEEE—Anntennas and Propagation Soc. Int. Symp.; vol. 4; pp. 54-57; Jun. 22-27, 2003.

Pozar, David M.; Electromagnetic Theory (Introduction); Microwave Engineering, Second Edition; John Wiley & Sons, Inc.; p. 1; Aug. 1997.

Rappaport, C.; Treating Cardiac Disease with Catheter-Based Tissue Heating; IEEE Microwave Magazine; 3(1); pp. 57-64; Mar. 2002.

Riddle et al.; Complex permittivity measurements of common plastics over variable temperatures; IEEE Trans on Microwave Theory and Techniques; vol. 51(3); pp. 727-733; Mar. 2003.

Rolfsnes et al.; Design of spiral antennas for radiometric temperature measurement; Proc. of the 26th Ann. Int. Conf. of the IEEE EMBS; San Francisco, CA, USA; Sep. 1-5, 2004; pp. 2522-2525.

Rosen et al.; Microwaves treat heart disease; IEEE Microw Mag; 8(1); pp. 70-75; Feb. 2007.

Ross et al.; A pilot study of in vivo immediate tissue contraction with CO2 skin laser resurfacing in a live farm pig; Dermatol Surg; 25(11); pp. 851-856; Nov. 1999.

Ross et al.; Comparison of carbon dioxide laser, erbium: Yag laser, dermabrasion, and dermatome a study of thermal damage, wound contraction, and woundhealing in a live pig model: Implications for skin. resurfacing; J Am Acad Dermatol; 42(1); pp. 92-105; Jan. 2000.

Ross et al.; Use of a novel erbium laser in a yucatan minipig: A study of residual thermal damage, ablation, and wound healing as a function of pulse duration; Lasers Surg Med; 30(2); pp. 93-100; Feb. 2002.

Rossetto et al.; Effect of complex bolus-tissue load configurations on SAR distributions from dual concentric conductor applicators; IEEE Trans. on Biomedical Engineering; 46(11); pp. 1310-1319; Nov. 1999.

Saito et al.; Clinical Trials of Interstitual Microwave Hyperthermia by Use of Coaxial-Slot Antenna With Two Slots; IEEE Trans. on Microwave Theory and Techniques; vol. 52; No. 8; pp. 1987-1991; Aug. 2004.

Sherar et al.; Helical antenna arrays for interstitial microwave thermal therapy for prostate cancer: tissue phantom testing and simulations for treatment; Physics in Medicine and Biology; 46(7); pp. 1905-1918; Jul. 2001.

Shimm, D et al.; Hyperthermia in the Treatment of Malignancies; Therapeutic Heat and Cold Fourth Edition edited by Justin Lehmann M.D., Chapter 14, pp. 674-699, Williams & Wilkins Publishers, Baltimore, MD; Apr. 1990.

Sipahioglu et al.; Dielectric properties of vegetables and fruits as a function of temperature, ash, and moisture content; Journal of Food Science; 68(1); pp. 234-239; Jan. 2003.

Smith, Stacy; Evolution of a new treatment modality for primary focal hyperhidrosis(poster); Cosmetic Boot Camp 2011; Aspen, CO; Jul. 2011.

Solish et al.; A comprehensive approach to the recognition, diagnosis, and severity-based treatment of focal hyperhidrosis: recommendations of the Canadian hyperhidrosis advisory committee; Dermatol Surg; vol. 33; pp. 908-923; Aug. 2007.

Solish et al.; Prospective open-label study of botulinum toxin type A in patients with axillary hyperhodrosis: effects on functional impairment and quality of life; Dermatol Surg; vol. 31(4); pp. 405-413; Apr. 2005.

Solta Medical, Inc.; Study Published in Facial Plastic Surgery Journal Finds Selective Heating of Fibrous Septae Key to Success and Safety of Thermage(R) ThermaCool(TM) System; Thermage® Press Release; 2 pgs.; Jun. 20, 2005.

(56) References Cited

OTHER PUBLICATIONS

Soontornpipit et al.; Design of implantable microstrip antenna for communication with medical implants; IEEE Trans on Microwave Theory and Techniques; 52(8); pp. 1944-1951; Aug. 2004.
Spertell et al.; Review of clinical data on hair removal using the MW 2000 microwave delivery system (promotional material); 2000; MW Medical, Inc.; printed from http://www.hairfacts.com/medpubs/mwave/spertell.html on Jun. 23, 2009; 5 pgs.
Spertell; Presentation at the American Academy of Dermatology; MW Medical, Inc.; Mar. 10, 2000; 21 pgs.
Spertell; The application of microwaves to the treatment of cosmetic skin conditions: a technical summary; MW Medical, Inc.; pp. 1-15; May 25, 1999.
SRLI Technologies; BTC-2000} (product information); printed from website: http://www.srli.com/technologies/BTC2000.html on Nov. 16, 2009; 1 pg.
Stauffer et al.; Combination applicator for simultaneous heat and radiation; Proc. of the 26th Ann. Int. Conf. of the IEEE EMBS; San Francisco, CA, USA; Sep. 1-5, 2004; pp. 2514-2517.
Stauffer et al.; Dual mode antenna array for microwave heating and non-invasive thermometry of superficial tissue disease; SPIE Conf. on Thermal Treatment of Tissue with Image Guidance; San Jose, CA; SPIE; vol. 3594; pp. 139-147; Jan. 1999.
Stauffer et al.; Microwave array applicator for rediometry controlled superficial hyperthermia; Proc. of the SPIE; vol. 4247; pp. 19-29; Jun. 2001.
Stauffer et al.; Phantom and animal tissues for modelling the electrical properties of human liver; Int. J. Hyperthermia; 19(1); pp. 89-101; Jan.-Feb. 2003.
Stauffer et al.; Practical induction heating coil designs for clinical hyperthermia with ferromagnetic implants; IEEE Trans. on Biomedical Engineering; 41(1); pp. 17-28; Jan. 1994.
Stauffer et al.; Progress on system for applying simultaneous heat and brachytherapy to large-area surface disease; Proceedings of SPIE; vol. 5698; Bellingham, WA; pp. 82-96; Jan. 2005.
Stauffer et al.; Progress toward radiometry controlled conformal microwave array hyperthermia applicator; Proc. of the 22nd Ann. EMBS Int. Conf.; Chicago, IL; Jul. 23-28, 2000; pp. 1613-1616.
Stauffer, Paul R.; Evolving technology for thermal therapy of cancer; International Journal of Hyperthermia; 21(8); pp. 731-744; Dec. 2005.
Stauffer, Paul R.; Thermal Therapy Techniques for Skin and Superficial Tissue Disease; Critical Reviews; SPIE Optical Engineering Press (Bellingham, WA); vol. CR75; pp. 327-367; Jan. 2000.
Sterzer, Fred, Microwave Medical Devices; IEEE Microwave Magazine, 3(1); pp. 65-70; Mar. 2002.
Stoy et al.; Dielectric properties of mammalian tissues from 0.1 to 100 MHz: a summary of recent data; Phys. Med. Bil.; 27(4); pp. 501-513; Apr. 1982.
Strutton et al.; US prevalence of hyperhidrosis and impact on individuals with axillary hyperhidrosis: Results from a national survey. J Am Acad Dermatol; 51(2); pp. 241-248; Feb. 2004.
Stuchly et al.; Diathermy applicators with circular aperture and corrugated flange; IEEE Trans on Microwave Theory and Techniques; MTT-28(3); pp. 267-271; Mar. 1980.
Stuchly et al.; Dielectric properties of animal tissues in vivo at frequencies 10 MHz-1 GHz; Bioelectromagnetics; 2(2); pp. 93-103; Apr. 1981.
Stuchly et al.; Dielectric properties of animal tissues in vivo at radio and microwave frequencies: comparison between species; Phys. Med. Biol.; 27(7); pp. 927-936; Jul. 1982.
Sullivan et al.; Comparison of measured and simulated data in an annular phased array using an inhomogeneous phantom; IEEE Trans on Microwave Theory and Techniques; 40(3); pp. 600-604; Mar. 1992.
Sullivan et al.; The pig as a model for human wound healing; Wound Repair Regen; 9(2); pp. 66-76; Mar. 2001.
Sunaga et al.; Development of a dielectric equivalent gel for better impedance matching for human skin; Bioelectromagnetics; 24; pp. 214-217; Apr. 2003.

Surowiec et al.; Dielectric properties of breast carcinoma ind the surrounding tissues; IEEE Trans on Biomedical Engineering; 35(4); pp. 257-263; Apr. 1988.
Tavernier et al.; Conductivity and dielectric permittivity of dermis and epidermis in nutrient liquid saturation; Engineering in Medicine and Biology Society; 1992 14th Annual Int. Conf of the IEEE; Paris, France; pp. 274-275; Oct. 29-Nov. 1, 1992.
Thermolase Corp.; 510K Pre-Market Notification (No. K950019) and Product User Manual ThermoLase Model LT100 Q-Switched Nd: YAG, Laser Hair Removal System, Jan. 3, 1995.
Trembly et al.; Combined Microwave Heating and Surface Cooling of the Cornea; IEEE Transactions on Biomedical Engineering; vol. 38; No. 1; pp. 85-91; Jan. 1991.
Urolgix, Inc.; Cooled Thermotherapy + Prostiva RF = Durability + Versatility; 1 pg.; printed Jun. 18, 2012 from website (http://www.urologix.com/).
Uzunoglu et al.; A 432-MHz Local Hyperthermia System Using an Indirectly Cooled, Water-Loaded Waveguide Applicator; IEEE Trans. on Microwave Theory and Techniques; vol. 35, No. 2; pp. 106-111; Feb. 1987.
Valleylab; Cool-tip} RF Ablation System; (http://www.cool-tiprf.com/physics.html) accessed Jun. 24, 2008.
Van Rhoon et al.; A 433 MHz Lucite Cone Waveguide Applicator for Superficial Hyperthermia; International Journal of Hyperthermia; vol. 14, No. 1; pp. 13-27; Jan.-Feb. 1998.
Vander Vorst et al.; RF/microwave interaction with biological tissues; Hoboken, NJ; John Wiley & Sons, Inc.; pp. 264-305; Jan. 2006.
Vardaxis et al.; Confocal laser scanning microscopy of porcine skin: Implications for human wound healing studies; J Anat; 190(04); pp. 601-611; May 1997.
Virga et al.; Low-profile enhanced-bandwidth PIFA antennas for wireless communications packaging; IEEE Trans on Microwave Theory and Techniques; 45(10); pp. 1879-1888; Oct. 1997.
Vrba, et al.; Evanescent-Mode Applicators (EMA) for Superficial and Subcutaneous Hyperthermia; IEEE Trans. on Biomedical Engineering; vol. 40; No. 5; pp. 397-407; May 1993.
Warty et al.; Characterization of implantable antennas for intracranial pressure monitoring: reflection by and transmission through a scalp phantom; IEEE Trans on Mircrowave Theory and Techniques; 56(10); pp. 2366-2376; Oct. 2008.
Weiss et al.; Monopolar radiofrequency facial tightening: a retrospective analysis of efficacy and safety in over 600 treatments; J Drugs Dermatol; 5(8); pp. 707-712; Sep. 2006.
Wikipedia; Bayonet mount; 6 pages; Dec. 18, 2014; retrieved from the internet (www.http://en.wikipedia.org/wiki/Bayonet mount).
Wikipedia; ISM band; 5 pages; printed Jul. 22, 2014 from website (http://en.wikipedia.org/wiki/ISM_band).
Wollina et al.; Tumescent suction curettage versus minimal skin resection with subcutaneous curettage of sweat glands in axillary hyperhidrosis; Dermatol Surg; 34(5); pp. 709-716; May 2008.
Wong, G.; miraDry system: technology to help treat excessive underarm sweat; 1 pg.; Feb. 10, 2011; printed on Jun. 18, 2012 from website (http://www.ubergizmo.com/2011/02/miradry-system-treat-excessive-underarm-sweat/).
Wonnell et al.; Evaluation of microwave and radio frequency catheter ablation in a myocardium-equivalent phantom model; IEEE Trans. on Biomedical engineering; 39(10); pp. 1086-1095; Oct. 1992.
Wright et al.; Hepatic microwave ablation with multiple antennae results in synergistically larger zones of coagulation necrosis; Ann. Surg. Oncol.; 10(3); pp. 275-283; Apr. 2003.
Yang et al.; A Floating Sleeve Antenna Yields Localized Hepatic Microwave Ablation; IEEE Transactions on Biomedical Engineering; 53(3); pp. 533-537; Mar. 2006.
Zelickson et al.; Histological and ultrastructural evaluation of the effects of a radiofrequency-based nonablative dermal remodeling device; Arch Dermatol; 140; pp. 204-209; Feb. 2004.
Zelickson et al.; Ultrastructural effects of an infrared handpiece on forehead and abdominal skin; Dermatol Surg; 32(7); pp. 897-901; Jul. 2006.
Zhou et al.; Resection of Meningiomas with Implantable Microwave Coagualation; Bioelectromagnetics; vol. 17; No. 2; pp. 85-88;

(56) References Cited

OTHER PUBLICATIONS (year of publication is sufficiently earlier than the effective U.S. filing date and any foreign priority date) 1996.

Kim et al.; U.S. Appl. No. 14/907,145 entitled "Apparatus and methods for the treatment of tissue using microwave energy," filed Jan. 22, 2016.

Johnson et al.; U.S. Appl. No. 15/667,461 entitled "Systems, apparatus, methods and procedures for the non-invasive treatment of tissue using microwave energy," filed Aug. 2, 2017.

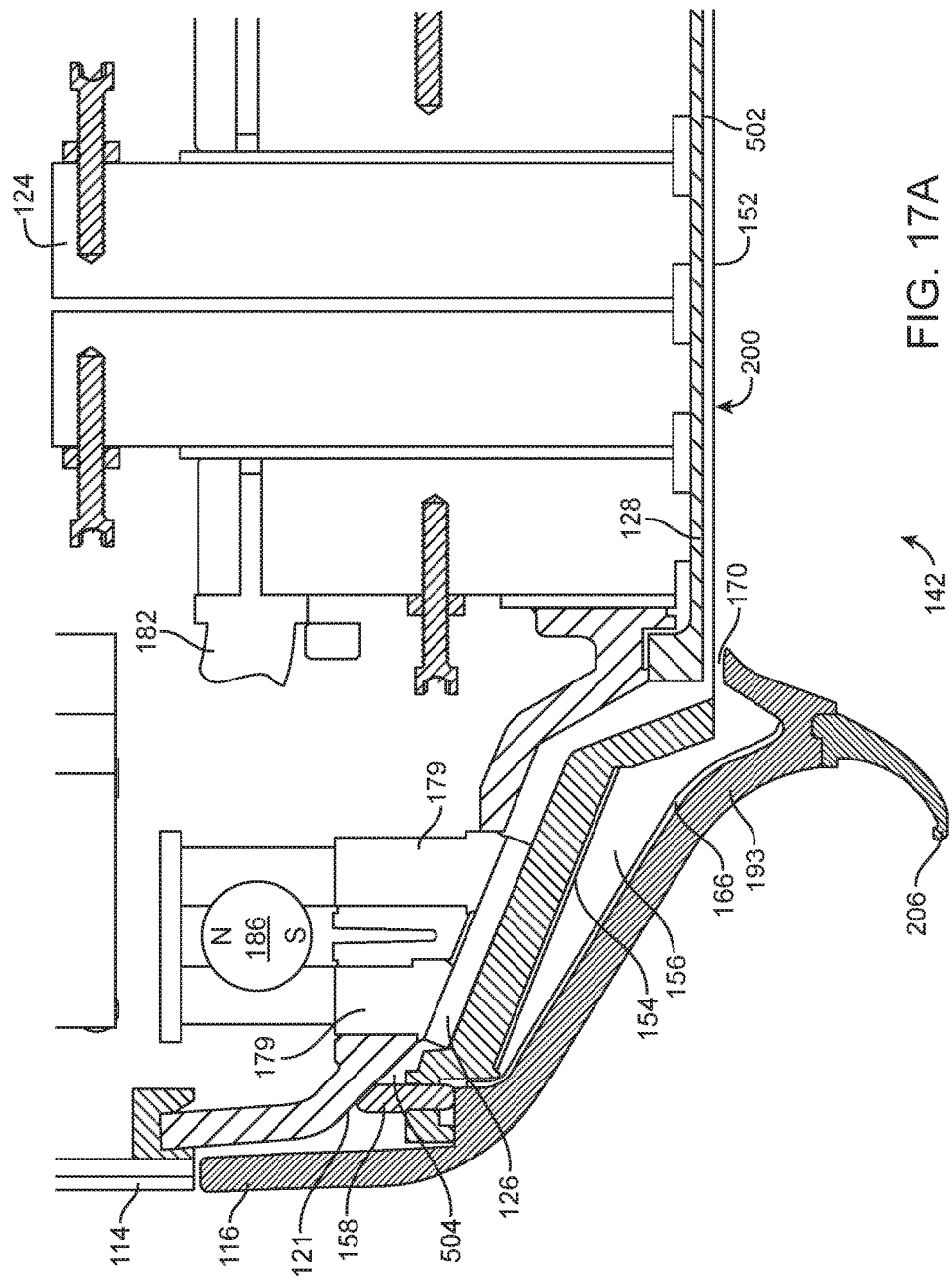

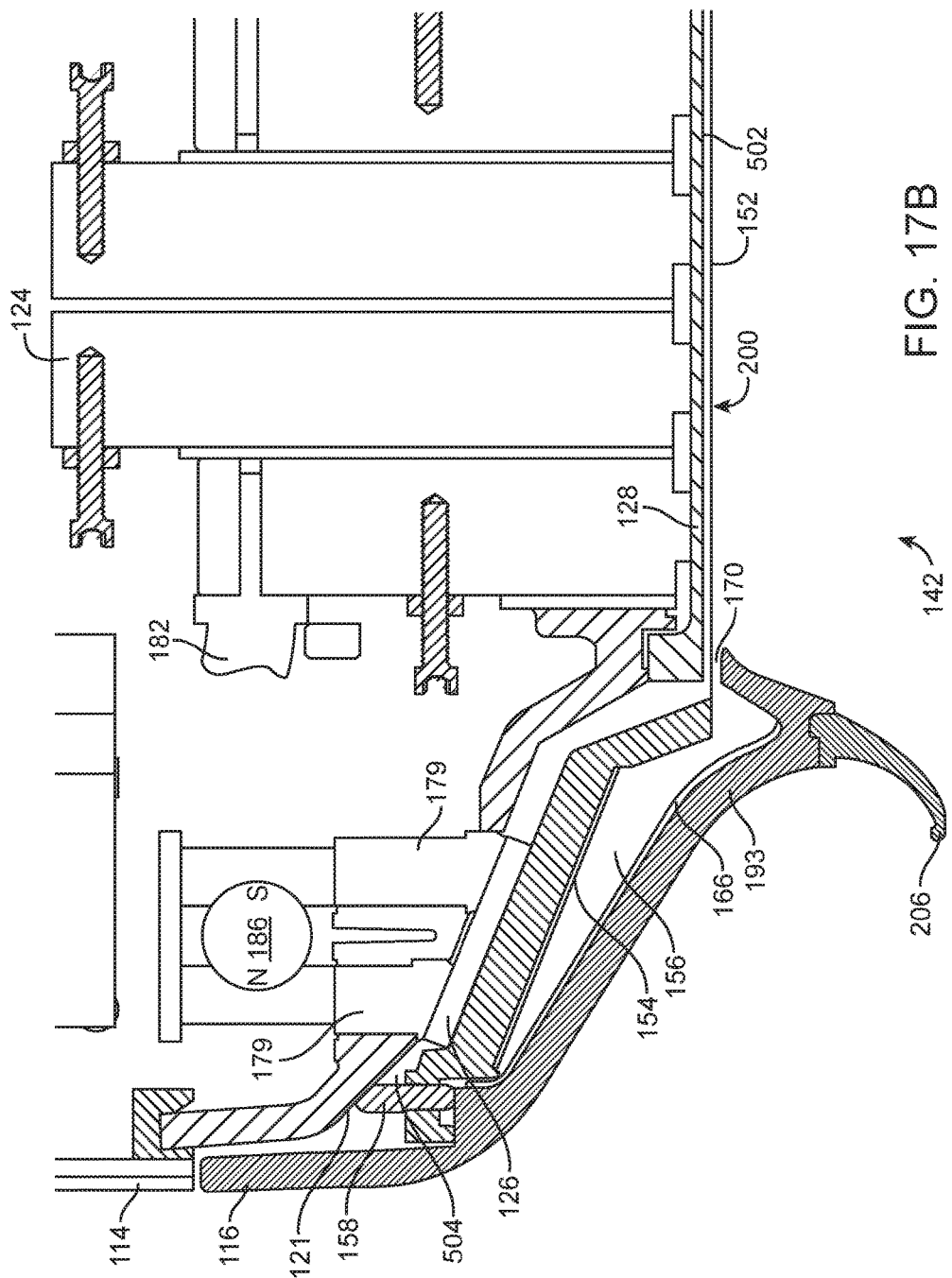

APPLICATOR AND TISSUE INTERFACE MODULE FOR DERMATOLOGICAL DEVICE

CROSS REFERENCE TO RELATED APPLICATIONS

This application is a division of U.S. application Ser. No. 13/563,656, filed Jul. 31, 2012, now U.S. Pat. No. 9,314,301, which claims the benefit under 35 U.S.C. § 119 of U.S. Provisional Patent Application No. 61/513,834, filed Aug. 1, 2011, titled "Applicator and Consumable for Dermatological Device"; U.S. Provisional Patent Application No. 61/555,410, filed Nov. 3, 2011, titled "Applicator and Tissue Interface Module for Dermatological Device"; U.S. Provisional Patent Application No. 61/673,697, filed Jul. 19, 2012, titled "Applicator and Tissue Interface Module for Dermatological Device"; and U.S. Provisional Patent Application No. 61/676,833, filed Jul. 27, 2012, titled "Applicator And Tissue Interface Module For Dermatological Device," the disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to application of energy to tissue. More specifically, this disclosure relates to application of energy to tissue to treat conditions of the skin, epidermis, dermis and hypodermis.

BACKGROUND

Hyperhidrosis or excessive sweating is a common disorder which can result in excessive underarm, facial, or foot sweating. Excessive sweating may cause physical side-effects, including dehydration and infections, as well as emotional side-effects such as embarrassment. Many forms of treatment of hyperhidrosis are currently known, including medications, antiperspirants, botulinum toxins, and ablation therapy.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 17A is a side cutaway view of a portion of an applicator and a portion of tissue interface module with a magnet in a first position.

FIG. 17B is a side cutaway view of a portion of an applicator and a portion of tissue interface module with a magnet in a second position.

DETAILED DESCRIPTION

Figure 1:
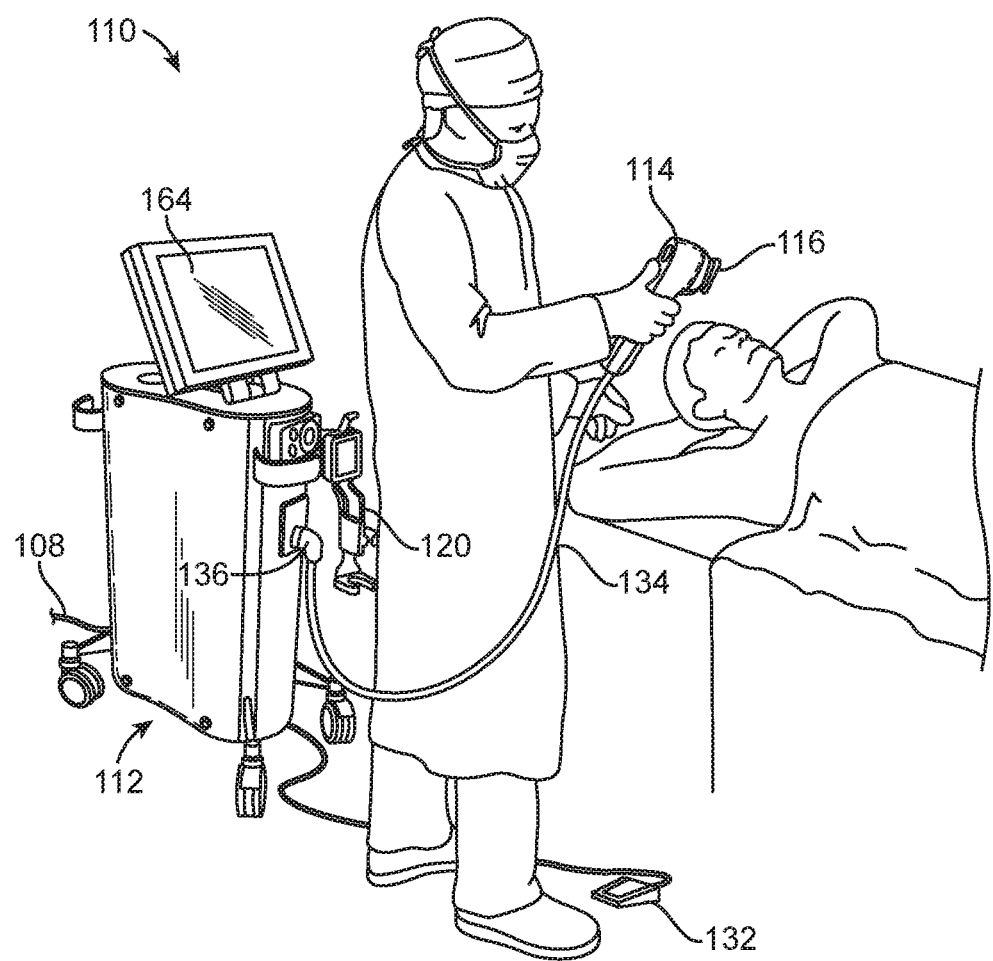
FIG. 1 illustrates a physician holding an applicator and a patient positioned to receive treatment.

FIG. 1 illustrates a Physician treating a patient with energy delivery system 110 (which may be referred to herein as system 110). Energy delivery system 110 may include a console 112, applicator 114 and tissue interface module 116. Console 112 may be referred to herein as generator 112. Applicator 114 may be referred to herein as hand piece or handpiece 114. Tissue interface module 116 may also be referred to as consumable 116, disposable 116, tissue interface 116, applicator tissue interface 116, module 116 or bioTip 116. Console 112 may include a display 164, power cord 108, holster 120 and foot pedal switch 132. Display 164 may be used to show a graphical user interface to guide the physician through treatment steps, such graphical user interface may include, for example, a color map of treatment temperatures, a placement count indicator and a placement positioning arrow. Applicator 114 may include cable assembly 134 and multifunction connector 136. Energy delivery system 110 may be configured to deliver energy to tissue, including skin tissue. In some embodiments, energy delivery system 110 is configured to deliver microwave energy to the skin of the patient to treat a condition of the skin, such as, for example, hyperhidrosis, excessive sweating, bromhidrosis, cellulite, fat, wrinkles, acne, unwanted hair or other dermatological conditions.

When system 110 is assembled, applicator 114 may be connected to console 112 via multifunction connector 136. Console 112 may be configured to generate energy (e.g., microwave energy) at a frequency of, for example, approximately 5.8 gigahertz. Console 112 may be configured to generate energy (e.g., microwave energy) at a frequency of, for example, between approximately 5.3 gigahertz and 6.3 gigahertz or between approximately 5.0 gigahertz and 6.5 gigahertz. In some embodiments, applicator 114 may be connected to console 112 with, for example, a microwave cable, a tensile cord, a USB cable, coolant tubing and vacuum tubing. Applicator 114 may also be connected to a tissue interface module 116. These elements may be included in cable assembly 134. A foot pedal switch 132 may be connected to console 112 to control one or more of the functions of console 112, including the transmission of energy to applicator 114 or, alternatively, switches or buttons on applicator 114 may be used to control console 112.

In some embodiments, console 112 may also include a vacuum source, a cooling fluid source, (e.g., a chiller), a cooling fluid pump, an amplifier, a microwave generator, and control circuitry. These features of console 112 are internal to the console and are used to generate vacuum pressure, cooling fluid and microwave energy which may be transmitted through multifunction connector 136 and cable assembly 134 to applicator 114.

Figure 2:
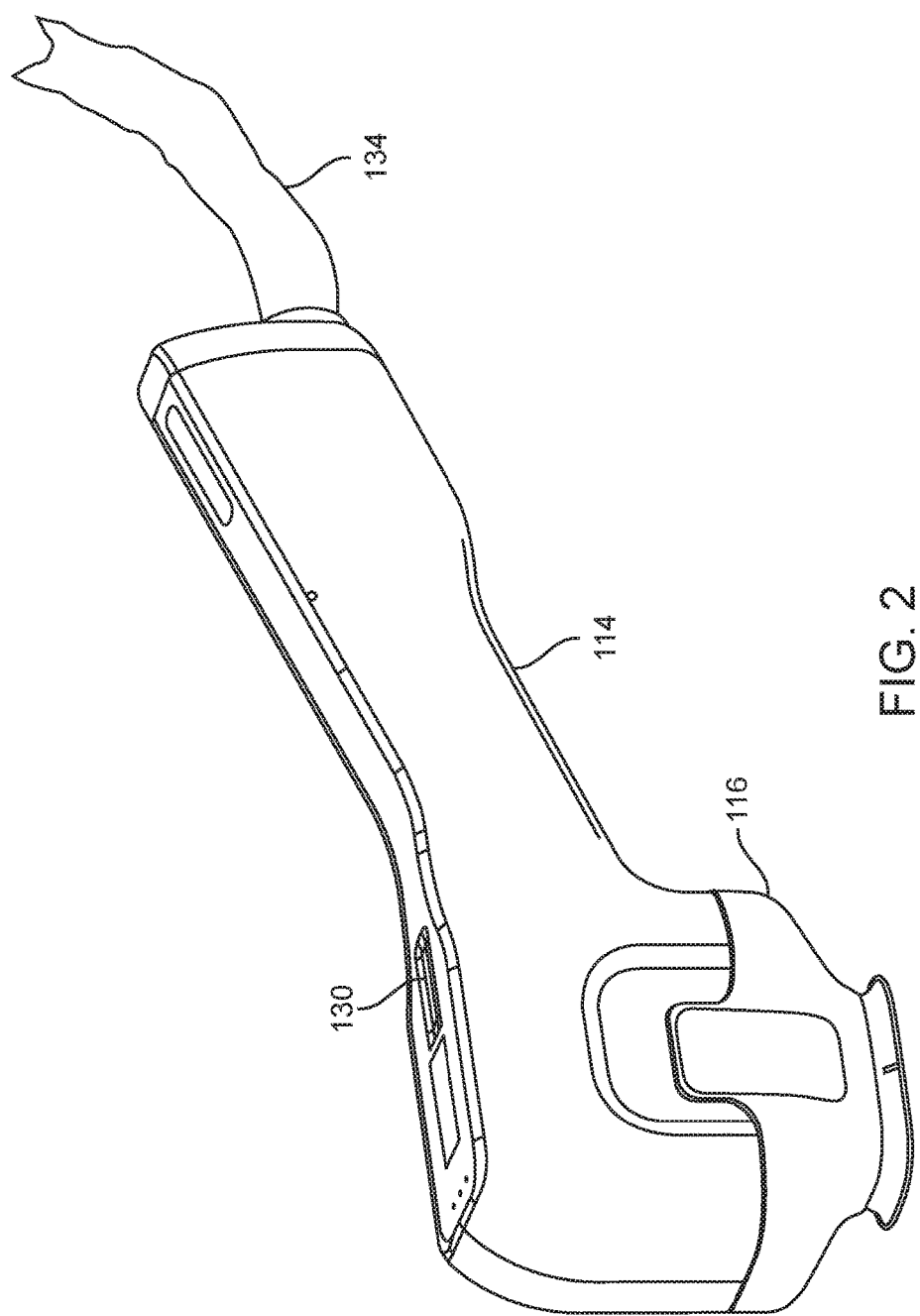
FIG. 2 shows a perspective view of a tissue interface module attached to an applicator.

FIG. 2 shows a perspective view of applicator 114 with tissue interface module 116 attached to a distal end of applicator 114. Cable assembly 134 is shown extending from a proximal portion of applicator 114. Applicator switch 130 may be disposed on a surface of applicator 114 and may be used to control the application of treatment energy from applicator 114. Applicator 114 may also include main control circuitry adapted to control LED indicators, an antenna switch, and applicator switch 130. In some embodiments, the main control circuitry may be designed to receive signals indicative of the direct or reflected power measured at each antenna in applicator 114.

Figure 3:
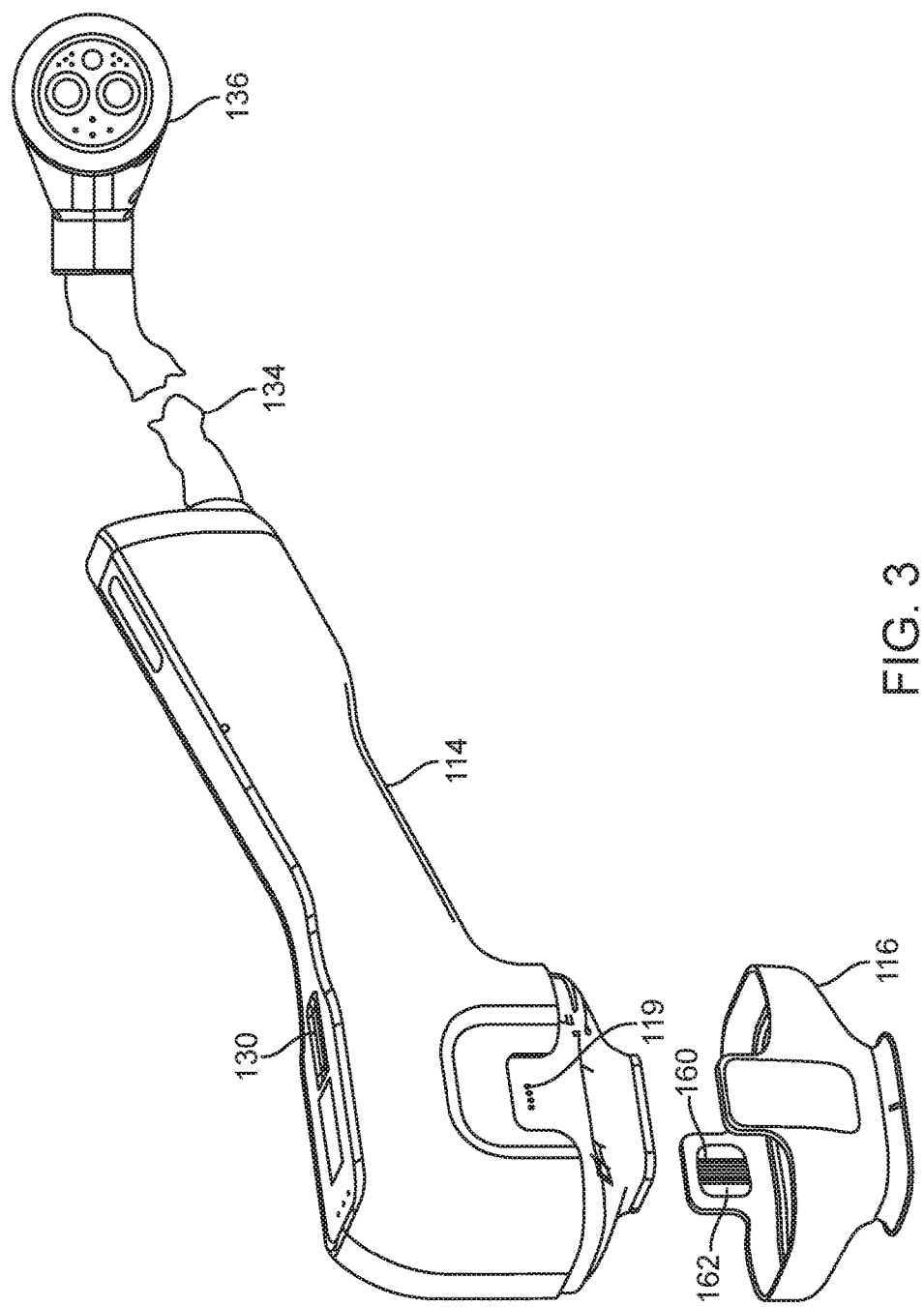
FIG. 3 illustrates a perspective view of a tissue interface module detached from an applicator.

FIG. 3 shows a perspective view of applicator 114 with tissue interface module 116 detached from applicator 114. Removal of tissue interface module 116 reveals electrical contacts 119, which are configured to engage electrical contacts 160 (electrical contacts 160 may be formed by conductive traces on a suitable substrate) and printed circuit board 162. Electrical contacts 160 and traces on printed circuit board 162 may be positioned on one or both sides of tissue interface module 116. Electrical contacts 160 and associated circuitry may be used to, for example, detect the presence of tissue interface module 116 as it is being positioned on applicator 114 or to detect proper alignment of tissue interface module 116 when tissue interface module 116 is properly attached to applicator 114. A security chip may also be included on printed circuit board 162, along with electrostatic discharge (ESD) protection such as, for example, an ESD diode. An integrated circuit 163 (see FIGS. 8-10) may also be included to, for example, assist in detecting the presence and/or proper alignment of tissue interface module 116. In some embodiments, printed circuit board 162 and integrated circuit 163 may be used to detect re-use of a previously used tissue interface module 116. Such information may be used to, for example, notify the user that a new tissue interface module should be used or prevent the re-use of a previously used tissue interface module, which may be contaminated with, for example, biological fluids from a previous patient. Applicator 114 may further include applicator switch 130. FIG. 3 also shows an end view of a multifunction connector 136 disposed at the proximal end of cable assembly 134 for attachment of applicator 114 to console 112 of FIG. 1.

Figure 4:
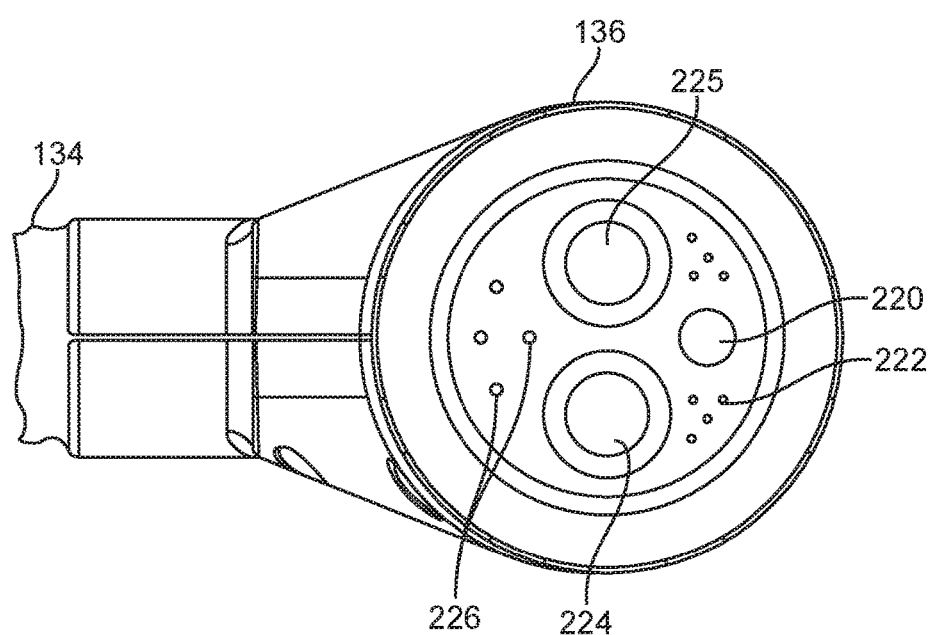
FIG. 4 shows an end view of a multifunction connector.

FIG. 4 shows an end view of multifunction connector 136 and cable assembly 134. In FIG. 4, multifunction connector 136 includes cooling fluid connector 224, cooling fluid return connector 225, microwave connector 220, electronic connectors 222 and vacuum connectors 226. Multifunction connector 136 and cable assembly 134 provide a functional connection between console 112 and applicator 114 (see, for example FIG. 1), allowing applicator 114 to receive microwave energy, data, electrical energy, cooling fluid, and vacuum for treatment procedures and to transmit data back to console 112.

Figure 5:
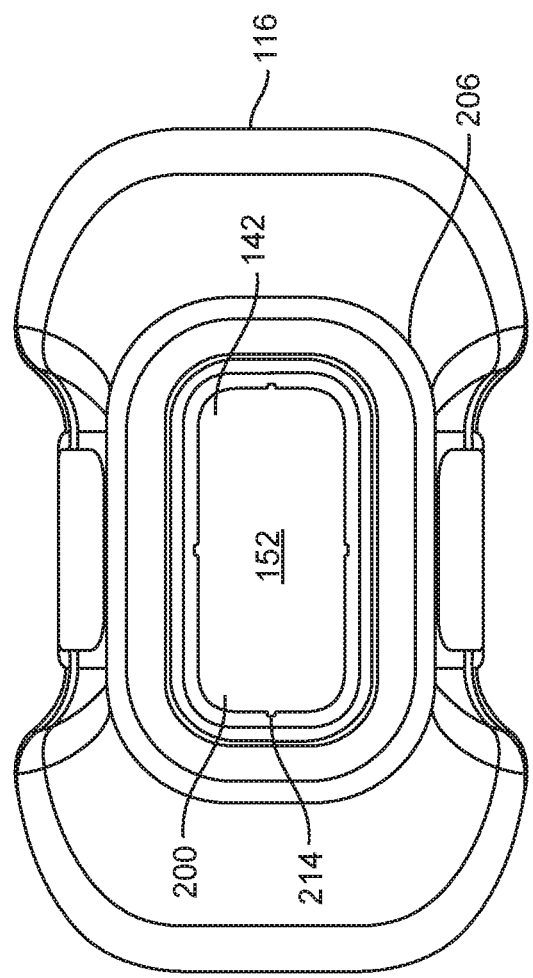
FIG. 5 illustrates an end view of a tissue interface module.

FIG. 5 illustrates an end view of tissue interface module 116 as viewed from the side of tissue interface module 116 that contacts tissue. Tissue interface module 116 may include a tissue acquisition chamber 142 having a tissue interface surface 200, a bio-barrier 152, vacuum notches 214, and skirt 206. In some embodiments of the invention, tissue interface surface 200 may be, for example, a distal surface of bio-barrier 152. In some embodiments of the invention, skirt 206 may not be used or may be modified to facilitate the acquisition of tissue. Tissue acquisition chamber 142 may be sized to facilitate tissue acquisition in the treatment region of the patient. Tissue acquisition chamber 142 may be sized to prevent elements of tissue interface module 116 from interfering with energy radiated from applicator 114. In some embodiments, tissue acquisition chamber 142 may be sized to be approximately 1.54 inches long by 0.7 inches wide, having a depth of approximately 0.255 inches to 0.295 inches. Tissue acquisition chamber 142 may be sized and configured such that the walls of tissue acquisition chamber 142 are outside of the outer edge of antenna array 124 (see, for example FIG. 21). Tissue acquisition chamber 142 may include corners having a radius of approximately 0.1875 inches at a distal end thereof. Tissue acquisition chamber 142 may include corners having a radius of approximately 0.29 inches at a distal end thereof. In some embodiments, these measurements may vary by, for example, up to plus or minus twenty percent. Tissue acquisition chamber 142 is used to properly position tissue in tissue interface module 116 and to properly position such tissue adjacent the distal end of applicator 114.

Skirt 206 may be made from, for example, a compliant medical grade plastic (e.g., a thermal plastic elastomer) such as, for example, urethane, or alternatively silicone, natural or synthetic rubber, elastomeric material, urethane foam with silicone, compliant plastic or a rubber seal coating. A suitable skirt 206 may have a height of between 0.15" and 0.40" and more specifically, approximately 0.25" above tissue acquisition chamber 142 when skirt 206 is not compressed. In some embodiments, skirt 206 may have a durometer (hardness) of approximately 60 on the Shore A scale, or between 40 and 60, or between 20 and 80 on the Shore A scale. In one embodiment, skirt 206 may include inner walls having an average angle of approximately 53 degrees when not compressed. In one embodiment, skirt 206 may include inner walls having an average angle of approximately 49 degrees when not compressed. In some embodiments, these measurements may vary by, for example, up to plus or minus twenty percent. In some embodiments, skirt 206 may be clear or see-through to assist the physician in properly positioning applicator 114 with the tissue to be treated, by, for example, aligning skirt 206 with temporary markings on the patient's skin.

Figure 6:
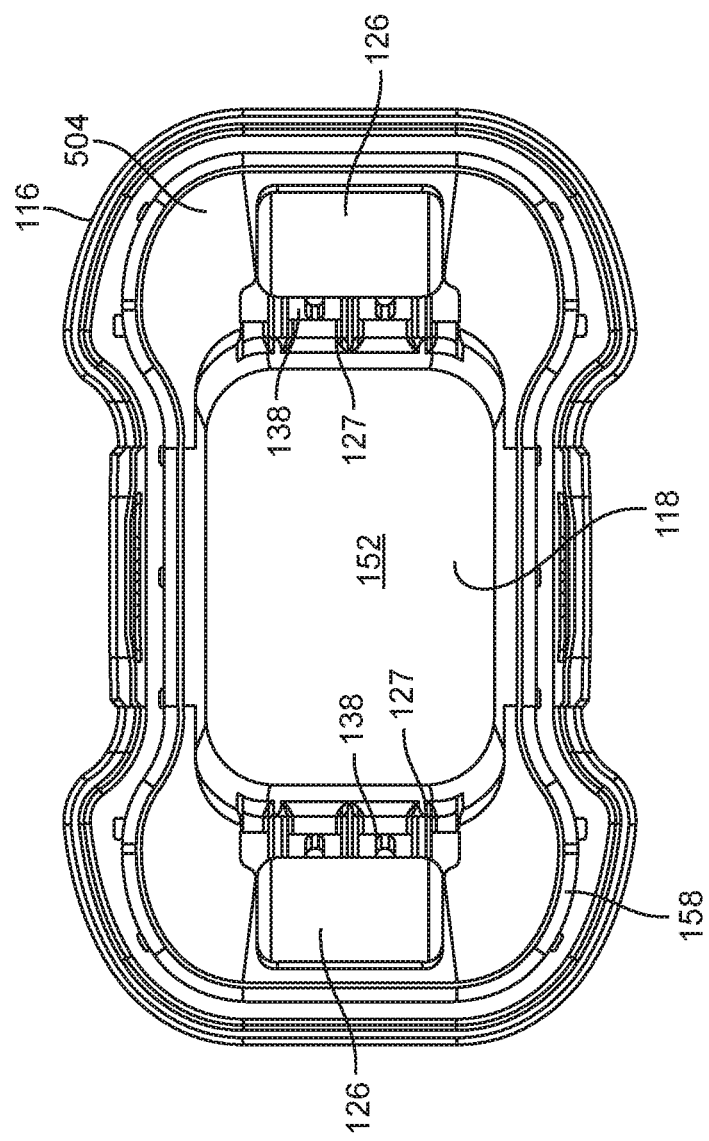
FIG. 6 is a top view of a tissue interface module.

FIG. 6 is a top view of tissue interface module 116 from the proximal (non-treatment/applicator interface) side of tissue interface module 116 which is configured to attach to an applicator 114, such as, for example, the applicator illustrated in FIGS. 1-3. In FIG. 6, tissue interface module 116 includes bio-barrier 152, applicator chamber 118, attachment mechanism 126, vacuum channels 138, attachment supports 127, and gasket 158. Gasket 158 may be referred to as a consumable gasket 158. Attachment mechanism 126 may be, for example a magnet, a ferromagnetic plate or other ferromagnetic element and may be referred to as a latch plate or consumable latch plate. Vacuum channels 138 may be positioned at a proximal end of a tissue chamber vacuum path. Applicator chamber 118 is adapted to receive and connect to a distal end of applicator 114. In embodiments of the invention, applicator 114 may include, for example, a microwave antenna, a cooling element or cooling plate, and at least one vacuum inlet. Gasket 158 may provide a substantially air tight (e.g., hermetic) seal against applicator 114 when a distal end of applicator 114 is positioned in applicator chamber 118. In embodiments of the invention, the seal provided by gasket 158 may allow a limited amount of air to pass, provided that such leaks do not adversely affect the vacuum balance described herein or otherwise adversely affect the function of the tissue interface module. In some embodiments, a proximal end of gasket 158 may form a sealing member. Gasket 158 may have a hardness durometer of, for example, between 20A and 80A. Gasket 158 may also have a thickness of approximately 1/16th of an inch in some embodiments. In some embodiments, these measurements may vary by, for example, up to plus or minus twenty percent. The opening formed by gasket 158 at the proximal end of applicator chamber 118 may act as a vacuum interface 504 (which may also be referred to as a vacuum outlet, vacuum outlet opening, vacuum channel or vacuum channel opening) when tissue interface module 116 is positioned on applicator 114, air is channeled to flow out from applicator chamber 118 and into vacuum inlets 174 on applicator 114. Positioning vacuum interface 504 at a proximal end of tissue interface module 116, in applicator chamber 118, may be particularly beneficial as it helps to maintain the pressure in applicator chamber 118 ($P_{app}$) at a pressure less than the pressure in the tissue acquisition chamber 142 ($P_{tiss}$), which helps to ensure that bio-barrier 152 will maintain its position against cooling plate 128. This position may be maintained even in the presence of leaks, such as, for example, leaks at the interface between gasket engagement surface 500 and sealing surface 121. This arrangement may be particularly important in preventing the formation of bubbles, voids or deformities in the interface between bio-barrier 152 and applicator tissue treatment surface 502 (which may be, for example, the distal surface of cooling plate 128) thus protecting the patients skin from damage resulting from such bubbles, voids or deformities.

Attachment mechanisms 126 may be positioned on proximal side of tissue interface module 116, such as, for example in applicator chamber 118 and be adapted to facilitate the attachment of module 116 to applicator 114. In some embodiments, attachment mechanism 126 may include mechanical elements on applicator 114 and tissue interface module 116. In some embodiments, attachment mechanisms 126 may include a metal or ferromagnetic plate configured to cooperate with a magnet or magnets on applicator 114. In some embodiments, attachment mechanisms 126 form a completed magnetic circuit with elements of applicator 114, including, for example, magnet 186 and magnetic extenders 179 (see, for example, FIGS. 17A and 17B). Magnet 186 in cooperation with magnetic extenders 179 may form at least a portion of a magnetic clamp adapted to engage and hold tissue interface module 116 in position during treatment of a patient. Magnet 186 may be, for example, a diametrically magnetized neodymium cylindrical magnet. Attachment mechanism 126 may be, for example, stainless steel plates, ferromagnetic plates, iron plates or steel plates. In some embodiments, attachment mechanisms 126 may be, for example, plates approximately 0.5 inches in width and 1.05 inches in length, with a thickness of approximately 0.63 inches. The size of these plates may, without substantial impact to performance, vary in other embodiments by, for example, plus or minus 20%. However, thicker and/or larger magnetic plates may increase the mass of the plate without improving the magnetic holding force, having the potentially undesirable effect of making vacuum leaks more likely or making tissue interface module 116 more likely to fall or be knocked off applicator 114. Thinner and/or smaller magnetic plates may reduce the magnetic holding force, also having the undesirable effect of making vacuum leaks more likely or making tissue interface module 116 more likely to fall or be knocked off applicator 114. Attachment mechanisms 126 may rest upon attachment supports 127, which keep attachment mechanisms 126 elevated above and prevent attachment mechanisms 126 from restricting the flow of air through vacuum channels 138 and a filter 154 (see, for example, FIG. 9). In some embodiments, attachment supports 127 are adapted to keep attachment mechanisms 126 raised approximately 0.010 inches (or, in some embodiments 0.080 inches) above filter(s) 154, optimizing air flow through vacuum channels 138 without substantially increasing the size of tissue interface module 116. In some embodiments, these measurements may vary by, for example, up to plus or minus twenty percent.

Figure 7:
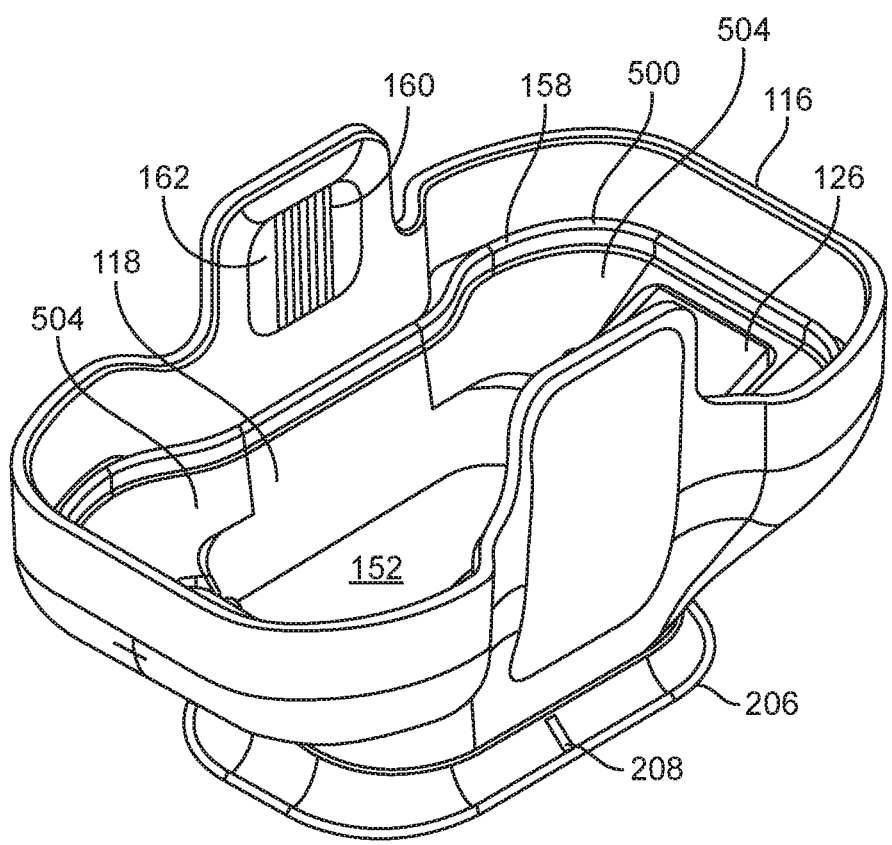
FIG. 7 shows a top perspective view of a tissue interface module.

FIG. 7 is a top perspective view of tissue interface module 116, also showing the proximal (non-treatment) side of tissue interface module 116. FIG. 7 shows applicator chamber 118, which is adapted to receive and properly position applicator 114 with respect to bio-barrier 152 when tissue interface module is 116 attached to applicator 114. When tissue interface module 116 is attached to applicator 114, applicator chamber 118 is adapted to receive a distal end of applicator 114, including, for example, a microwave antenna, a cooling element or cooling plate, and a vacuum inlet. Gasket 158 may provide a seal between tissue interface module 116 and applicator 114 when tissue interface module 116 is attached to applicator 114. Gasket 158 may be held in place by attachment mechanisms 126. Gasket 158 may, in some embodiments, form at least a portion of vacuum interface 504. Gasket 158 may, in some embodiments, surround vacuum interface 504. A gasket engagement surface 500, which, in one embodiment of the invention may be located at a proximal end of gasket 158, may be positioned such that gasket engagement surface 500 contacts sealing surface 121 on applicator 114 as tissue interface module 116 is attached to applicator 114. Tissue interface module 116 may be further designed to engage applicator 114 in a manner which causes gasket engagement surface 500 to deflect as it contacts sealing surface 121. The deflection of gasket engagement surface 500 increases the area of gasket engagement surface 500 in contact with sealing surface 121 and, thus, improving the seal between gasket 158 and applicator 114. As described above, the interior of tissue interface module 116 may further include electrical contacts 160 and printed circuit board 162 configured to, for example, detect the presence of tissue interface module 116 and/or proper alignment of tissue interface module 116 with applicator 114.

Also shown in FIG. 7 is skirt 206, which is configured to facilitate the engagement of tissue, and alignment marker 208 disposed on skirt 206 for aligning tissue interface module 116 with specific portions of the tissue to be treated. During therapy, stamps or markings, including, for example, temporary tattoos may be used to mark patient tissue to appropriately place applicator 114 during treatment. Such stamps may be sized to overlay an area to be treated, (e.g., an axilla). When used on an axilla, a physician may need to select different stamp sizes for different axilla sizes. Stamps are used to mark a number of different treatment points on a patient, including, for example, anesthesia injection sites. Physicians may use the marks created on the patients skin to properly place applicator 114 before and during treatment, using, for example alignment marker 208 on skirt 206.

Figure 8:
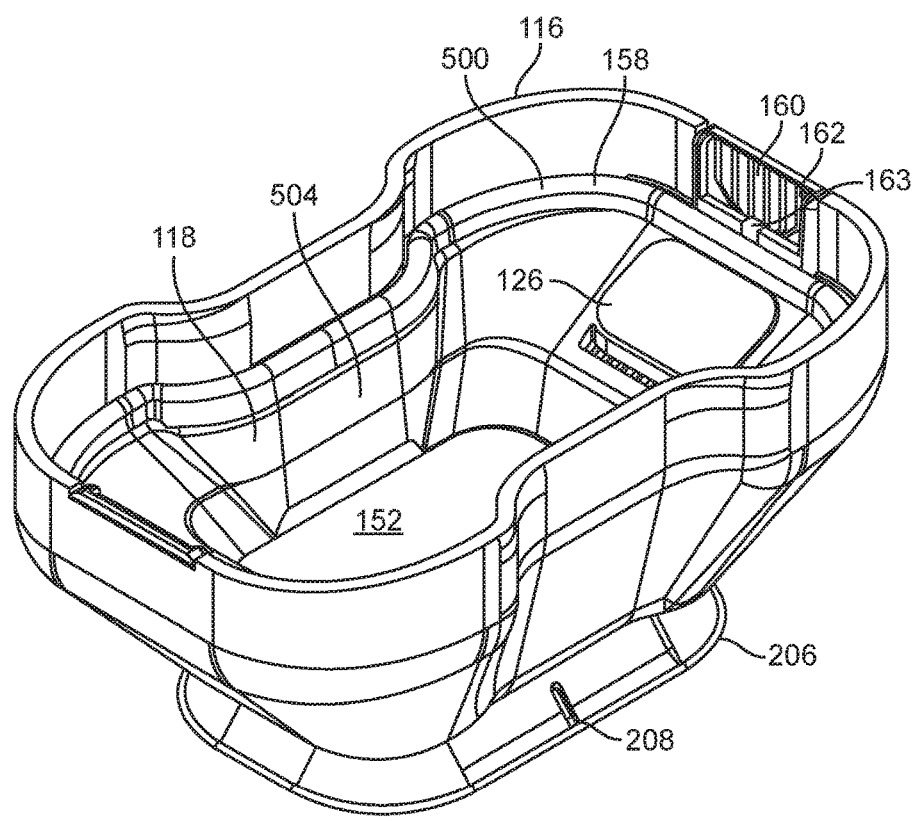
FIG. 8 illustrates a top perspective view of an embodiment of a tissue interface module.

FIG. 8 is a top perspective view of an embodiment of a tissue interface module 116. In this embodiment, printed circuit board 162, electrical contacts 160, and integrated circuit 163 are positioned on the same side(s) of tissue interface module 116 as attachment mechanism 126. As in FIG. 7, skirt 206, alignment marker 208, bio-barrier 152, gasket 158, and applicator chamber 118 may also be seen in this alternative embodiment. FIG. 8 also illustrates attachment mechanism 126, gasket engagement surface 500 and vacuum interface 504.

Figure 9:
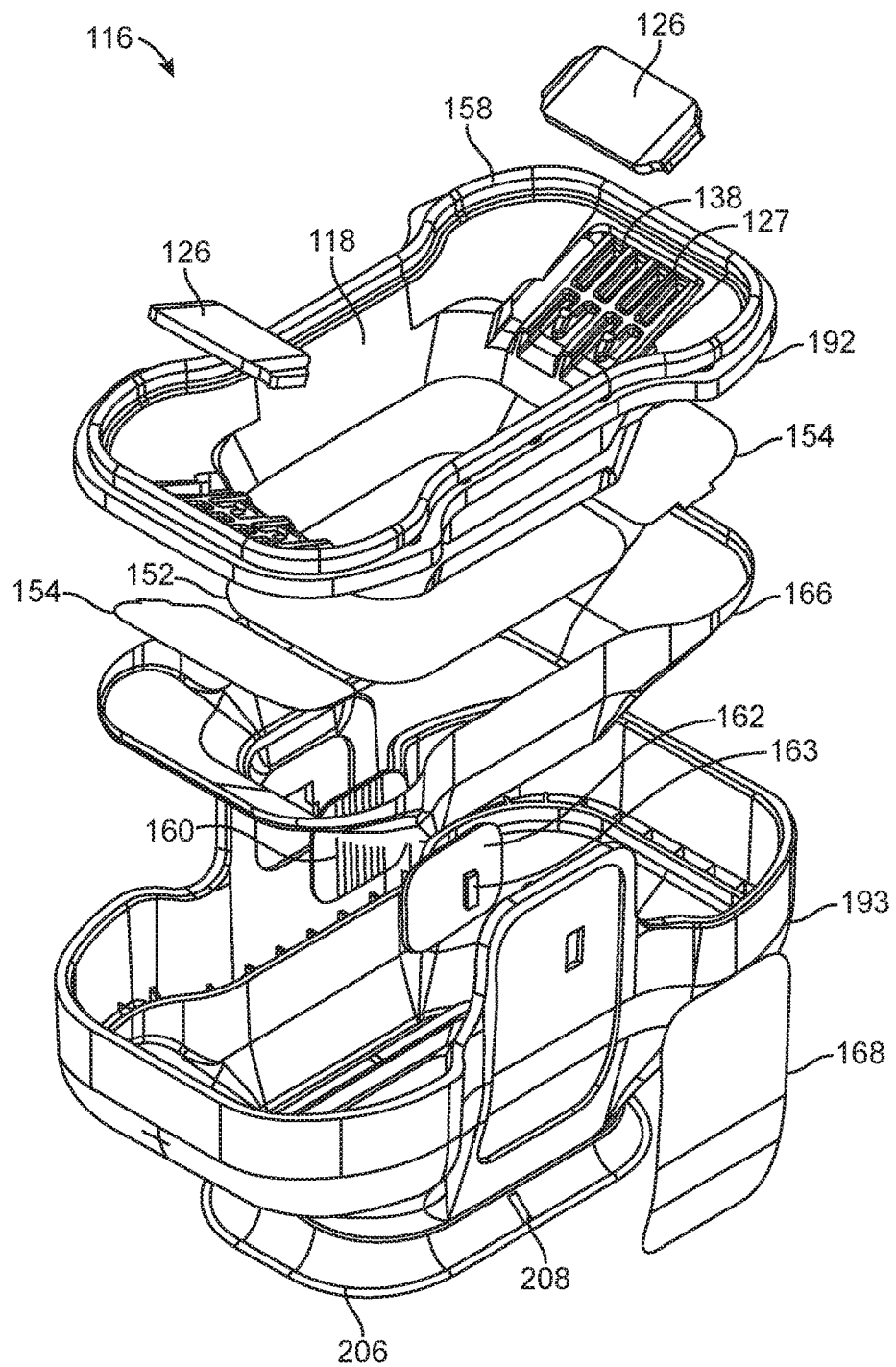
FIG. 9 shows an exploded top perspective view of a tissue interface module.

FIG. 9 is an exploded top perspective view of the tissue interface module 116 of FIGS. 5-7. In FIG. 9, the tissue interface module 116 may include an outer shell 193 and an inner insert 192 and may, in some embodiments also include a reflector 166. Inner insert 192 may include, for example, bio-barrier 152, filters 154, attachment mechanisms 126, gasket 158, vacuum channels 138, attachment supports 127 and applicator chamber 118. Outer shell 193 may include, for example, electrical contacts 160, printed circuit board 162, integrated circuit 163, insulating cover 168, alignment marker 208 and skirt 206.

As shown in FIG. 9, one or more filters 154 may be positioned on either or both sides of bio-barrier 152. Membranes or filters suitable for use as filters 154 may include membranes which are permeable to air but substantially impermeable to biological fluids. Membranes or filters suitable for use as filters 154 may include membranes which provide sufficient resistance to the flow of air to ensure a pressure differential between a first and a second side of filters 154 as air flows through filters 154. When air is removed from applicator 114 through applicator chamber 118 (see, e.g., FIGS. 2-3), filters 154 allow air or gas but not fluid or tissue to pass (see, e.g., FIG. 5). A vacuum in applicator chamber 118 pulls air through filters 154, creating a vacuum in tissue acquisition chamber 142 to pull tissue positioned adjacent tissue acquisition chamber 142 into tissue acquisition chamber 142 and position that tissue against bio-barrier 152 and tissue interface surface 200. Hence the creation of a vacuum in applicator chamber 118 pulls tissue into tissue interface module 116 and positions that tissue for treatment by applicator 114.

Referring still to FIG. 9, reflector 166 may optionally be positioned between inner insert 192 and outer shell 193, or integrated into inner insert 192, outer shell 193, or both. Reflector 166 may include an electrically conductive mesh with openings of a predetermined size. In some embodiments, reflector 166 is configured to isolate stray electromagnetic fields and reflect stray electromagnetic energy back into applicator 114. In some embodiments, reflector 166 is positioned so as to be electrically isolated from applicator 114 and electrically isolated from tissue positioned in tissue acquisition chamber 142. Reflector 166 may be sized and configured to surround at least a portion of and preferably most or all of tissue interface surface 200 when tissue interface module 116 is positioned on applicator 114. Reflector 166 may be sized and configured to surround at least a portion of and preferably most or all of distal surface of cooling plate 128. In some embodiments, reflector 166 may include a metallic mesh material of wire having a diameter of approximately 0.008 inches with wires arranged in a mesh of approximately 30 by 30 wires per inch. In some embodiments, reflector 166 may include a metallic mesh having wires arranged in a mesh of approximately 100 by 100 exch. In some embodiments, these measurements may vary by, for example, up to plus or minus twenty percent.

Figure 10:
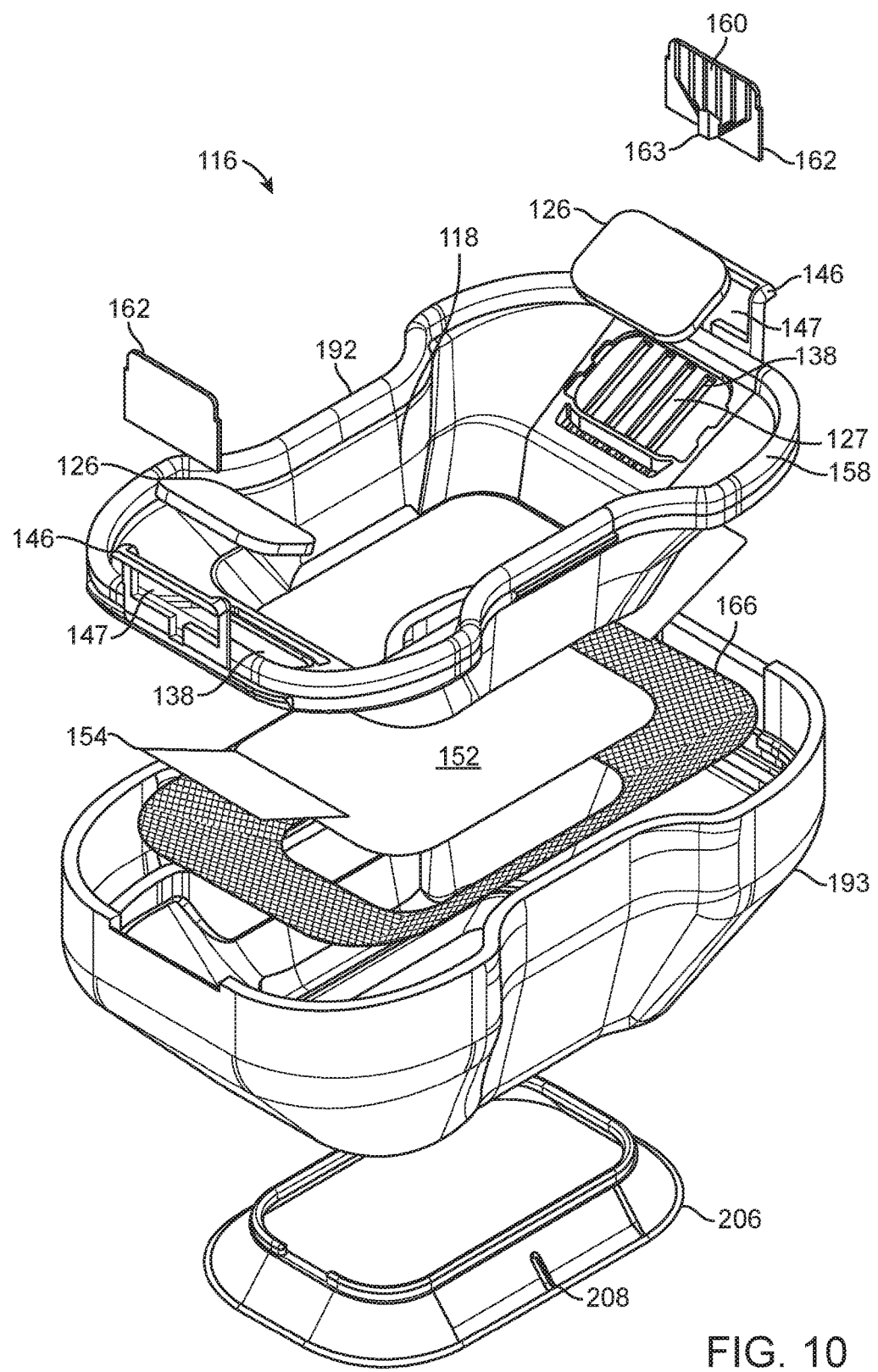
FIG. 10 is an exploded top perspective view of an embodiment of a tissue interface module.

FIG. 10 is an exploded top perspective view of tissue interface module 116 of FIG. 8. In FIG. 10, tissue interface module 116 may include an outer shell 193 and an inner insert 192. Inner insert 192 may include bio-barrier 152, filter(s) 154, attachment mechanisms 126, gasket 158, vacuum channels 138, attachment supports 127, applicator chamber 118, electrical contacts 160, printed circuit board 162, integrated circuit 163, tab member 146, and latch openings 147. Outer shell 193 may include alignment marker 208 and skirt 206. Reflector 166 may optionally be positioned between inner insert 192 and outer shell 193, or integrated into inner insert 192, outer shell 193, or both. The embodiments described herein are particularly advantageous because of the improvements they provide in manufacturability, quality, cost and manufacturing time.

Figure 11:
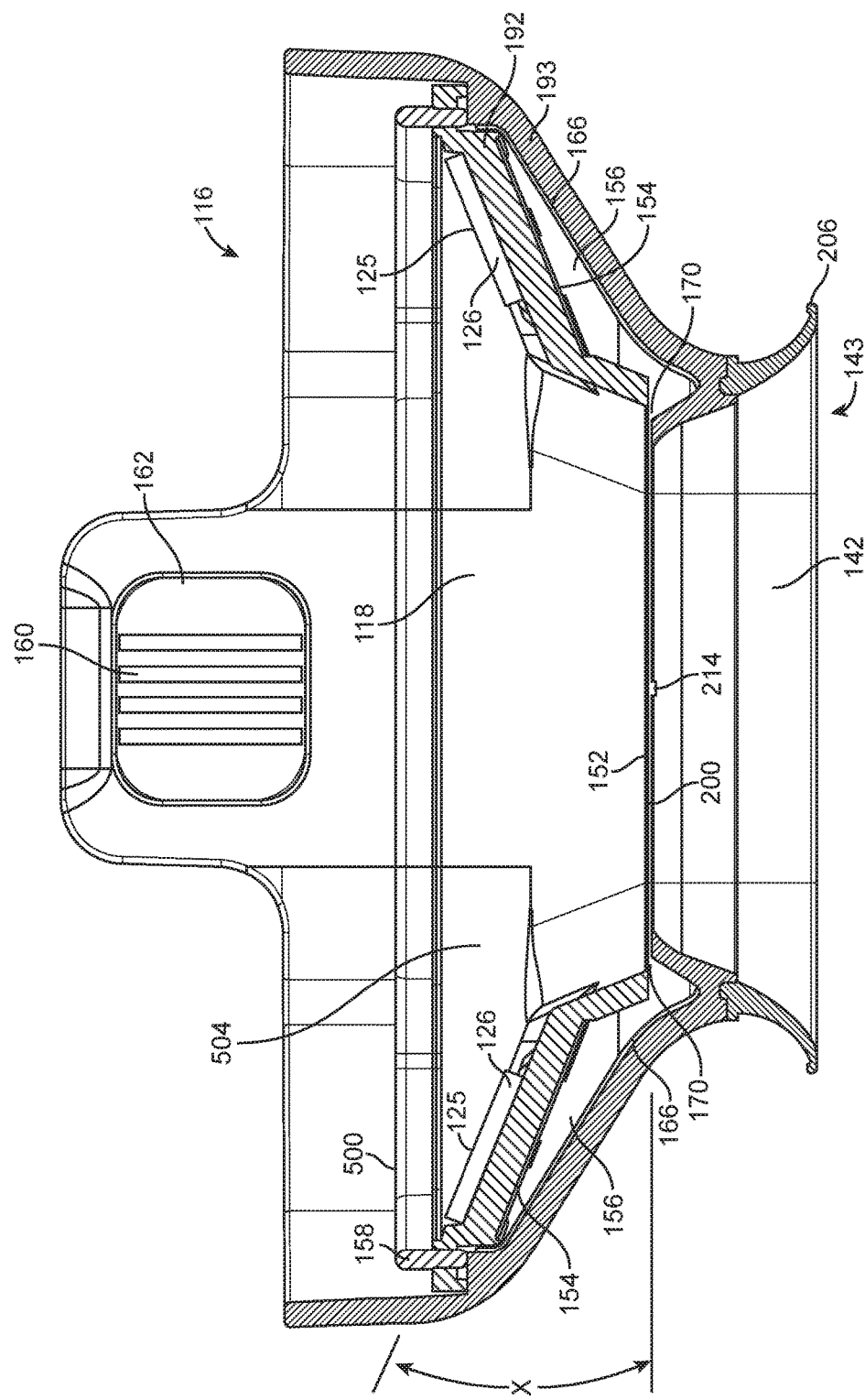
FIG. 11 shows a side cutaway view of a tissue interface module.
Figure 12:
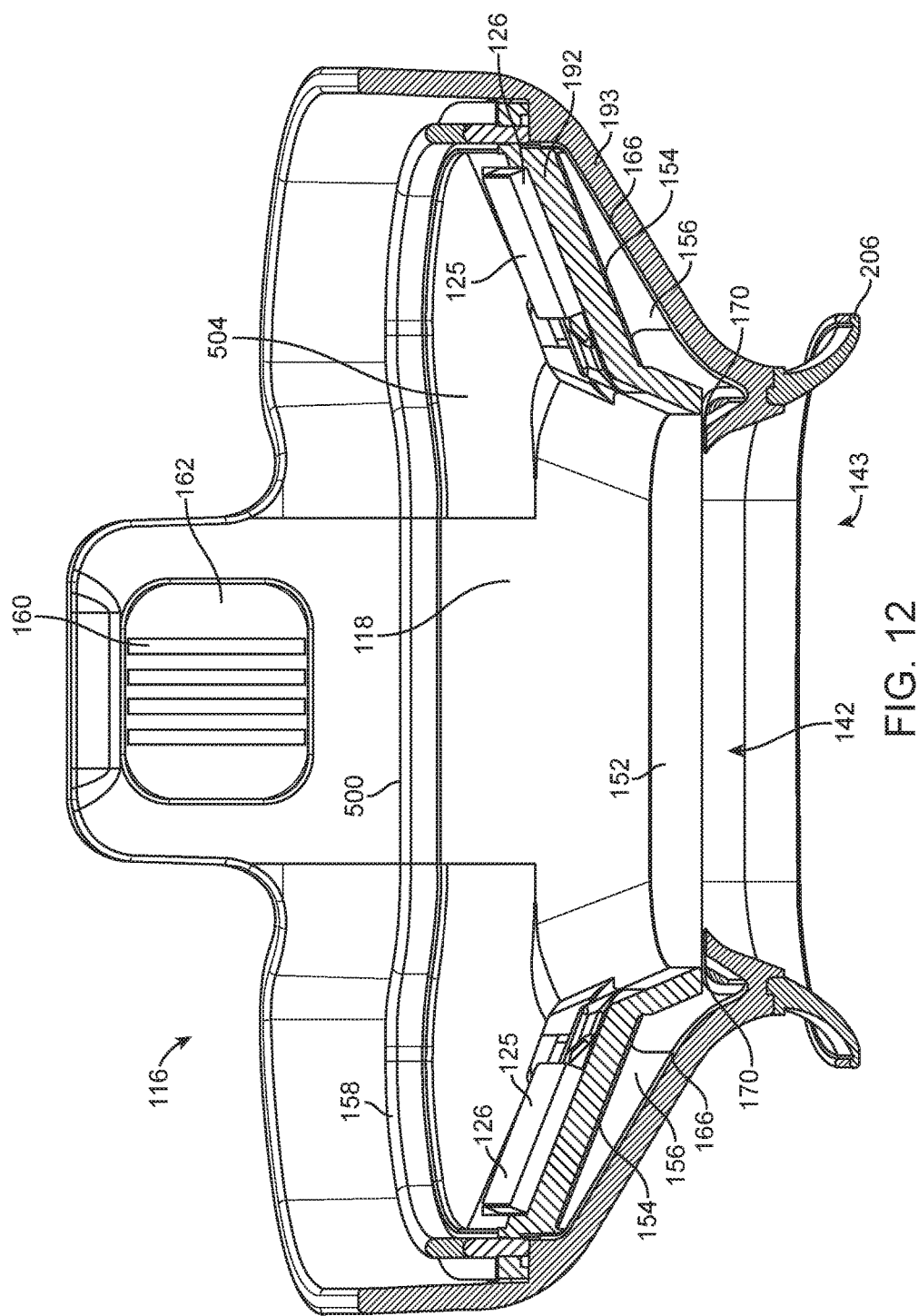
FIG. 12 illustrates a side cutaway perspective view of a tissue interface module.

FIG. 11 illustrates a side cutaway view of a tissue interface module 116 and FIG. 12 shows a side cutaway perspective view of tissue interface module 116. The tissue interface module illustrated in FIGS. 11 and 12 may include many of the features described herein, including tissue acquisition chamber 142, bio-barrier 152, filters 154, applicator chamber 118, electrical contacts 160, printed circuit board 162, attachment mechanism 126, gasket 158, gasket engagement surface 500, inner insert 192, outer shell 193, reflector 166, skirt 206, acquisition chamber opening 143, vacuum notches 214 (not shown in FIG. 12) and tissue interface surface 200 (not shown in FIG. 12). Attachment mechanisms 126 include engagement surface 125, which is configured to engage with cooperative elements on applicator 114 of FIGS. 2 and 3 (e.g., via magnetic attachment). In FIG. 11, engagement surface 125 may form an angle X with a plane formed by bio-barrier 152. Angle X may also be measured as the angle between engagement surface 125 and a plane through or parallel to applicator treatment surface 502 when tissue interface module 116 is positioned on applicator 114 (see, for example, the position of applicator treatment surface 502 FIG. 17A).

As described herein, attachment mechanisms 126 may be disposed on attachment supports 127 of FIG. 6 over vacuum channels 138 of FIGS. 6 and 9. Filters 154 may be positioned on the other side of attachment supports 127 and vacuum channels 138. In addition to the features described above, tissue interface module 116 may further include fluid traps 156 integrated into tissue interface module 116. (Fluid trap 156 may also be referred to as a vacuum trap, vacuum reservoir or integrated fluid trap). Fluid traps 156 may be configured to, for example, trap contaminants such as tissue, bodily fluids or lubricants before such contaminants reach filter 154. In embodiments of the invention, tissue interface module 116 may include at least one expandable aperture 170 (also referred to as a variable flow restrictor or expandable channel) between tissue acquisition chamber 142 and fluid traps 156.

Fluid traps 156 may be configured to, for example, collect blood, sweat, and any other bodily fluids or tissue that may collect within tissue interface module 116 during treatment. Fluid traps 156 may further collect liquids or jells, such as, for example, K-Y jelly, used to facilitate acquisition of tissue. By collecting bodily fluids or tissues in fluid traps 156, tissue interface module 116 keeps filters 154 clear from obstructions that would otherwise interfere with the flow of air through such filters and might interfere with treatment or render treatment impossible. Thus, filters 154 are disposed between, and communicating with, both applicator chamber 118 and tissue acquisition chamber 142. As described above, filters 154 may include openings configured to permit air or gas to pass but prevent liquid from passing through filters 154. In one embodiment, applicator chamber 118 is able to communicate with tissue acquisition chamber 142 via filters 154 and vacuum channels 138. Tissue interface module 116 may further include vacuum interface 504.

Expandable aperture 170 may be included at a proximal end of tissue acquisition chamber 142, and expandable aperture 170 may include, for example, a gap at top of tissue acquisition chamber 142 between a bio-barrier 152 and an interior rim of tissue acquisition chamber 142. Vacuum notches 214 may be included in tissue acquisition chamber 142 proximal to the gap to enhance vacuum acquisition. In some embodiments, one wall (such as, for example, the wall formed by bio-barrier 152) of expandable aperture 170 may be flexible to increase in size and increase airflow when vacuum is applied. A tissue treatment surface 200 of applicator 114 may act to restrict the width of the aperture as it expands. A suitable expandable aperture 170 may be sized to allow air to pass into a vacuum path while preventing tissue from blocking such vacuum path.

Figure 13:
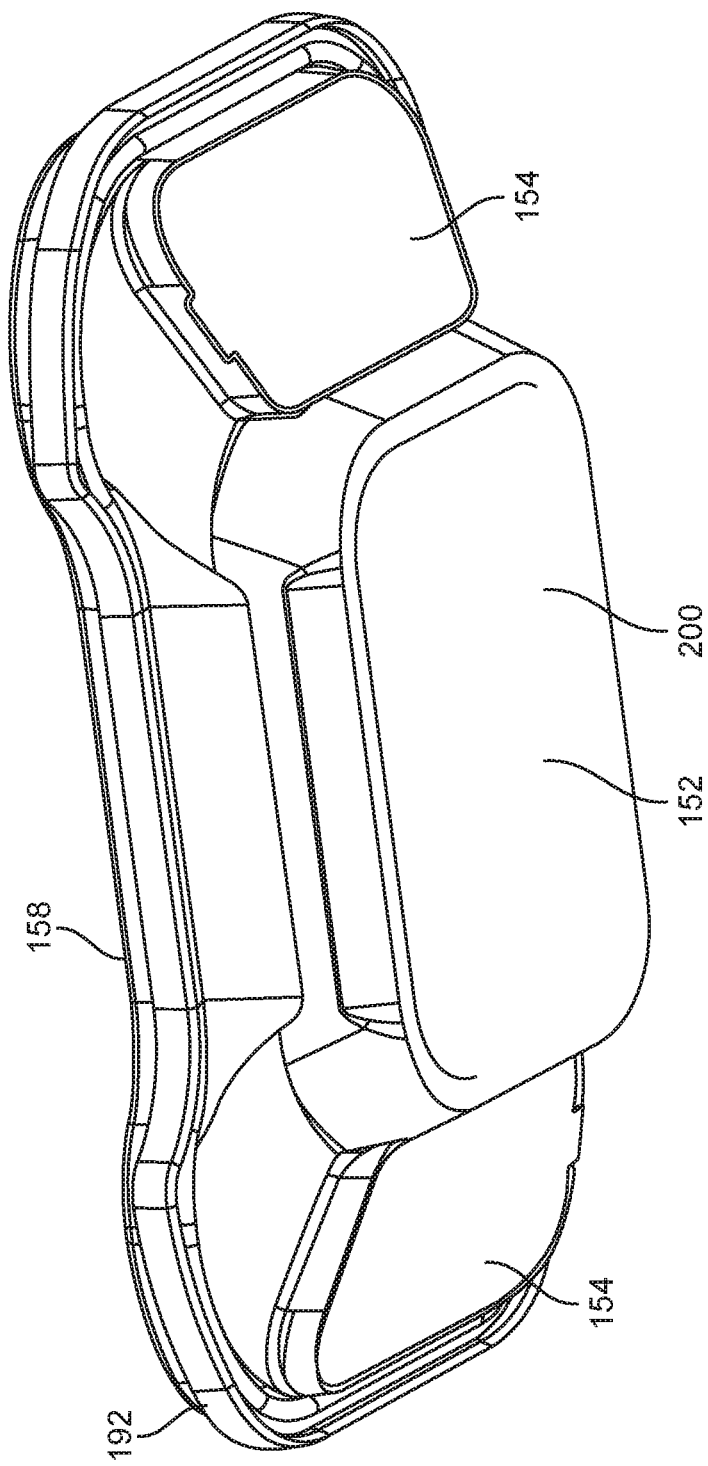
FIG. 13 is a perspective end view of an inner insert assembly from a tissue interface module.

FIG. 13 illustrates a perspective end view of inner insert 192, showing tissue interface surface 200, bio-barrier 152, filters 154, and gasket 158. This view of inner insert 192 shows the portions of filters 154 which interface with and help form fluid traps 156 (see, e.g., FIGS. 11-12). In one embodiment of the invention (with tissue interface module 116 positioned on applicator 114 and tissue positioned adjacent acquisition chamber opening 143) all airflow exchange between applicator chamber 118 and tissue acquisition chamber 142 flows through the interior of tissue interface module 116. In one embodiment of the invention (with tissue interface module 116 positioned on applicator 114 and tissue positioned adjacent acquisition chamber opening 143) all airflow exchanged between applicator chamber 118 and tissue acquisition chamber 142 flows through filters 154. Maximizing the surface area of filters 154 may increase vacuum performance and provide redundancy in case one of filters 154 becomes clogged with, for example, biological tissue, lubricants or bodily fluids. In one embodiment, filters 154 may occupy approximately the same surface area as bio-barrier 152. In other embodiments, a functional portion of bio-barrier 152 may occupy approximately 60% (in some embodiments 50-70%), of the functional surface area of bio-barrier 152, and a functional portion of filters 154 may occupy the remaining 30-50% of the total bio-barrier functional surface area. With respect to bio-barrier 152, the functional area may be the area of bio-barrier 152 which comes into contact with the distal side of cooling plate 128. With respect to filter 154, the functional area may be the area of filter 154 through which air travels as air is pulled from tissue acquisition chamber 142 into applicator chamber 118. In some embodiments of the invention, a combined bio-barrier, including bio-barrier 152 and filters 154 may include a functional area which is approximately fifty to seventy percent composed of bio-barrier 152 and approximately thirty to fifty percent composed of filters 154.

Figure 14:
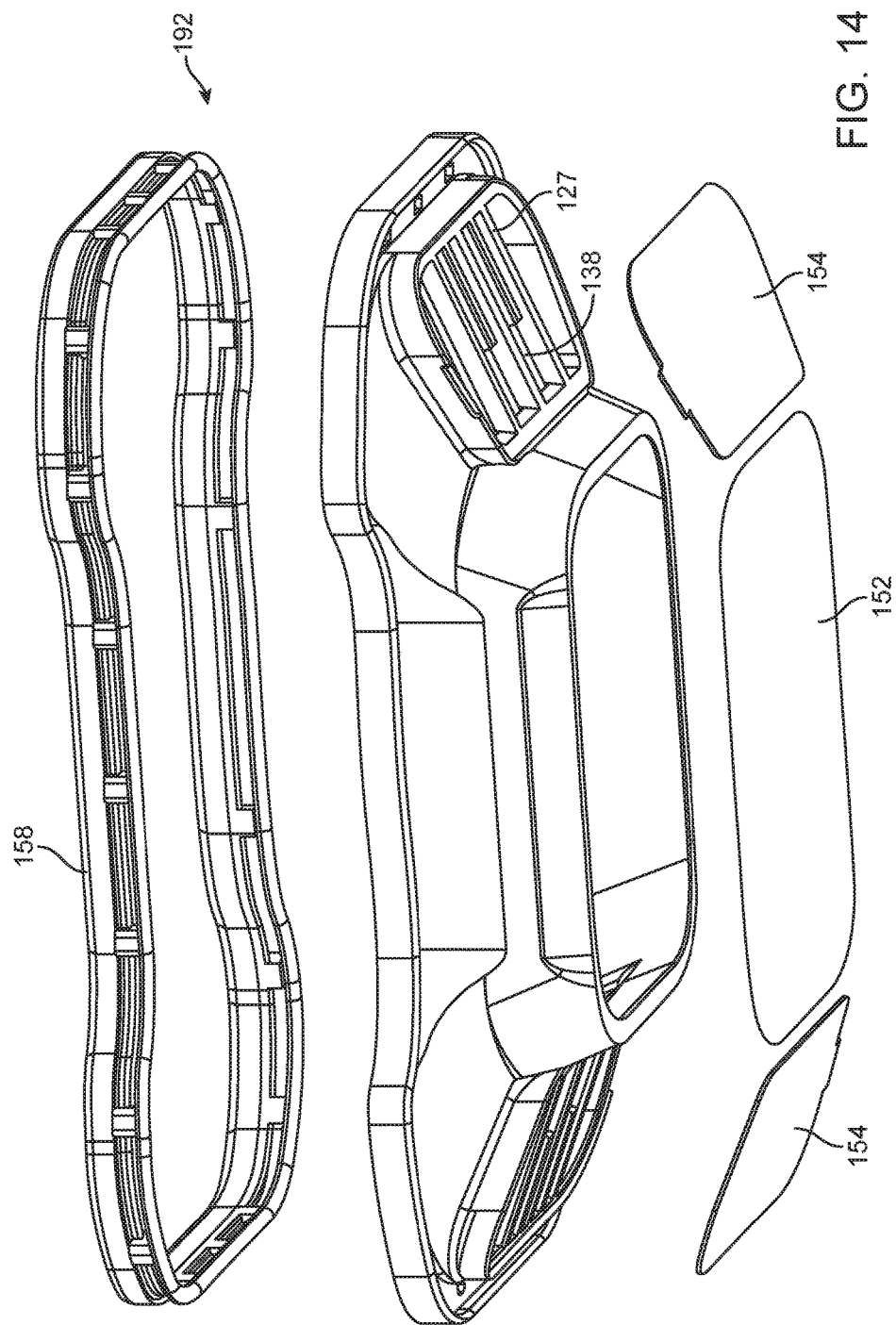
FIG. 14 is an exploded perspective side view of the inner insert assembly of FIG. 13.

FIG. 14 is an exploded perspective side view of inner insert 192, revealing vacuum channels 138 and attachment supports 127 behind filters 154. As described above, vacuum channels 138 allow for airflow under attachment mechanisms 126 (see, e.g., FIG. 6) and through filters 154, to allow for vacuum communication between applicator chamber 118 (see, e.g., FIG. 6) and tissue acquisition chamber 142 (see, e.g., FIG. 5) of tissue interface module 116 (see, e.g., FIG. 2). Inner insert 192 further includes bio-barrier 152 and gasket 158.

Figure 15:
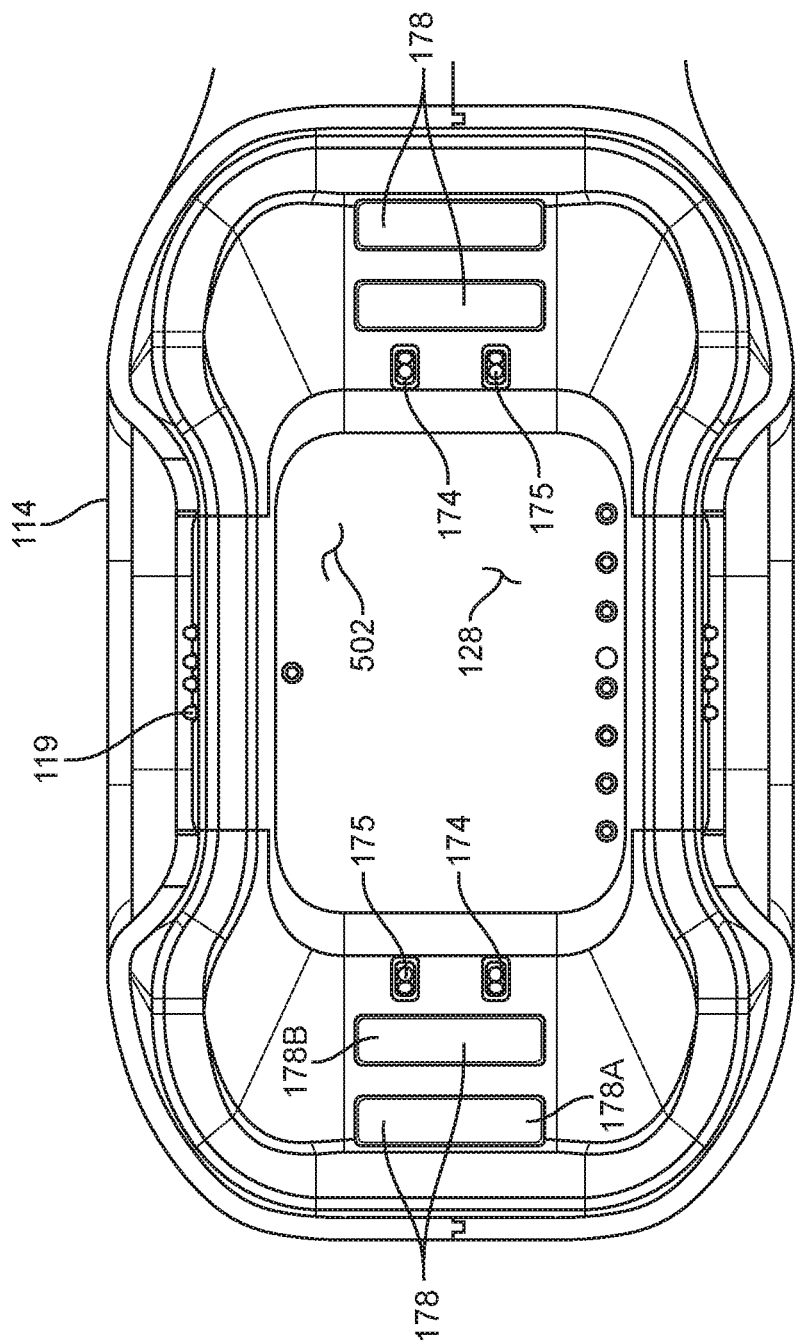
FIG. 15 shows an end view of an applicator without a tissue interface module attached.

FIG. 15 shows an end view of applicator 114 without tissue interface module 116 (see, e.g., FIG. 2) attached. Applicator 114 may include electrical contacts 119 for electrical coupling with electrical contacts 160 and printed circuit board 162 (see, e.g., FIG. 7) of tissue interface module 116. Applicator 114 may further include cooling plate 128, applicator vacuum inlets 174, applicator tissue treatment surface 502, aesthetic features 175 and applicator engagement surface 178. Applicator engagement surfaces 178 are configured to engage attachment mechanisms 126 of tissue interface module 116. Applicator engagement surface 178 may include a first applicator engagement surface 178A positioned at a distal end of a first magnetic extender 179 (see FIG. 17A) and a second applicator engagement surface 178B positioned at a distal end of a second magnetic extender 179. Applicator vacuum inlets 174 are coupled to a vacuum source in console 112. When tissue interface module 116 is attached to applicator 114 (see, e.g., FIG. 15), applicator vacuum inlets 174 are configured be positioned in applicator chamber 118 (see, e.g., FIG. 6) and to evacuate air from applicator chamber 118 through, for example, vacuum interface 504, creating a vacuum in applicator chamber 118 and pulling air through filters 154 (see FIG. 9) from through tissue acquisition chamber 142 (see, e.g., FIG. 5).

Cooling plate 128 of applicator 114 may include an alumina or other metal frame surrounding the back side of cooling plate 128 to add structural strength to cooling plate 128, a plurality (e.g., four) of threaded rods may be bonded to the alumina frame to cooling plate 128 to a waveguide holder (not shown). In some embodiments, cooling plate 128 may comprise a ceramic material having approximately 94 to 99 percent alumina and 1 to 6 percent other material. Cooling plate 128 may further include one or more thermocouple traces (of, for example, copper and constantan). These thermocouples may be arranged to detect a temperature of cooling plate 128, a temperature of the surface of the tissue to be treated or a temperature of the interface. Such traces may be routed in side by side pairs to, for example, reduce the effect of noise on the output of such thermocouples. Such traces may be aligned to be perpendicular to the e-field emitted from the applicator to prevent the thermocouple traces from disrupting the e-field. When applicator 114 is attached to tissue interface module 116, applying vacuum to tissue interface module 116 may result in pulling bio-barrier 152 of FIG. 5 of tissue interface module 116 against cooling plate 128 of applicator 114.

Figure 16:
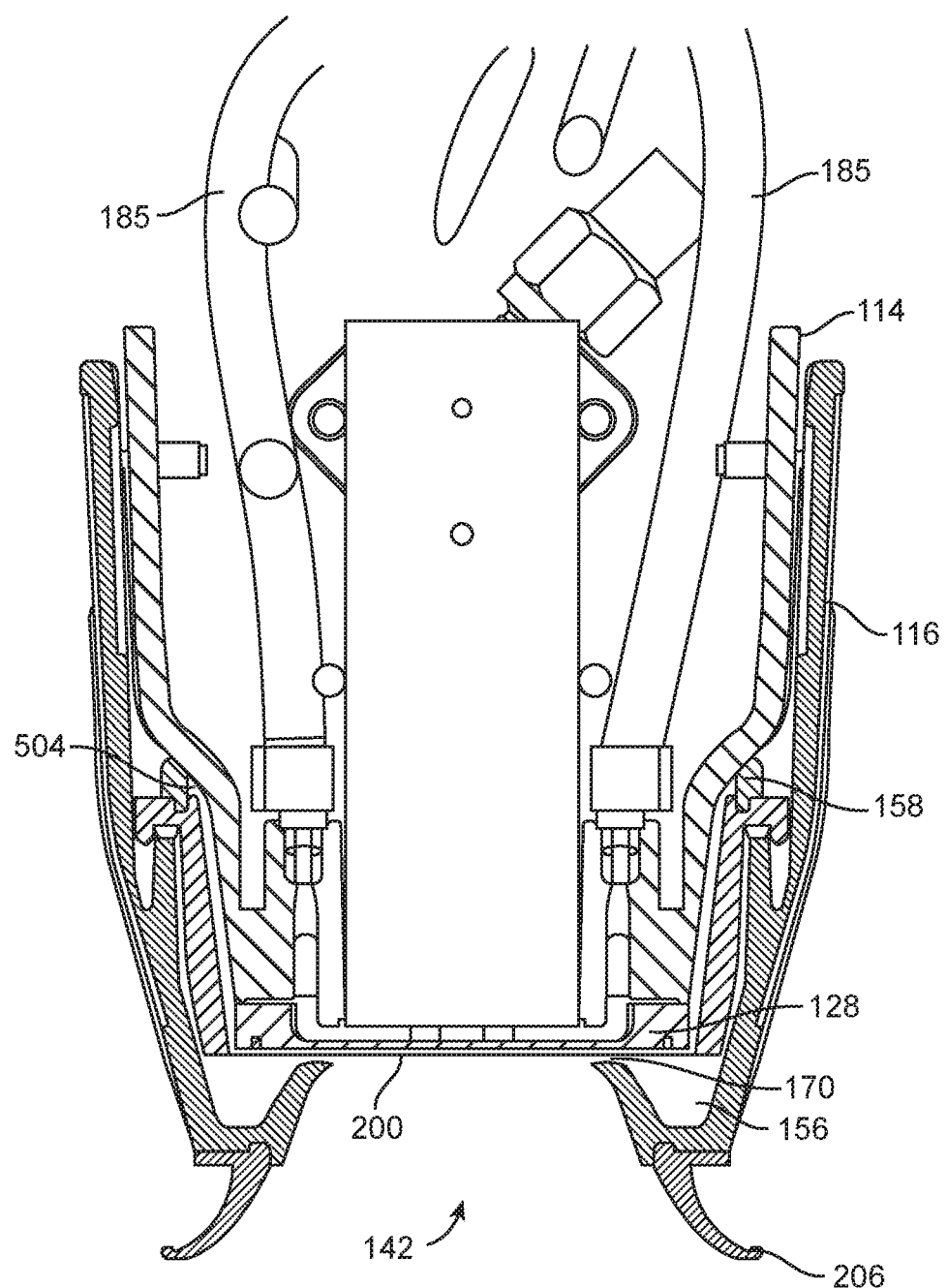
FIG. 16 illustrates a cutaway view of a section of an applicator and a portion of tissue interface module.

FIG. 16 shows a side cutaway view of a section of applicator 114 and a portion of tissue interface module 116, including gasket 158, attached to applicator 114. In FIG. 16, the side angle shows how skirt 206 and tissue interface surface 200 form at least a portion of tissue acquisition chamber 142. A portion of a vacuum flow path according to an embodiment may also be seen in FIG. 16, including, for example, tissue acquisition chamber 142, expandable aperture 170, and fluid trap 156. A vacuum path according to an embodiment may further include vacuum interface 504. Also shown are coolant conduits 185 of applicator 114, which supply coolant fluid to cool applicator cooling plate 128. Coolant conduits 185 may include antimicrobial fittings and tubing using, for example, natural silver ion implanted antimicrobial tubing manufactured by Eldon James such as, for example Flexelene™. Such fittings and tubing may provide protection against microbial colonization (e.g., bacteria, mildew, mold and fungi). The tubing for conduits 185 may also be adapted to provide protection against microbial colonization without impacting, reducing or modifying the microwave characteristics (e.g., loss characteristics) of cooling fluid passing through such antimicrobial fittings and tubing.

FIGS. 17A-17B are side cutaway views of a portion of applicator 114 and a portion of tissue interface module 116 attached to applicator 114. In FIGS. 17A-17B, applicator 114 includes magnet 186 which may be rotatable or otherwise movable and may be configured to complete a magnetic circuit between magnetic extenders 179 and attachment mechanism 126 to attach tissue interface module 116 to applicator 114. Applicator 114 further includes antenna array 124. Completing the magnetic circuit between magnetic extenders 179 and attachment mechanism 126 magnetically couples attachment mechanism 126 on tissue interface module 116 to magnetic extenders 179 on applicator 114. Magnet 186 may be coupled to a rotation mechanism such as a direct current gear motor or an RC servomotor, so as to rotate magnet 186 within magnetic extenders 179 between a position which results in an incomplete magnetic circuit and a position which results in a completed magnetic circuit. In FIG. 17A, the "N" and "S" poles of magnet 186 are shown in the vertical position, resulting in an incomplete magnetic circuit by not completing the magnetic circuit with magnetic extenders 179 and attachment mechanism 126. When the magnetic circuit is incomplete, there is little or no magnetic attraction between attachment mechanism 126 and magnetic extenders 179, facilitating removal of tissue interface module 116 from applicator 114. In FIG. 17B, the "N" and "S" poles of magnet 186 have been rotated into the horizontal position, thereby completing the magnetic circuit and magnetically attaching magnetic extenders 179 to attachment mechanism 126. In some embodiments, a stop may be implemented using a hall-effect position sensor or a hard stop. In some embodiments of the invention, magnet 186 may be positioned to partially complete the magnetic circuit prior to or as tissue interface module 116 is attached to applicator 114 to facilitate proper seating of tissue interface module 116. Once tissue interface module 116 is properly seated on applicator 114, magnet 186 may be positioned to fully close the magnetic circuit, holding tissue interface module 116 in place.

Other features of tissue interface module 116 but shown in FIGS. 17A and 17B include gasket 158, expandable aperture 170, fluid trap 156, tissue interface surface 200, skirt 206, tissue acquisition chamber 142, bio-barrier 152, filter 154, outer shell 193, reflector 166, and attachment mechanisms 126. Also shown, a sealing surface 121 (which may also be referred to as a gasket contact surface) of applicator 114 may be angled to receive gasket 158 from tissue interface module 116. In this embodiment, placing sealing surface 121 at an angle, causes gasket 158 to bend when tissue interface module 116 is attached to applicator 114, improving the sealing characteristics by maximizing the contact surface between gasket 158 and sealing surface 121 and reducing the force required to attach the tissue interface module 116 to the applicator 114. Also illustrated are cooling plate 128, applicator tissue treatment surface 502 and vacuum interface 504.

Figure 18:
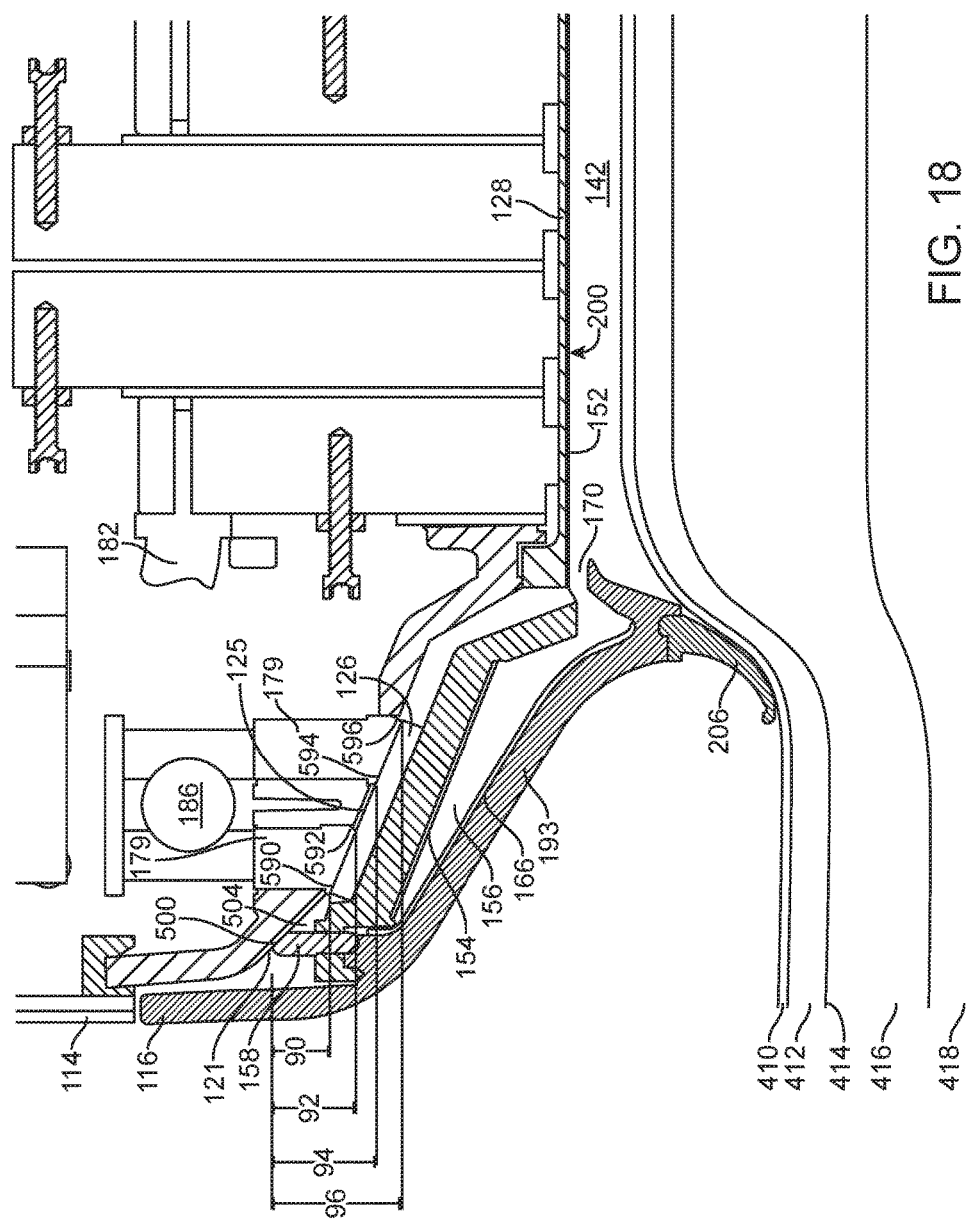
FIG. 18 illustrates a side cutaway view of a section of an applicator and a tissue interface module as tissue is pulled into a tissue acquisition chamber by applied vacuum.

In FIG. 18, applicator 114 includes magnetic extenders 179, magnet 186, sealing surface 121 and cooling plate 128. Tissue interface module 116 includes gasket 158, expandable aperture 170, fluid trap 156, skirt 206, tissue acquisition chamber 142, bio-barrier 152, filter 154, outer shell 193, reflector 166, attachment mechanism 126 and tissue interface surface 200. Also illustrated is vacuum interface 504. Tissue (including epidermis 410, dermis 412, dermal-hypodermal interface 414, hypodermis 416 and muscle 418) is shown positioned partially within tissue acquisition chamber 142. In FIG. 18 applicator 114 and tissue interface module 116 of FIGS. 17A-17B have been placed in contact with tissue. In FIG. 18 vacuum pressure has been initiated and air is being drawn from applicator chamber 118, resulting in a drop in pressure in applicator chamber 118 and in tissue acquisition chamber 142. In FIG. 18, the tissue (including epidermis 410, dermis 412, dermal-hypodermal interface 414 and hypodermis 416) is shown being pulled into tissue acquisition chamber 142. As tissue is pulled into tissue acquisition chamber 142 it moves towards tissue interface surface 200 and bio-barrier 152. Pulling tissue into tissue acquisition chamber 142 may also provide a benefit of moving structures in the dermis and hypodermis away from deeper structures such as, for example, muscles and nerves. Vacuum pressure applied by applicator 114 to applicator chamber 118 of tissue interface module 116 may be adapted to localize and stabilize tissue located in tissue acquisition chamber 142. When tissue is fully engaged in tissue acquisition chamber 142, the vacuum pressure is also adapted to hold tissue positioned in tissue acquisition chamber 142 against tissue interface surface 200 and bio-barrier 152. Additionally, vacuum in tissue acquisition chamber 142 pulls bio-barrier 152 into contact with cooling plate 128, so as to ensure the efficient transfer of cooling energy to the epidermis 410 and underlying tissue during application of microwave energy. In some embodiments of the invention, the vacuum is configured to have a flow rate of approximately 13.7 Standard Fluid Liters Per Minute during tissue acquisition which flow rate may, in some embodiments, vary by up to plus or minus twenty percent.

In one particular embodiment, as shown in FIG. 18, the vertical distance 90 from gasket engagement surface 500 (which in one embodiment may be the top of gasket 158) to a first connection point 590 on engagement surface 125 of FIGS. 11-12 of the uppermost portion of attachment mechanism 126 is approximately 0.15". In one embodiment, the vertical distance 92 from gasket engagement surface 500 to a second connection point 592 on engagement surface 125 of the portion of attachment mechanism 126 that intersects the inside of the left magnetic extender 179 is approximately 0.22". In one embodiment the vertical distance 94 from gasket engagement surface 500 to a third connection point 594 on engagement surface 125 of the portion of attachment mechanism 126 that intersects the inside of the right magnetic extender 179 is approximately 0.27". And, in a further embodiment, the vertical distance 96 from gasket engagement surface 500 to a fourth connection point 596 on at the lower portion of engagement surface 125 of attachment mechanism 126 is approximately 0.34". In some embodiments these measurements may vary by, for example, up to ±0.01". In some embodiments, these measurements may vary by ±0.05".

In one embodiment, the angle of engagement surface 125 of attachment mechanism 126 may be identical or substantially identical (in one embodiment, within, for example, five degrees) to the angle of applicator engagement surface 178 at a distal end of magnetic extenders 179 to provide a flush fit between the extenders and the attachment mechanism 126 when the tissue interface module 116 is attached to the applicator 114. In one embodiment, the angle of applicator engagement surfaces 178 may be arranged to be parallel or substantially parallel (in one embodiment within, for example, up to five degrees of parallel) to engagement surfaces 125 of attachment mechanism 126 to provide a flush fit between the extenders and the attachment mechanism 126 when tissue interface module 116 is attached to the applicator 114. In one embodiment of the invention engagement surface 125 may be sized and arranged to maximize the portion of engagement surface 125 contacted by applicator engagement surface 178. In one embodiment of the invention, a first portion of engagement surface 125 is arranged to contact a first applicator engagement surface 178A and a second portion of engagement surface 125 may be sized and arranged to contact a second applicator engagement surface 178B.

In one embodiment of the invention engagement surface 125 may be sized and arranged to form a ferromagnetic bridge between applicator engagement surface 178A and 178B when tissue interface module 116 is positioned on applicator 114. In one embodiment of the invention engagement surface 125 may be sized and arranged to form a closed magnetic circuit with applicator engagement surface 178A and 178B when tissue interface module 116 is positioned on applicator 114.

In FIG. 18 expandable aperture 170 may be configured to expand when vacuum is applied by an applicator 114 to applicator chamber 118 and to tissue acquisition chamber 142 with tissue interface module 116 attached to applicator 114. In some embodiments, the application of vacuum to tissue interface module 116 at vacuum interface 504 pulls bio-barrier 152 inwards towards cooling plate 128 of applicator 114, which increases the size of expandable aperture 170. FIGS. 17A and 17B illustrate embodiments of the invention wherein bio-barrier 152 is in its un-flexed state and expandable aperture 170 is at its minimum width. In FIG. 18, expandable aperture 170 has been opened to its maximum width by the application of vacuum pressure to applicator chamber 118, which pulls bio-barrier 152 against applicator tissue treatment surface 502 (see, e.g., FIG. 15), which, in one embodiment may be cooling plate 128. As tissue is pulled into and air is pulled out of tissue acquisition chamber 142 a small vacuum pressure differential is maintained by the drop in pressure across filter 154 resulting from air flowing through filter 154 such that the pressure in applicator chamber 118 is less than the pressure in tissue acquisition chamber 142. This pressure differential may be used to, for example, maintain the position of bio-barrier 152 against cooling plate 128 during the acquisition of tissue. This pressure differential may further be used to ensure that bio-barrier 152 is positioned against cooling plate 128 prior to tissue contacting tissue interface surface 200. This pressure differential may further be used to ensure that bio-barrier 152 is positioned against cooling plate 128 without bubbles, voids or deformities. This pressure differential may further be used to ensure that tissue being pulled into tissue acquisition chamber 142 does not move or deform bio-barrier 152. Once the air is removed from tissue acquisition chamber 142 and replaced by tissue, air will no longer flow through filter 154 into applicator chamber 118 and the pressure in the two chambers will be balanced or substantially balanced (e.g., having a pressure differential of less than approximately 4 pounds per square inch). With tissue properly positioned in applicator chamber 118, the tissue pressing against tissue interface surface 200 may be used to maintain position of bio-barrier 152 against cooling plate 128, preventing, for example, the formation of voids, bubbles or deformities which could result in hot spots. In some embodiments of the invention, applicator 114 may be positioned in applicator chamber 118 in a manner wherein cooling plate 128, or some other feature of tissue interface module 116, contacts bio-barrier 152 prior to the application of vacuum, preventing expandable aperture 170 from opening when vacuum is applied.

Figure 19:
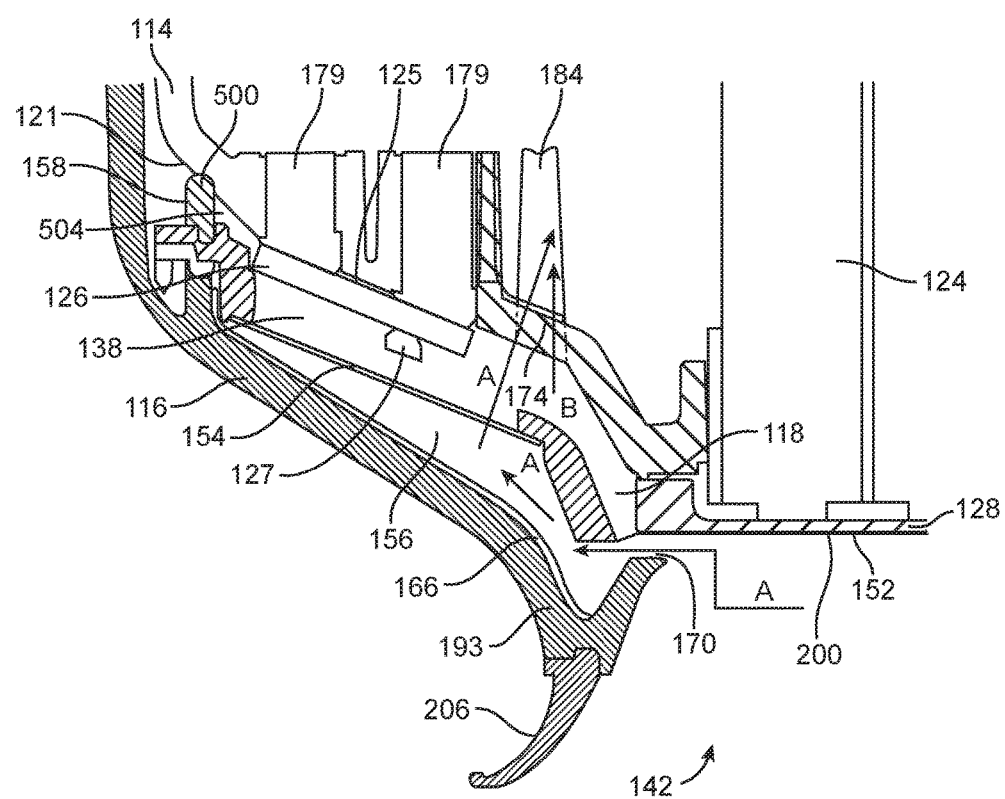
FIG. 19 shows a side cutaway view of a section of an applicator and a tissue interface module showing an air path with vacuum applied.

FIG. 19 is a side cutaway view of applicator 114 and tissue interface module 116 of FIGS. 17-18 showing air paths A and B through tissue interface module 116 with vacuum applied. Vacuum may be applied by applicator 114 directly to applicator chamber 118 (through, for example, vacuum interface 504) of tissue interface module 116 to create vacuum within applicator chamber 118, as well as within tissue acquisition chamber 142. A first vacuum flow path A extends from tissue acquisition chamber 142, through expandable aperture 170, into fluid trap 156, through filter(s) 154, through vacuum channels 138 and into applicator chamber 118 and into applicator 114. Second vacuum flow path B shows vacuum being pulled directly from applicator chamber 118. From applicator chamber 118, air is pulled into applicator 114 through, for example, vacuum interface 504. When vacuum is created along flow path A, tissue positioned at acquisition chamber opening 143 may be pulled into tissue acquisition chamber 142, as shown in FIG. 18. Tissue, lubricants or bodily fluids, such as blood or sweat, may collect in fluid trap 156 and those not captured in fluid trap 156 may be stopped by filter 154. Since filters 154 are permeable to air or gas but not to liquid, vacuum may be pulled through filters 154 without contaminating applicator chamber 118 or the surface of applicator 114. The vacuum air paths A and B may be used to equalize or substantially equalize pressure (in some embodiments equalize to, for example, within four pounds per square inch) on both sides of filter 154 (i.e., the pressure in tissue acquisition chamber 142 and applicator chamber 118). In one embodiment of the invention the resistance to airflow is higher in vacuum path A than in vacuum path B, ensuring that, as long as air is flowing in vacuum path A, the air pressure in applicator chamber 118 will be lower than the air pressure in tissue acquisition chamber 142. In one embodiment of the invention, filter 154 provides resistance to the flow of air in vacuum path A, ensuring that, as long as air is flowing in vacuum path A, the air pressure in applicator chamber 118 will be lower than the air pressure in tissue acquisition chamber 142.

In some embodiments, the vacuum flow path is completely internal to tissue interface module 116 and applicator 114, originating in applicator 114 itself, and pulling vacuum from applicator chamber 118, through filters 154, through fluid traps 156, through expandable aperture 170, and finally through tissue acquisition chamber 142 to engage tissue in tissue acquisition chamber 142. In some embodiments, the vacuum flow path hooks up directly from applicator chamber 118 of tissue interface module 116 to vacuum inlets 174 of applicator 114, without requiring an external attachment from tissue interface module 116 to applicator 114 or to a separate vacuum source. In one embodiment, the vacuum path may include at least one portion having a gap width of approximately 0.036 inches. In one embodiment, the minimum gap width at any point along vacuum path A may be approximately 0.036 inches. In one embodiment, the smallest dimension in a cross section of the airflow pathway along vacuum path A will be approximately 0.036 inches. In some embodiments, these measurements may vary by, for example, up to plus or minus twenty percent. In one embodiment of the invention, the smallest cross section in vacuum path A will be the cross section formed on a first side by expandable aperture 170.

When using tissue interface module 116 vacuum may be achieved and maintained when tissue interface module 116 is attached to applicator 114, forming a seal between tissue interface module 116 and applicator 114, and tissue is engaged by tissue acquisition chamber 142 (as shown in FIG. 18) forming a seal between the engaged tissue and skirt 206. Tissue interface module 116 may include one or more vacuum balance pathways designed therein. One vacuum balance path may include tissue acquisition chamber 142, fluid trap 156 and at least one filter 154 adapted to allow air to pass without allowing other fluids to pass. An expandable aperture 170 forming an entrance to fluid trap 156 may also be included and may be flexible to allow the entrance to fluid trap 156 to open, creating a wider gap when vacuum is applied. A reflector 166 may further be included in the vacuum path as, for example, a portion of fluid trap 156.

In one embodiment of the invention, when using tissue interface module 116, and particularly as tissue is pulled into tissue acquisition chamber 142, a balance or approximate balance between air pressure in applicator chamber 118 and tissue acquisition chamber 142 may be maintained. In one embodiment of the invention the air pressure in applicator chamber 118 may be, for at least a period of time, at a pressure below the air pressure in tissue acquisition chamber 142. In one embodiment of the invention, when using tissue interface module 116, and particularly as tissue is pulled into tissue acquisition chamber 142, a balance may be maintained wherein air pressure in applicator chamber 118 is slightly lower than an air pressure in tissue acquisition chamber 142. An applicator chamber 118 may be designed and configured to allow applicator 114, when inserted into applicator chamber 118 to form an airtight seal around applicator chamber 118 (e.g., with a gasket 158) and to position a distal end of applicator 114 (e.g., cooling plate 128 application surface) within a predetermined distance (e.g., approximately 0.026 inches) of bio-barrier 152. A first balance path (e.g., Path B in FIG. 19) may be created by the direct interconnection between applicator 114 and applicator chamber 118 such that air pulled from applicator chamber 118 travels directly into applicator 114 through vacuum inlets 174. A second balance path (e.g., Path A in FIG. 19) may be created by the indirect interconnection between applicator 114 and tissue acquisition chamber 142, wherein air from tissue acquisition chamber 142 must pass through at least filter 154 before being pulled into applicator 114 through vacuum inlets 174. First and second balance paths may combine in applicator chamber 118. In one embodiment, air being evacuated from tissue acquisition chamber 142, through filter 154 may flow past one or more magnetic plates forming attach mechanism 126. In one embodiment of the invention, applicator 114 may further include antenna array 124, magnetic extenders 179, and tissue interface surface 200. In one embodiment of the invention tissue interface module 116 may further include engagement surface 125, outer shell 193, skirt 206 and gasket engagement surface 500.

Figure 20:
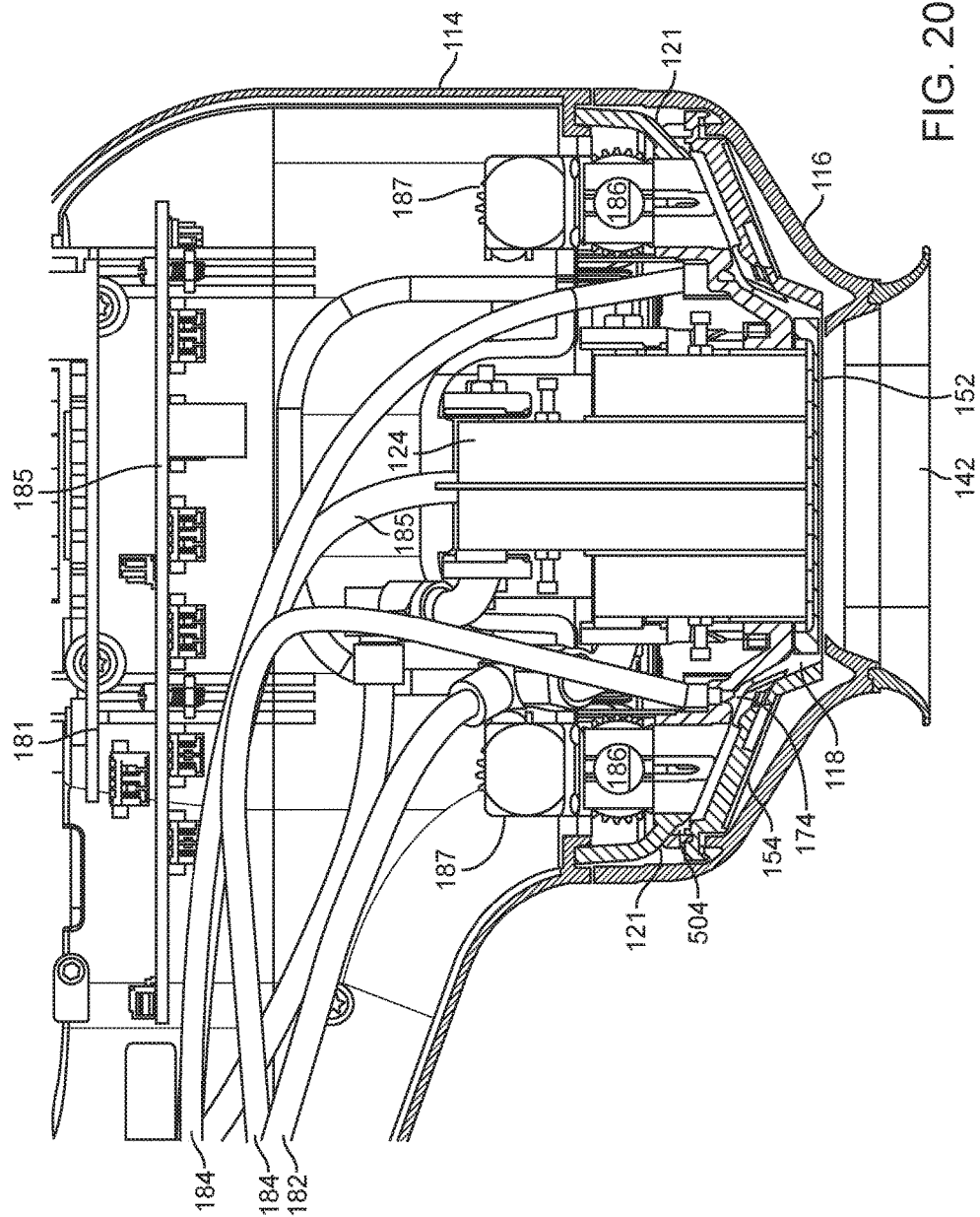
FIG. 20 is a side cutaway perspective view of an applicator and a tissue interface module showing some of the internal components of the applicator, including vacuum conduits.

FIG. 20 shows a side cutaway view of a portion of the distal end of applicator 114, showing some of the internal components of applicator 114, including applicator logic circuits 181, microwave feed cables 182, coolant conduits 185, vacuum conduits 184, antenna array 124, sealing surface 121 and magnetic drive 187. Magnetic drive 187 may include, for example, DC motors to position magnets 186 (e.g., by rotating magnets 186) and hall-effect sensors to sense the position of magnets 186. FIG. 20 also includes a cutaway view of tissue interface module 116, including applicator chamber 118, bio-barrier 152, vacuum interface 504, filter 154 and tissue acquisition chamber 142. As shown, applicator chamber 118 of tissue interface module 116 is adapted and configured to receive the distal end of applicator 114, positioning antenna array 124, cooling plate 128 and vacuum inlets 174 in applicator chamber 118.

Figure 21:
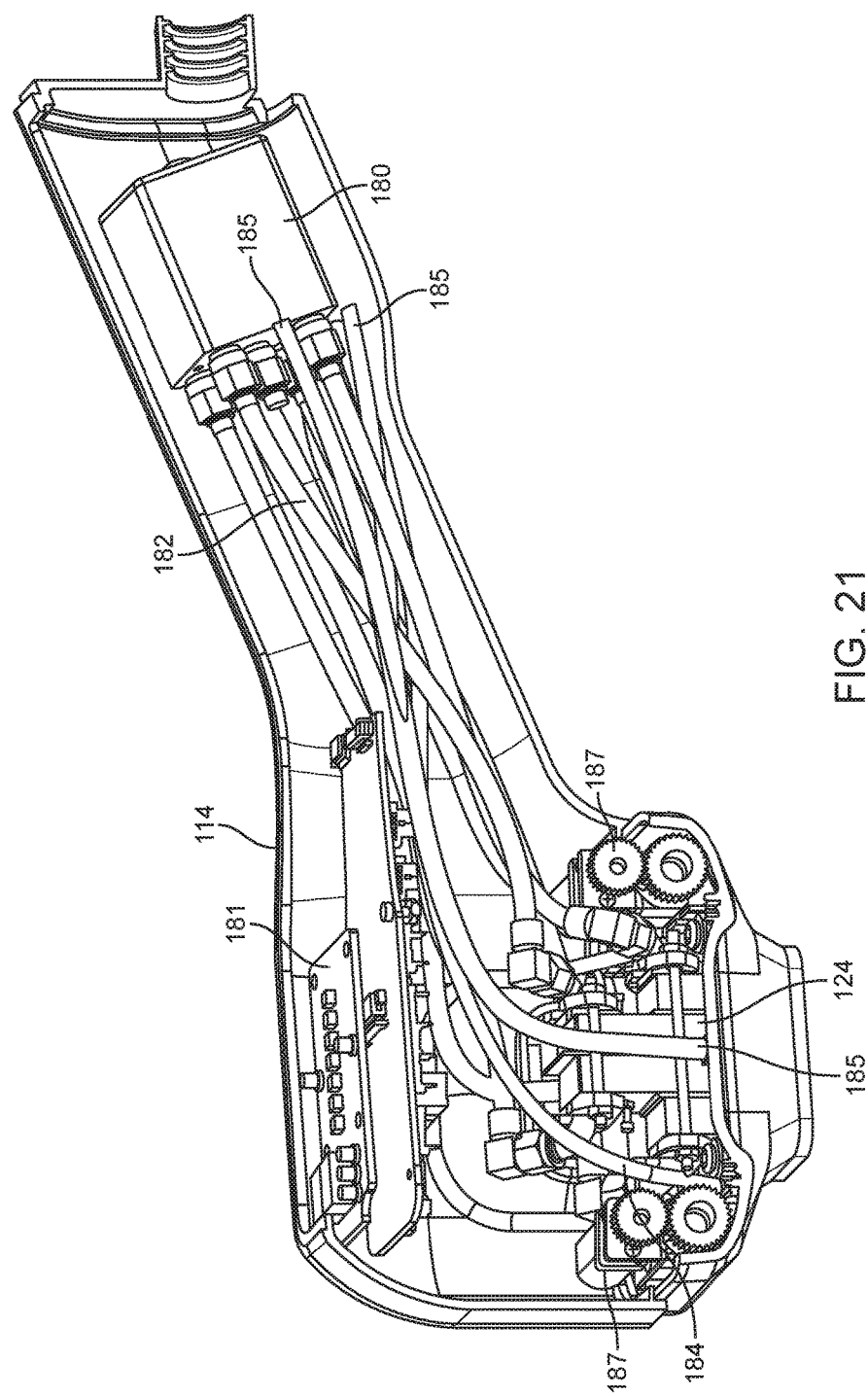
FIG. 21 illustrates a side cutaway perspective view of an applicator showing some of the internal components of the applicator.

FIG. 21 is a side cutaway perspective view of applicator 114 showing some of the internal components of applicator 114, including applicator logic circuits 181, microwave feed cables 182, coolant conduits 185, vacuum conduits 184, antenna array 124, microwave switch 180 and magnetic drive 187.

Figure 22:
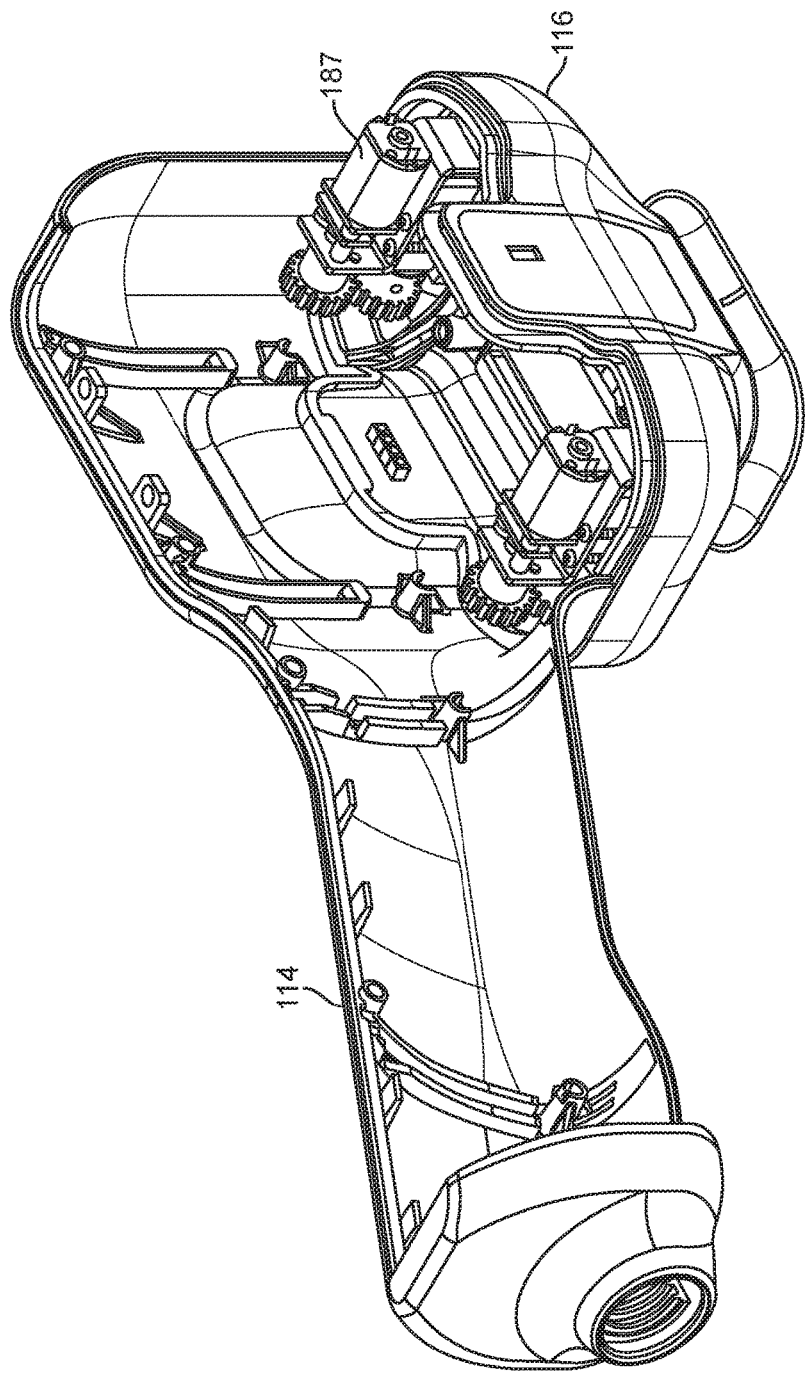
FIG. 22 shows a side cutaway perspective view of an applicator with a tissue interface module attached to the applicator and showing a portion of magnetic drive components.

FIG. 22 is a side cutaway perspective view of applicator 114 with tissue interface module 116 attached showing a portion of magnetic drive components, including magnetic drive 187. Magnetic drive 187 may be used to open a magnetic circuit by, for example, positioning magnet 186 in the position illustrated in FIG. 17A with respect to extenders 179. Magnetic drive 187 may be used to complete a magnetic circuit by, for example, positioning magnet 186 in the position illustrated in FIG. 17B with respect to extenders 179. With magnet 186 positioned as illustrated in FIG. 17B, tissue interface module 116 may be magnetically attached to applicator 114.

In some embodiments, engagement surface 125 forms an Angle X (see FIG. 11) of approximately 22.5 degrees from horizontal (e.g., from a plane through bio-barrier 152 when bio-barrier 152 is un-flexed) so as to couple to mating attachment points on applicator 114, such as, for example, applicator engagement surfaces 178 at a distal end of magnetic extenders 179. In other embodiments, engagement surface 125 forms an Angle X of between approximately 17.5 degrees and 27.5 degrees, or alternatively, an Angle X of between approximately 12.5 degrees and 32.5 degrees. In other embodiments, Angle X of engagement surface 125 may vary, up to and including 45 degrees or more, depending upon the angle chosen for the mating engagement surfaces on applicator 114. In embodiments of the invention, applicator engagement surfaces 178 on applicator 114 are designed to be parallel to engagement surface 125 when tissue interface module 116 is properly positioned on applicator 114. Creating an engagement surface 125 which conforms to the mating surface (e.g., applicator engagement surface 178) on applicator 114 may be important to ensure the maximum surface area of contact between engagement surface 125 and mating surfaces on applicator 114. Ensuring maximum surface area contact may, for example, maximize the magnetic force applied to hold tissue interface module 116 in place and prevent tissue interface module 116 from shifting or falling off of applicator 114 during treatment. In some embodiments Applicator engagement surface 178 may extend a predetermined distance from the outer surface of applicator 114 to ensure proper contact between applicator engagement surfaces 178 and engagement surface 125 and proper positioning of gasket engagement surface 500 of gasket 158 against sealing surface 121. Maximizing the magnetic force will also provide optimum compression of gasket 158 when it is positioned against the outer surface of applicator 114, preventing vacuum leaks which could cause tissue in tissue acquisition chamber 142 to shift or move during treatment and cause such tissue to lose contact with bio-barrier 152 and/or tissue interface surface 200 or to lose functional contact with applicator tissue treatment surface 502 and/or cooling plate 128. Further, any movement of tissue interface module 116 with respect to applicator 114 during treatment may cause bubbles, voids or deformities to form between bio-barrier 152 and applicator tissue treatment surface 502. Engagement surface 125 may further be arranged to be parallel to or substantially parallel (within e.g., 10 degrees), for example, surfaces at a distal end of magnetic extenders 179 on applicator 114. Engagement surface 125 may further be arranged such that engagement surfaces 125 contact substantially all (e.g., eighty percent or more) of a distal end surface of magnetic extenders 179 on applicator 114. Engagement surface 125 may further be arranged to maximize the magnetic force exerted on attachment mechanism 126 by magnet 186 when magnet 186 is arranged to exert force on attachment mechanism 126 through magnetic extenders 179. Engagement surface 125 may be positioned to extend from applicator engagement surface 178A to applicator engagement surface 178B, thus closing the gap between applicator engagement surface 178A and applicator engagement surface 178B and creating a closed magnetic circuit.

Bio-barrier 152 (which may also be referred to as a first bio-barrier, a membrane or first membrane) may be configured and/or made of a material which is substantially impermeable to both liquids (e.g., bodily fluids such as blood or sweat) and may also be impermeable to gases (e.g., air). In embodiments of the invention, substantially impermeable may mean that a barrier is, for example, permeable enough to permit some fluid and/or air to pass but not permeable enough to effect the functionality of the barrier or of tissue interface module 116. In embodiments of the invention, substantially impermeable may mean that a barrier is, for example, permeable enough to permit some fluid and/or air to pass but not permeable enough to allow biological fluids, such as blood or sweat, to pass. In some embodiments, bio-barrier 152 may be constructed of impermeable materials, such as, for example, polyurethane film and may have a thickness of, for example, 0.0005 inches or 0.00085 inches. In some embodiments, bio-barrier 152 may have a thickness of between approximately 0.00075 inches and 0.001 inches. Bio-barrier 152 is further designed to be sufficiently flexible to conform to applicator tissue treatment surface 502 (which may also be referred to as a tissue surface, treatment surface or distal surface of a cooling plate), where applicator tissue treatment surface 502 is located at a distal end of applicator 114 (see, for example, FIG. 15) without creating bubbles, voids or deformities. In some embodiments of the invention (see, for example, FIG. 9), bio-barrier 152 and filter 154 (which may also be referred to as a second bio-barrier, a permeable bio-barrier or a semi-permeable bio-barrier) may work together to comprise a multifunctional bio-barrier. In embodiments of the invention, filter 154 may comprise a first filter and a second filter. In embodiments of the invention, filter 154 may comprise a first filter and a second filter wherein the first and second filters are positioned on opposite sides of bio-barrier 152. In embodiments of the invention a multifunction bio-barrier, comprising, for example, a first impermeable membrane and a second air-permeable membrane, may be used to balance vacuum pressure in an applicator chamber 118 with vacuum pressure in a tissue acquisition chamber 142 when air is drawn, by, for example, the attachment of vacuum ports to applicator chamber 118. In embodiments of the invention a multifunction bio-barrier, comprising, for example, a first impermeable membrane and a second air-permeable membrane, may be used in a vacuum pathway between applicator chamber 118 and a tissue acquisition chamber 142 such that establishing a vacuum in applicator chamber 118 pulls air from tissue acquisition chamber 142 through the multifunction bio-barrier while preventing biological fluids from passing from tissue acquisition chamber 142 into applicator chamber 118, preventing contamination of the distal end of the applicator 114.

Bio-barrier 152 may be designed to have specific microwave and thermal characteristics. For example, bio-barrier 152 may be designed to have a loss tangent ($\tan(\delta)$) of 0.1 or less, and more particularly, a loss tangent of approximately 0.0004. In some embodiments, Bio-barrier 152 may have a loss tangent ($\tan(\delta)$) of less than one. In one embodiment, bio-barrier 152 may be made from a material having a lost tangent of one or less. In other embodiments, bio-barrier 152 may be designed to have an electrical conductivity suitable for use a in a microwave system, such as having an electrical conductivity ($\sigma$) of between 0.0 and 0.2 siemens/meter. In one embodiment of the invention bio-barrier 152 may be designed to have an electrical conductivity which is less than or equal to the transmission frequency in hertz (e.g., 5.8 GHz) multiplied by the real part of the permittivity of bio-barrier 152. Bio-barrier 152 may also be designed to have a thermal conductivity and be made from a material suitable for use in a microwave system, such as having a thermal conductivity of at least approximately 0.1 watts per meter Kelvin (0.1 W/mK), and desirably 0.1 to 0.6 W/mK, and most desirably 0.25 to 0.45 W/mK. Furthermore, bio-barrier 152 may be designed to have a heat transfer coefficient which makes it suitable for efficiently removing heat from tissue adjacent to bio-barrier 152, such as having a heat transfer coefficient of approximately 7874 $W/m^2K$. In some embodiments, these measurements may vary by, for example, up to plus or minus twenty percent.

In some embodiments, bio-barrier 152 may be designed to conform to applicator tissue treatment surface 502, particularly when a vacuum is applied to applicator chamber 118. In some embodiments, bio-barrier 152 may be configured to deflect at least 0.010 inches with a vacuum of, for example, approximately −20 inches of mercury applied to applicator chamber 118 without tearing or deforming. In some embodiments, these measurements may vary by, for example, up to plus or minus twenty percent. Bio-barrier 152 may be designed to deflect or stretch to cover applicator tissue treatment surface 502 without forming bubbles, voids or deformities as such bubbles, voids or deformities may perturb microwave energy passing through bio-barrier 152. Such perturbations may, in certain circumstances, result in potential hot spots adjacent tissue interface surface 200 and/or between bio-barrier 152 and applicator tissue treatment surface 502 (see, for example, FIG. 15). In embodiments of the invention a distal surface of tissue cooling plate 128 forms at least a portion of applicator tissue treatment surface 502 of applicator 114. Such bubbles, voids or deformities may provide pockets of insulation (e.g., air) between the skin surface and cooling plate 128, preventing cooling plate 128 from properly cooling the surface of the skin as energy is applied through bio-barrier 152.

When tissue interface module 116 is placed against tissue, such as, for example, the skin, skirt 206 may engage the tissue and form a sealed enclosure, wherein the enclosure includes the tissue, tissue acquisition chamber 142, skirt 206, and bio-barrier 152. With tissue interface module 116 positioned on applicator 114, vacuum may then be applied by pulling air through vacuum inlets 174 (also referred to as vacuum ports or vacuum inlet openings) at a distal end of applicator 114 (see, for example, FIG. 15) to pull tissue into tissue acquisition chamber 142 and up against tissue interface surface 200, which, in some embodiments, may comprise a distal surface of bio-barrier 152. In the embodiment of FIG. 5, tissue interface module 116 may include, for example, four vacuum notches 214. However, in other embodiments, more or fewer vacuum notches 214 may be included around bio-barrier 152. Increasing the number of vacuum notches 214 and positioning the vacuum notches around a perimeter of bio-barrier 152 may improve vacuum performance in the tissue acquisition chamber 142 and provide vacuum redundancy in the event that one or more of vacuum notches 214 becomes clogged with blood, tissue, or other bodily fluids during treatment.

In some embodiments, filters 154 may be made from hydrophobic material. In other embodiments, filters 154 may have a pore size which allows for passage of gas or air with a hydrophobicity that prevents the passage of liquids such as blood and sweat. In some embodiments, filters 154 may have a physical size and be made from a material having a pore size such that the overall opening facilitates the equalization of pressure across such filter 154 within approximately 0.25 seconds (with a range of between approximately 0.1 and 3 seconds) as tissue is drawn into tissue acquisition chamber 142. In some embodiments, filters 154 may have a physical size and be made from a material having a pore size which restricts the flow of air sufficiently to create a pressure differential between the air pressure in applicator chamber 118 and the air pressure in tissue acquisition chamber 142 during the time when air is flowing through filter 154. In some embodiments of the invention, filters 154 may act as air restrictors, restricting, but not eliminating the free flow of air between applicator chamber 118 and tissue acquisition chamber 142. In some embodiments, filters 154 may be positioned such that air pressure in tissue acquisition chamber 142 is greater than air pressure in applicator chamber 118 during periods when air is being drawn from tissue acquisition chamber 142 through applicator chamber 118, facilitating the positioning of a bio-barrier 152 against applicator tissue treatment surface 502 of applicator 114. In some embodiments, filters 154 may be positioned such that a vacuum in tissue acquisition chamber 142 is less than a vacuum in applicator chamber 118 during periods when air is drawn from tissue acquisition chamber 142 and applicator chamber 118, facilitating the positioning of a bio-barrier 152 against applicator tissue treatment surface 502 of applicator 114. In other embodiments, filters 154 may have a flow rate of a predetermined value when vacuum is applied. In one embodiment, filters 154 may have pore sizes of approximately 0.45 um and a flow area of approximately 1.86 square inches. In some embodiments, these measurements may vary by, for example, up to plus or minus twenty percent. Filter 154 may be, for example, PTFE on a polyester backing, polyethylene film, nylon or other material meeting the criteria set forth above.

The embodiments of the tissue interface modules illustrated in FIGS. 23 to 32 may include many of the features described herein with respect to prior described embodiments, including tissue interface module 116, applicator 114, vacuum channels 138, tissue acquisition chamber 142, filters 154, applicator chamber 118, electrical contacts 160, printed circuit board 162, attachment mechanism 126, engagement surfaces 125, gasket 158, gasket engagement surface 500, inner insert 192, outer shell 193, reflector 166, fluid trap 156, skirt 206, acquisition chamber opening 143 and vacuum interface 504 but omit the flexible bio-barrier 152 shown in earlier embodiments. Embodiments of tissue interface modules illustrated in FIGS. 23 through 32 may further include an intermediate gasket 600 (which may also be referred to as an intermediate sealing member) and one or more air passages 602 extending between tissue acquisition chamber 142 and fluid trap 156. Embodiments of applicators illustrated in FIGS. 23 to 32 may include many of the features described herein with respect to prior described embodiments, including cooling plate 128, applicator vacuum inlets 174, coolant conduits 185, tissue interface surface 200, magnetic extenders 179, magnet 186, sealing surface 121 and vacuum conduits 184. Tissue interface surface 200 may, in some embodiments of the invention comprise at least a portion of applicator tissue treatment surface 502.

Figure 27:
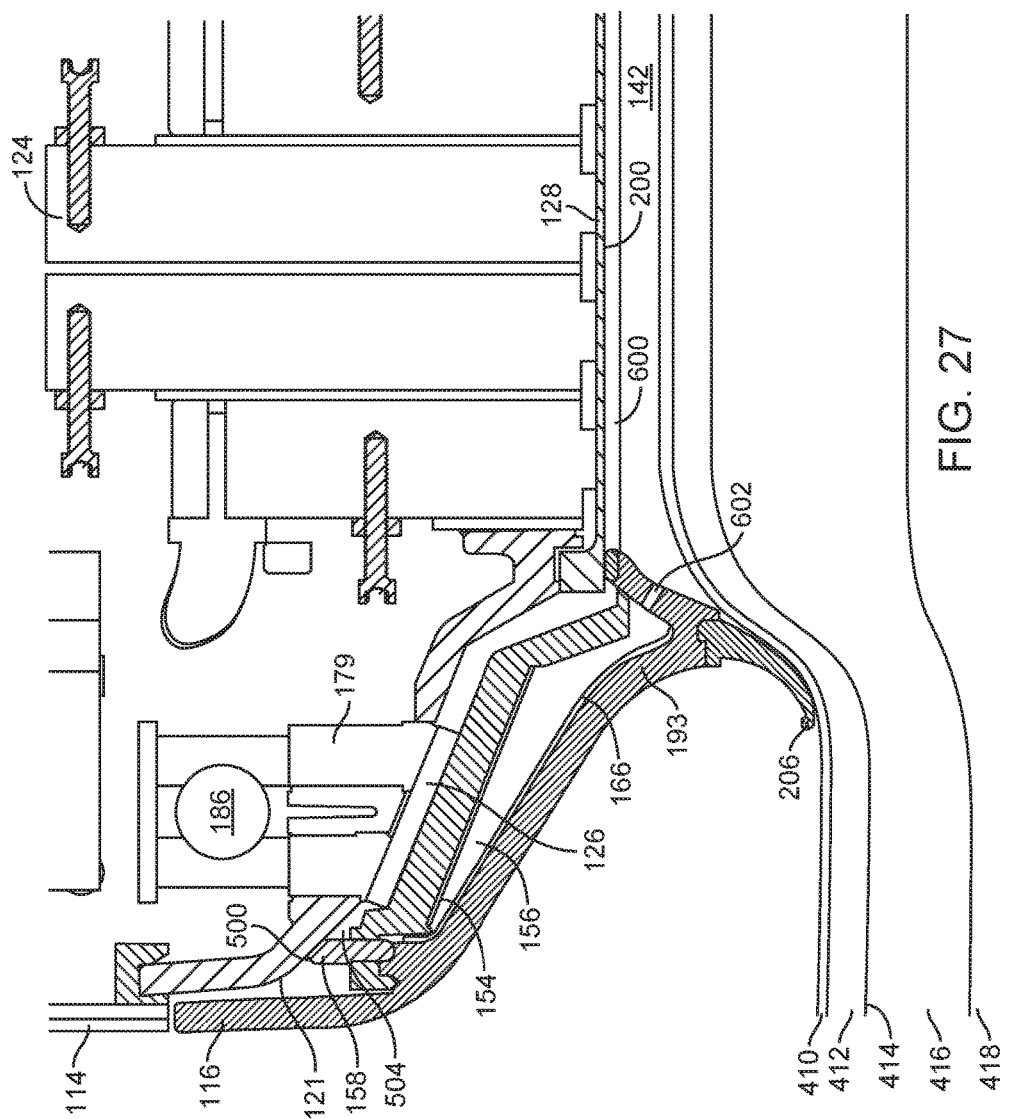
FIG. 27 illustrates a side cutaway view of a section of an applicator and a tissue interface module as tissue is pulled into a tissue acquisition chamber by applied vacuum.
Figure 28:
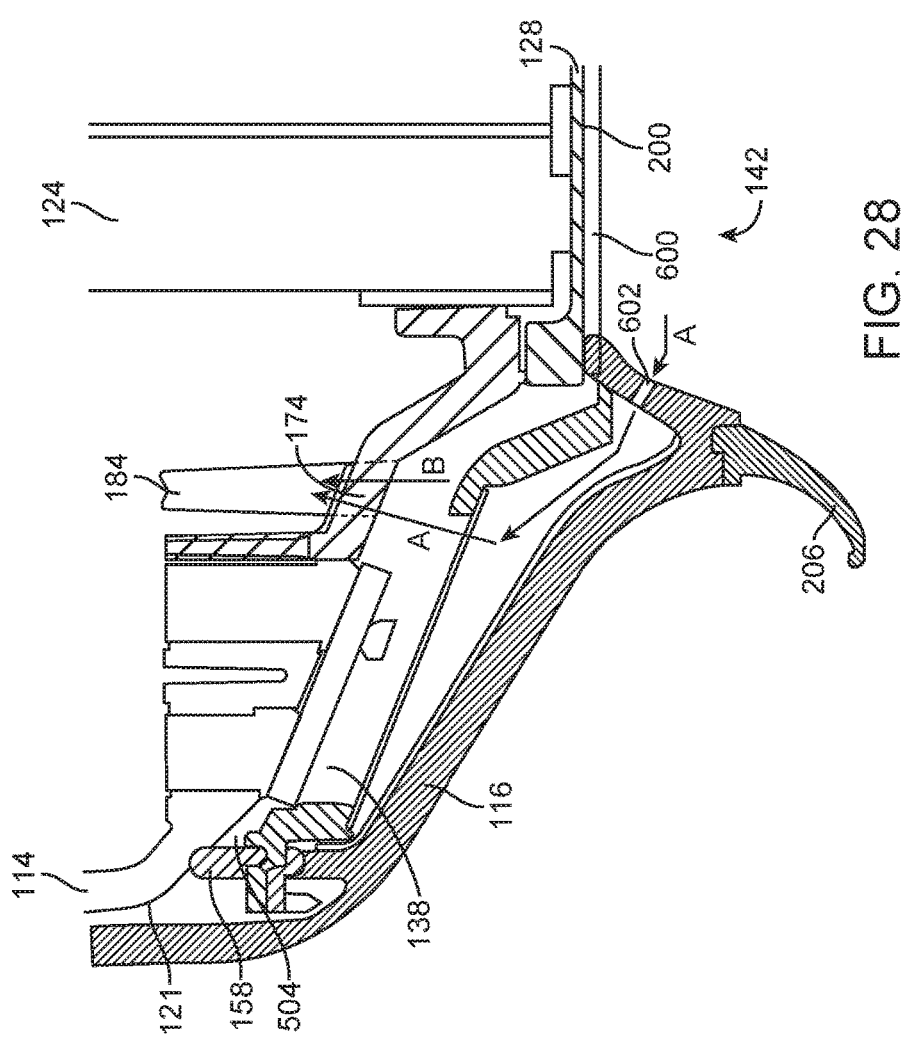
FIG. 28 shows a side cutaway view of a section of an applicator and a tissue interface module showing air paths with vacuum applied.
Figure 29:
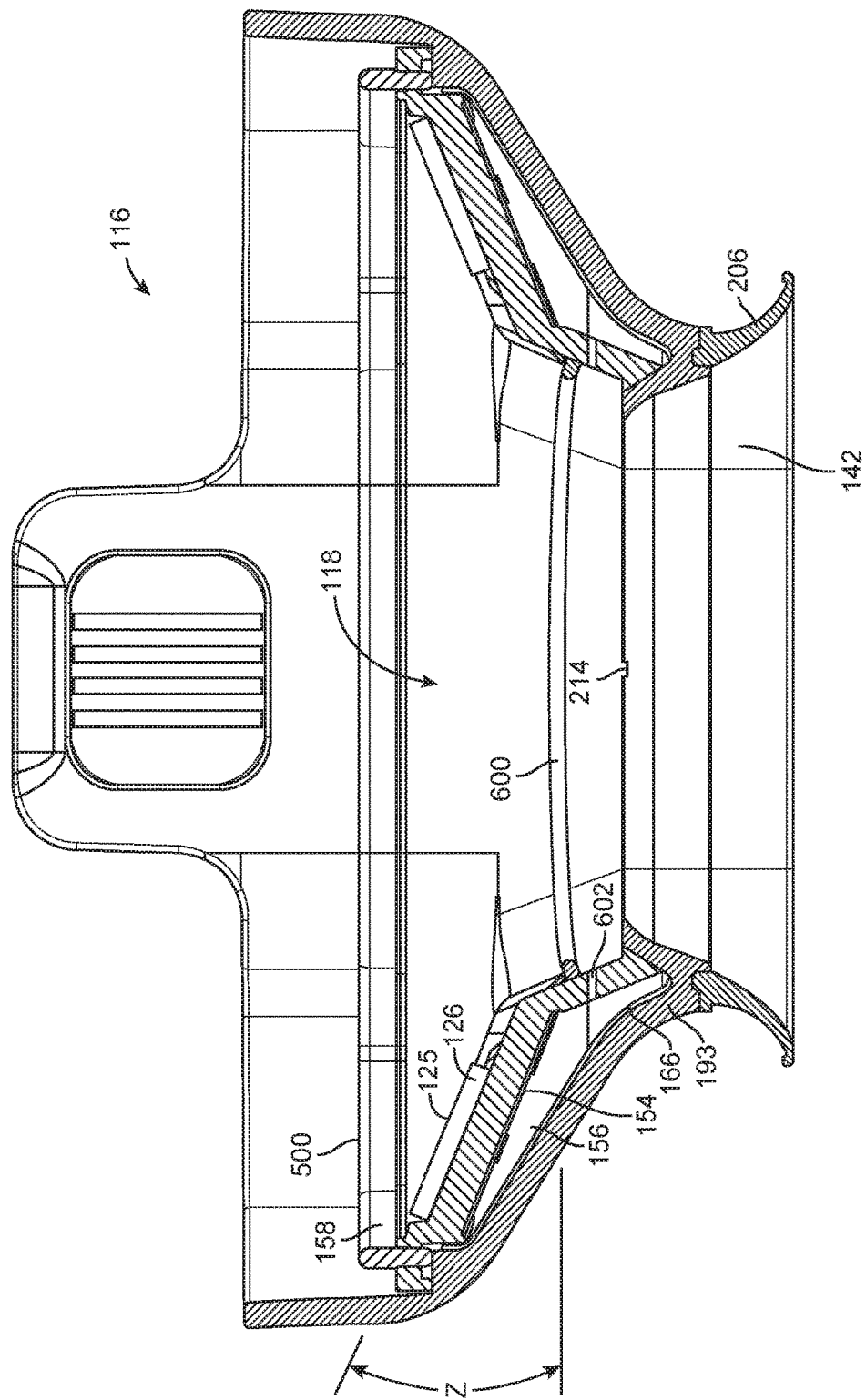
FIG. 29 shows a side cutaway view of a tissue interface module of another embodiment of the invention.
Figure 30:
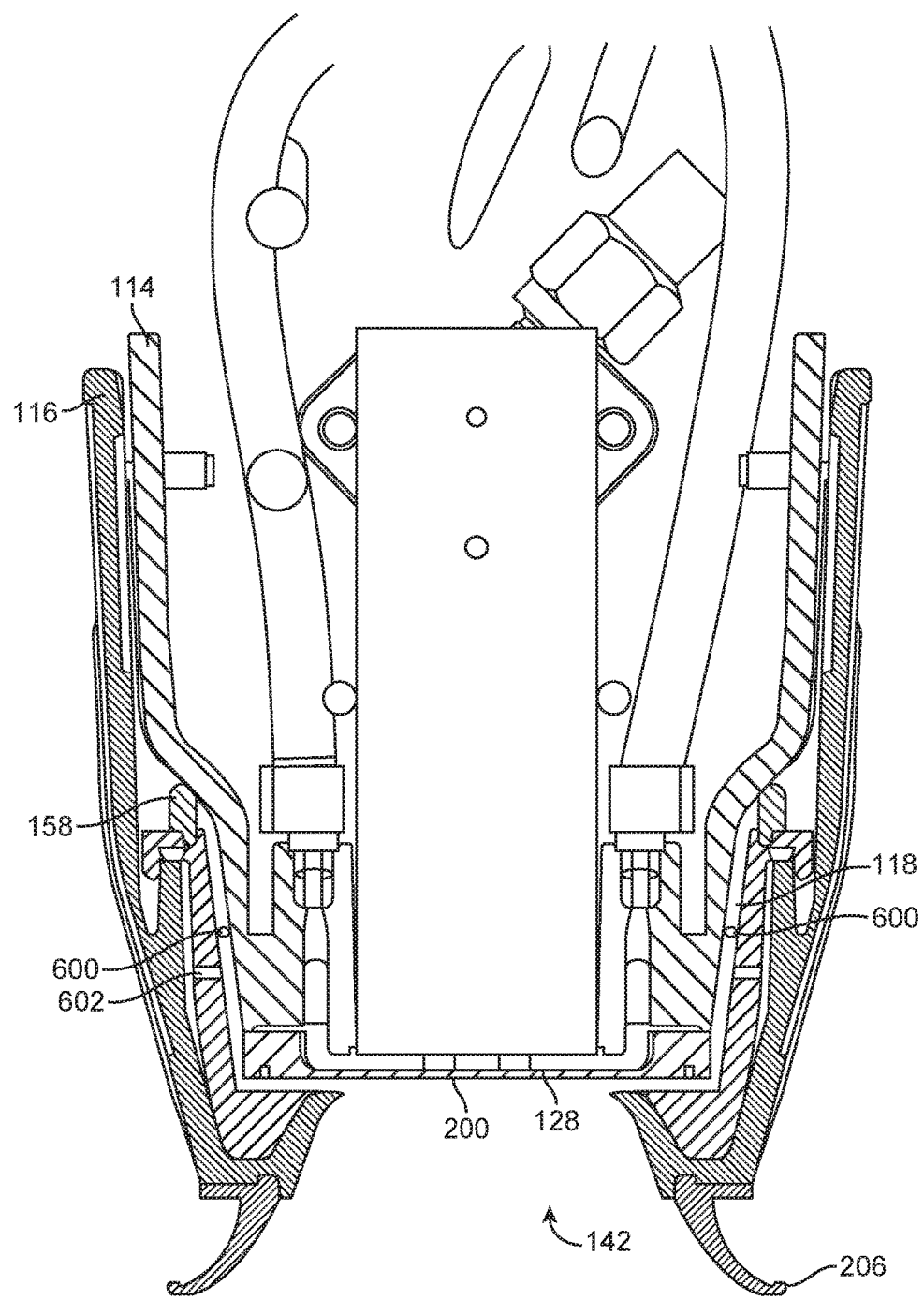
FIG. 30 shows a side cutaway view of a section of an applicator and a tissue interface module.
Figure 31:
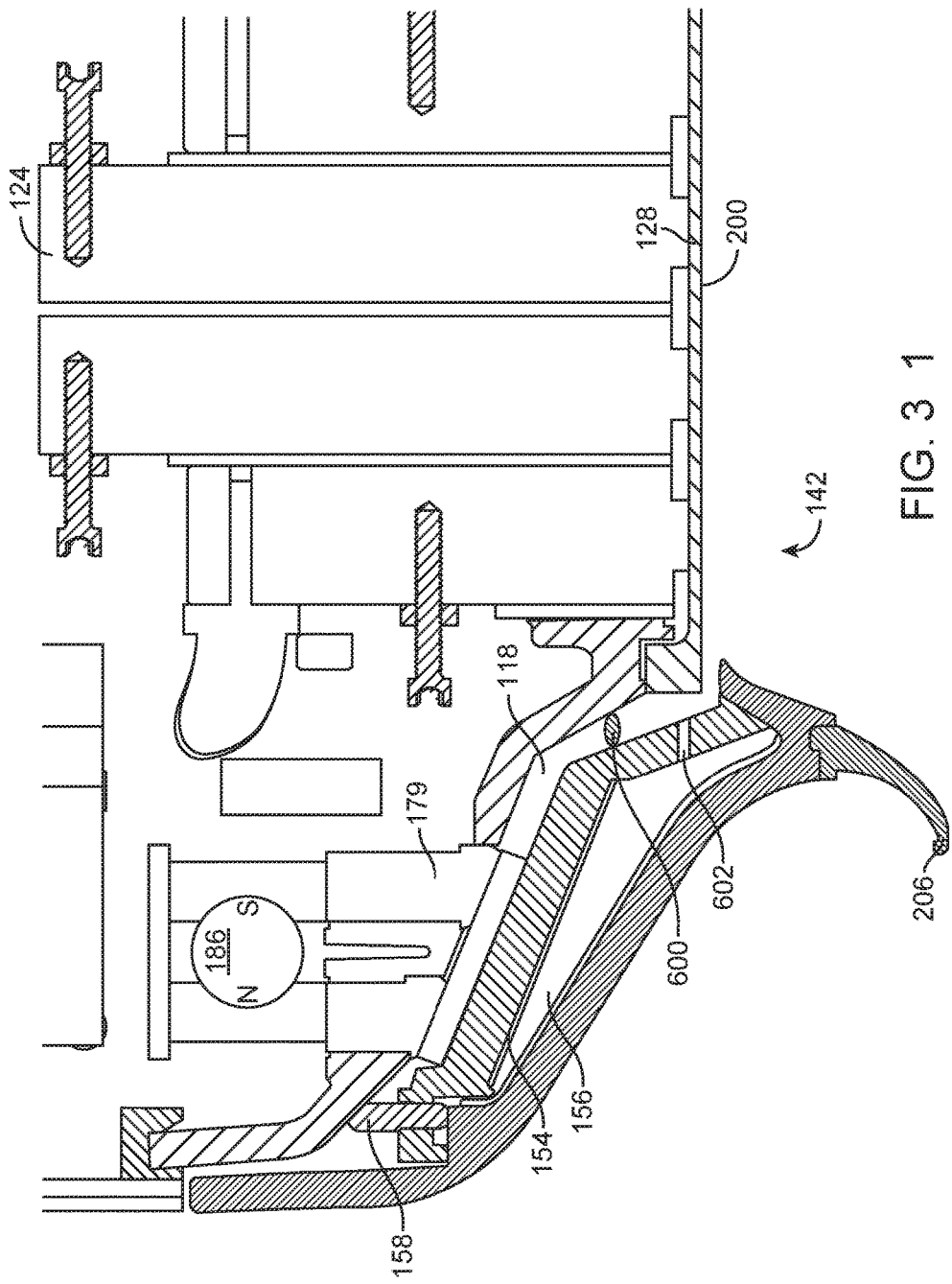
FIG. 31 is a side cutaway view of a portion of an applicator and a portion of a tissue interface module.
Figure 32:
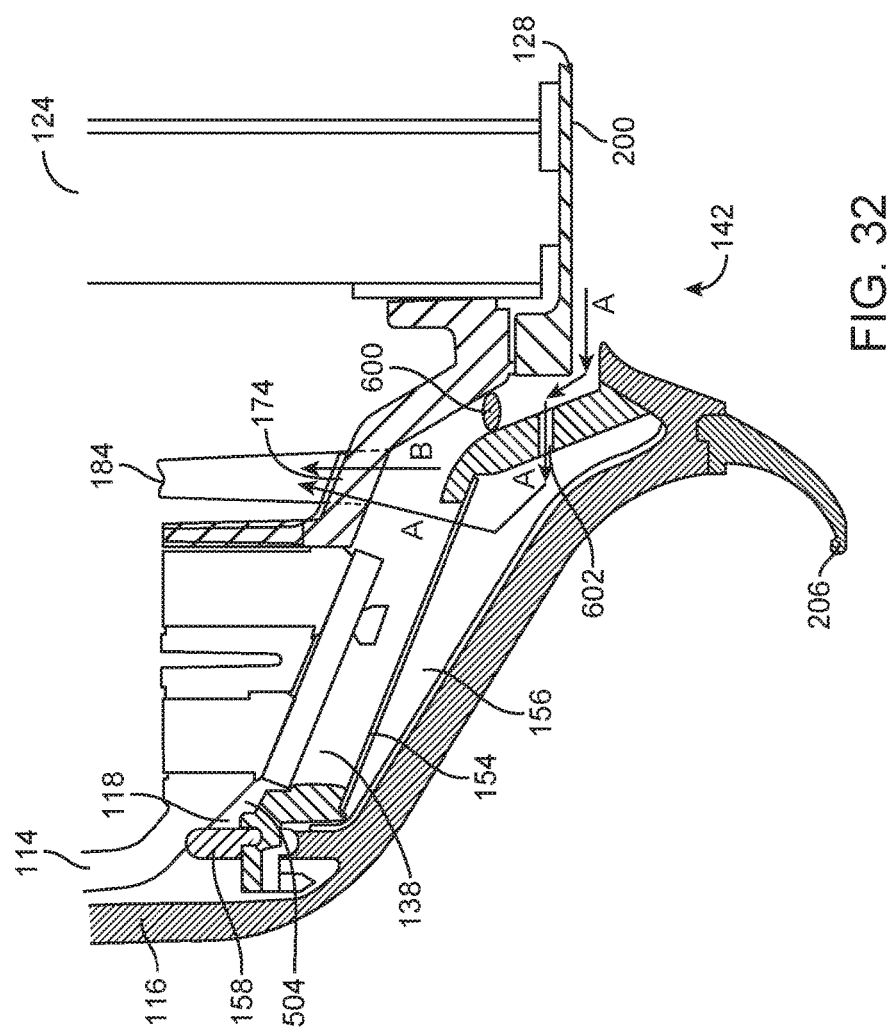
FIG. 32 shows a side cutaway view of a section of an applicator and a tissue interface module showing an air path with vacuum applied.

In embodiments of the invention, such as, for example, the embodiments illustrated in FIGS. 23 to 32, when tissue interface module 116 is attached to applicator 114, applicator vacuum inlets 174 are configured to be positioned in applicator chamber 118 (see, e.g., FIGS. 28 and 32) and to evacuate air from applicator chamber 118 through, for example, vacuum interface 504, creating a vacuum in applicator chamber 118. When positioned on applicator 114, embodiments of the tissue interface modules illustrated in FIGS. 23-32 provide a seal (see, for example, intermediate gasket 600) between tissue interface module 116 and applicator 114, thereby separating applicator chamber 118 from tissue acquisition chamber 142. This seal prevents air from flowing directly from tissue acquisition chamber 142 to applicator chamber 118, facilitating the flow of air through filter 154 and air passages 602 along air flow path A in FIGS. 28 and 32 when a vacuum is applied to applicator chamber 118, through, for example, vacuum interface 504. In these embodiments of the invention, air extracted from applicator chamber 118 will flow along path B as illustrated in FIGS. 28 and 32.

As shown in FIG. 27, when the skirt 206 of tissue interface module 116 is placed against a patient's skin surface, the vacuum created in tissue acquisition chamber 142 in response to movement of air along these flow paths A and B will draw the patient's skin and underlying tissue (including epidermis 410, dermis 412, dermal-hypodermal interface 414, hypodermis 416 and muscle 418) into tissue acquisition chamber 142 toward the applicator cooling plate 128. The flow restricting nature of filters 154 may, in some embodiments be used to ensure that the air pressure in tissue acquisition chamber 142 is higher than the air pressure in applicator chamber 118 until the patient's tissue ceases moving into tissue acquisition chamber 142, at which point the air pressures in the two chambers will equalize. In embodiments of the tissue interface module illustrated in, for example, FIGS. 23 through 28, intermediate seal, in the form of, for example, intermediate gasket 600 may be positioned such that, when attached to applicator 114 gasket 600 forms an air tight or substantially air tight seal against a surface of cooling plate 128. In embodiments of the tissue interface module 116 illustrated in, for example, FIGS. 29 through 32, intermediate seal, in the form of, for example, intermediate gasket 600 may be positioned such that, when attached to applicator 114 gasket 600 is adapted to form an air tight or substantially air tight seal against an outer surface of applicator 114. In embodiments of the invention illustrated in, for example FIGS. 29-32, air passages 602 may be positioned outside of tissue acquisition chamber 142 to reduce or eliminate the potential for air passages 602 to be blocked by tissue in tissue acquisition chamber 142. Some embodiments, such as, for example, those in FIG. 29 may also include vacuum notches 214 to facilitate the flow of air from tissue acquisition chamber 142 around the distal end of applicator 114 (when tissue interface module 116 is positioned on applicator 114) and into air passages 602.

Figure 23:
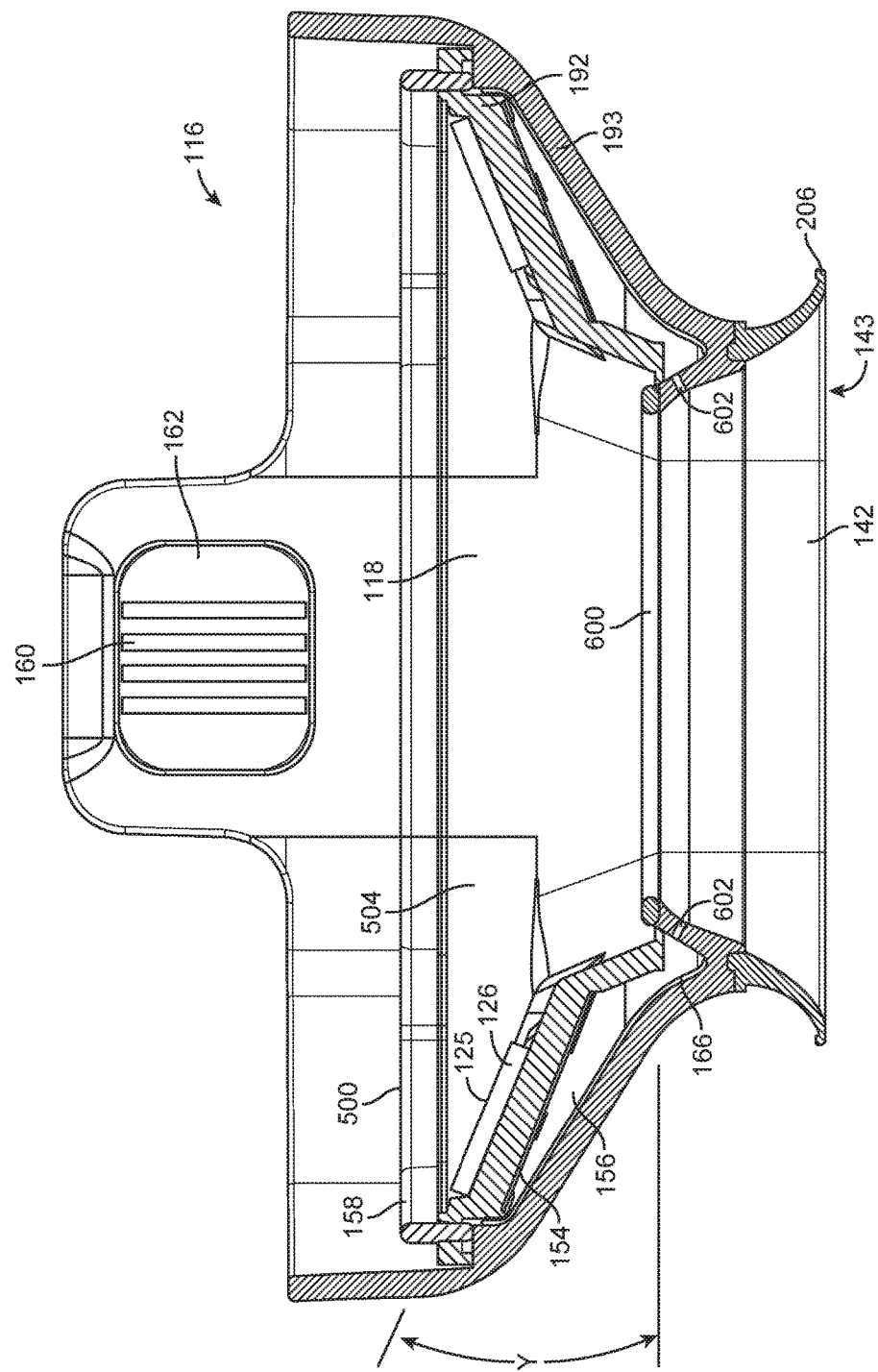
FIG. 23 shows a side cutaway view of a tissue interface module.
Figure 24:
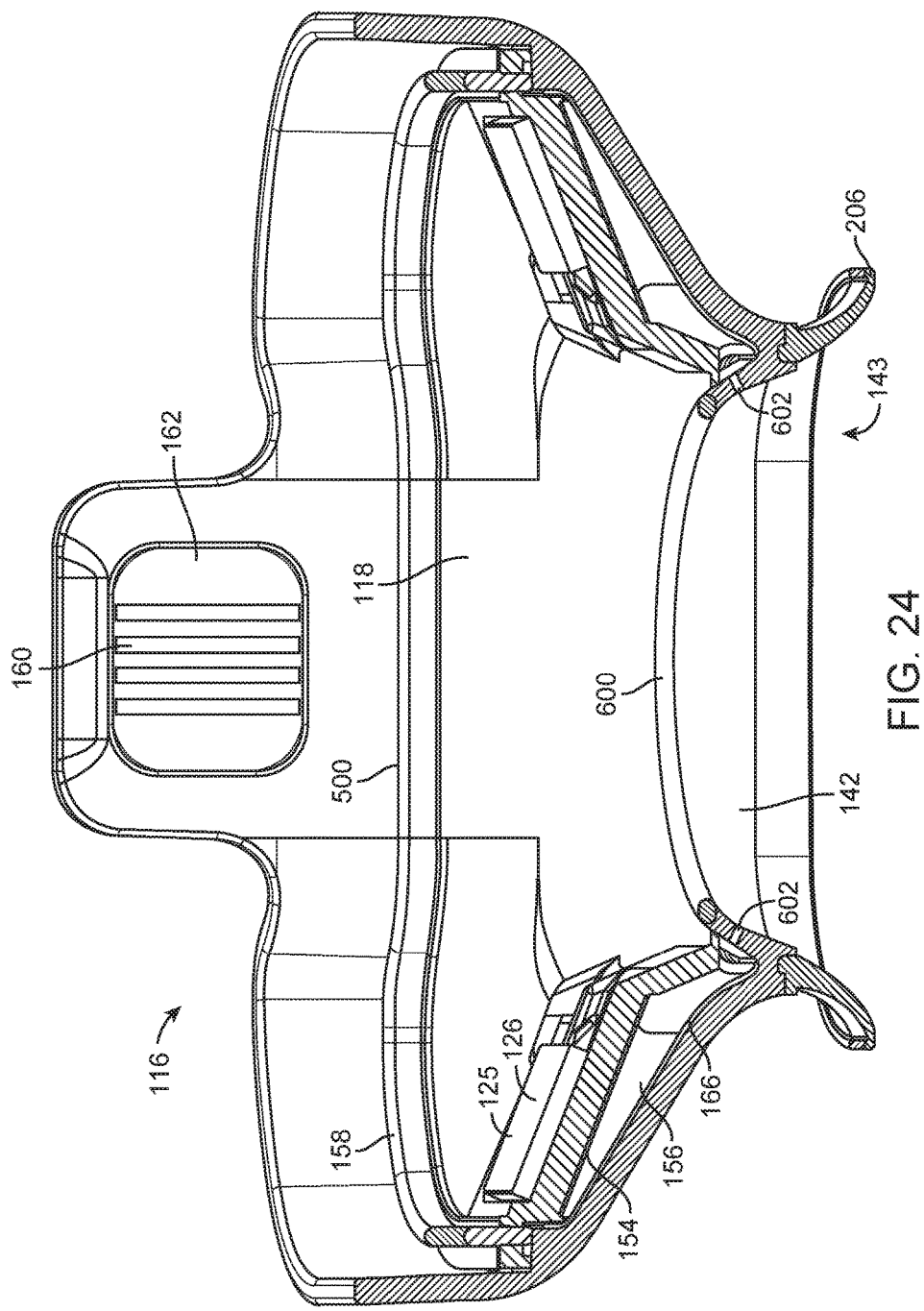
FIG. 24 illustrates a side cutaway perspective view of a tissue interface module.
Figure 25:
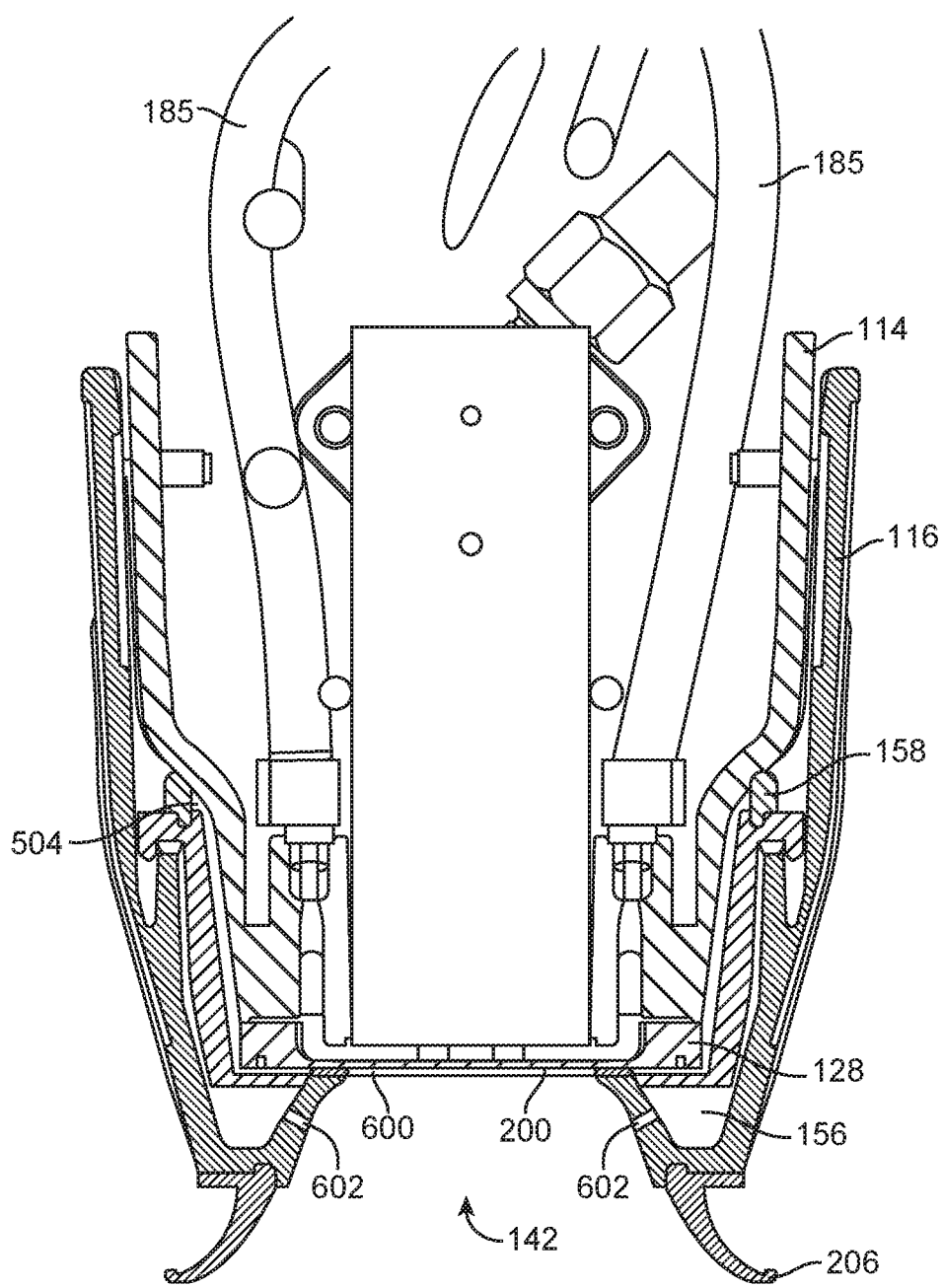
FIG. 25 illustrates an end cutaway view of a section of an applicator and a portion of a tissue interface module.
Figure 26:
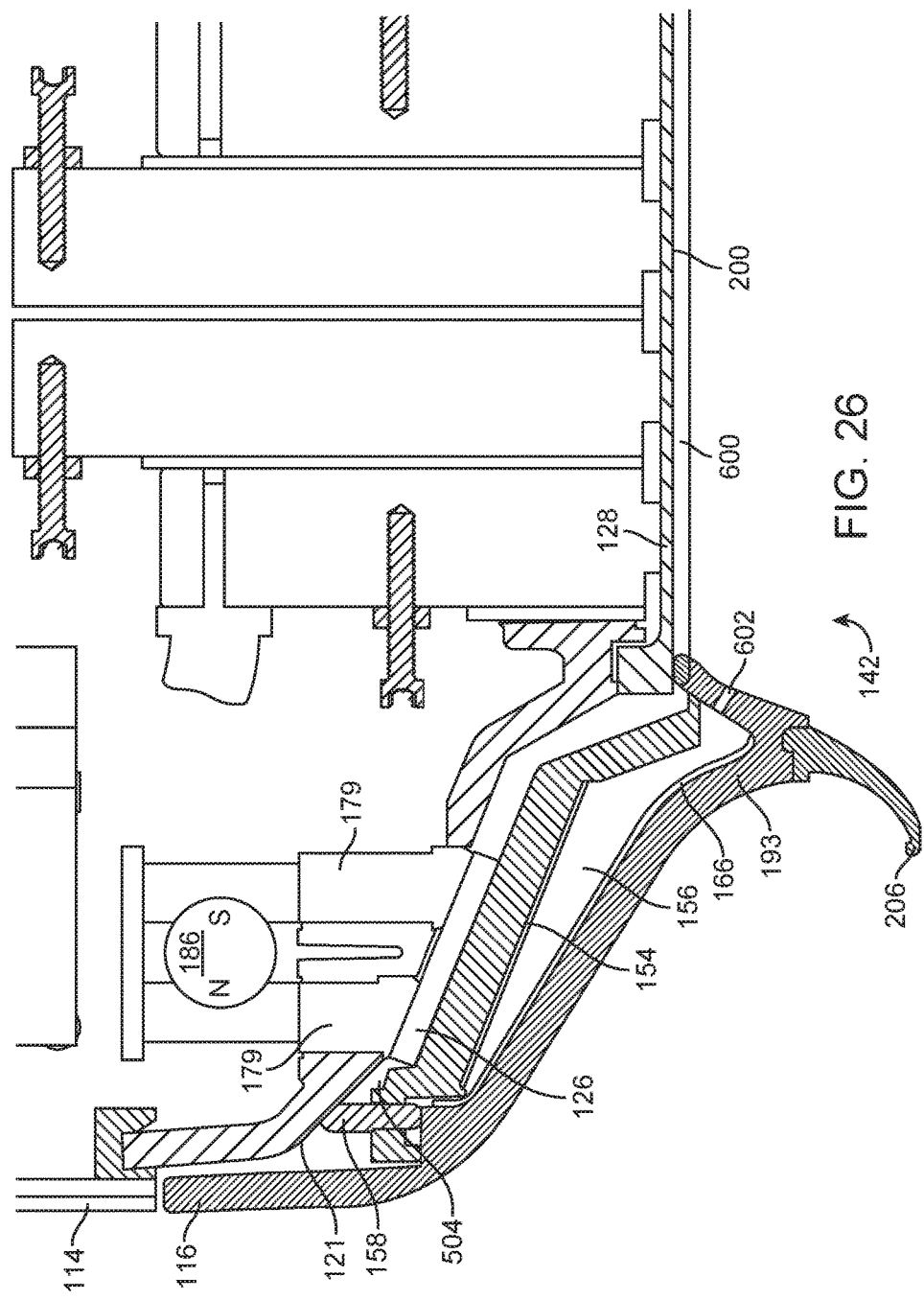
FIG. 26 is a side cutaway view of a portion of the applicator and a portion of a tissue interface module.

In the embodiments of the invention illustrated in FIG. 23, engagement surface 125 may form an Angle Y between engagement surface 125 and a plane passing through gasket 600. In the embodiments of the invention illustrated in FIG. 29, engagement surface 125 may form an Angle Z between engagement surface 125 and a plane passing through gasket 600. In other embodiments of the invention, Angles Y and Z may be measured between engagement surface 125 and a plane running through or parallel to the distal surface of cooling plate 128 when tissue interface module 116 is positioned on applicator 114. In embodiments of the invention, Angles Y and Z may be approximately 22.5 degrees. In embodiments of the invention, Angles Y and Z may be between approximately 17.5 degrees and 27.5 degrees, or alternatively, between approximately 12.5 degrees and 32.5 degrees. In other embodiments, Angles Y and Z may vary, up to and including 45 degrees or more, depending upon the angle chosen for the mating engagement surfaces on applicator 114.

In the embodiments of the invention illustrated in FIGS. 23 through 32, air flows through tissue interface module 116 when a vacuum is applied to vacuum interface 504 at the proximal end of the tissue interface module 116. With tissue interface module 116 positioned on applicator 114 and tissue engaged, as, for example, in FIG. 27, air trapped in tissue acquisition chamber 142 may flow, through the air passage A, including air passages 602, fluid trap 156, through filter 154 and vacuum channels 138, under attachment mechanism 126, through applicator chamber 118 to vacuum interface 504 and into vacuum inlet 174 in applicator 114. In embodiments of the invention, such as, for example, the embodiments illustrated in FIGS. 23-32, air may be prevented from bypassing filter 152 by the intermediate sealing member 600. In embodiments of the invention, such as, for example, the embodiments illustrated in FIGS. 1-22, air may be prevented from bypassing filter 152 by bio-barrier 152. Air in applicator chamber 118 flows along path B through vacuum interface 504 and into vacuum inlet 174.

Air flows through the interface module when a vacuum is applied to the vacuum interface at the proximal end of the tissue interface module. With the tissue interface module positioned on the applicator and no tissue engaged, air entering the tissue acquisition chamber flows into the tissue chamber, through the expandable aperture, into the vacuum trap, through the filter, under the engagement plate, through the applicator chamber to the vacuum interface and into the applicator. With the tissue interface module positioned on the applicator, and no tissue engaged, air in the applicator chamber flows through the applicator chamber to the vacuum interface and into the applicator.

With the distal end of the tissue interface module positioned against tissue, sealing the end of the tissue chamber from outside air, air in the tissue acquisition chamber is evacuated from the tissue acquisition chamber by flowing through the expandable channel, into the vacuum trap, through the filter, under the engagement plate, through the applicator chamber to the vacuum interface and into the applicator, creating a vacuum in the tissue acquisition chamber. The vacuum created in the tissue acquisition chamber pulls tissue into the tissue acquisition chamber, filling the tissue acquisition chamber. With the tissue interface module positioned on the applicator and tissue engaged, air in the applicator chamber flows through the applicator chamber to the vacuum interface and into the applicator, creating a vacuum in the applicator chamber.

With tissue engaged at the distal end of the tissue interface module, air evacuated from the tissue acquisition chamber must pass through a first vacuum path which includes the tissue acquisition chamber, the expandable aperture, the vacuum trap, the filter, a space under the engagement plate, the applicator chamber and the vacuum interface. With tissue engaged at the distal end of the tissue interface module, air evacuated from the applicator chamber must pass through a second vacuum path which includes the applicator chamber and the vacuum interface.

Air passing through the vacuum interface travels two pathways. Air in the applicator chamber flows through a first, direct pathway from the applicator chamber to the vacuum interface. Air in the tissue acquisition chamber travels a second, indirect, pathway which passes through the filter. The second, indirect pathway may further include one or more of: an expandable aperture; a vacuum trap, an applicator chamber and a vacuum interface.

The engagement and proper positioning of tissue is facilitated by positioning tissue at a distal end of a tissue acquisition chamber, forming a seal, pulling air from the tissue chamber though a pathway which includes in some embodiments a multifunction bio-barrier, the bio-barrier being composed of at least two parts. The first part of the bio-barrier may be substantially impermeable to air and fluids. The second part of the bio-barrier may be permeable to air but substantially impermeable to fluids. The first part of the multifunction bio-barrier may be a flexible bio-barrier which performs one or more of the following functions: preventing air from passing from the tissue acquisition chamber into the applicator chamber; preventing fluids from passing from the tissue acquisition chamber into the applicator chamber; diverting air being removed from the tissue chamber into a path which includes the second part of the multifunction bio-barrier; forming a substantially deformity free (e.g., no bubbles, voids or other deformities) seal against the distal end (e.g., cooling plate) of the applicator; forming at least one wall of an expandable aperture between the tissue acquisition chamber and the applicator chamber; and providing a pathway for energy and cooling to pass into tissue engaged in the tissue acquisition chamber. The second part of the multi-function bio-barrier may be one or more hydrophobic filters which performs one or more of the following functions: providing a pathway for air leaving the tissue acquisition chamber to enter the applicator chamber; preventing fluids (e.g., bodily fluids or lubricants) from passing from the tissue acquisition chamber into the applicator chamber; restricting the flow of air between the tissue acquisition chamber and the applicator chamber; ensuring that, at least while air is flowing from the tissue acquisition chamber to the applicator chamber, the air pressure in the tissue acquisition chamber is lower than the air pressure in the applicator chamber.

With tissue engaged at the distal end of the tissue interface module, air will flow through the first and second vacuum paths until tissue fills the tissue acquisition chamber. Airflow through the second vacuum path is restricted by the presence of the filter, resulting in a drop in air pressure across the filter such that the air pressure in the tissue acquisition chamber is lower than the air pressure in the applicator chamber. The presence of the filter ensures that this imbalance is maintained even in the presence of small air leaks in the seal between the applicator and the tissue interface module.

In embodiments employing a flexible bio-barrier, the presence of a vacuum imbalance with a higher pressure in the tissue acquisition chamber than in the applicator chamber forces the flexible bio-barrier against the distal end of the applicator and maintains the position of the flexible bio-barrier against the distal end of the applicator as tissue is drawn into the tissue acquisition chamber. The vacuum imbalance further assures that the flexible bio-barrier will sit against the distal end of the applicator without bubbles etc. until tissue fills the tissue acquisition chamber. Once the tissue acquisition chamber is filled, the presence of the tissue maintains the bio-barrier against the distal end of the applicator.

In embodiments employing a flexible bio-barrier, establishing and maintaining a substantially discontinuity-free (e.g., bubble-free) interface between the flexible bio-barrier and the distal end of the applicator is important for a number of reasons. It reduces the chances of a burn resulting from an air pocket. It enhances the transfer of cold energy from the cooling plate to the tissue. It eliminates the insulating effect of air trapped between the flexible bio-barrier and the cooling plate. It enhances the coupling of microwave energy from the applicator to the tissue. It reduces or eliminates discontinuities which might perturb the microwaves being radiated into the skin.

In embodiments employing a flexible bio-barrier, the presence of a vacuum imbalance with a higher pressure in the tissue acquisition chamber than in the applicator chamber pulls the flexible bio-barrier against the distal end of the applicator, opening the expandable aperture and increasing the cross section of the vacuum path at the expandable aperture. Opening the expandable aperture increases the size of the opening connecting the tissue acquisition chamber to the vacuum trap. Opening the expandable aperture increases the cross sectional area of the narrowest point in the airflow pathway between the tissue acquisition chamber and the vacuum trap. Opening the expandable aperture increases the cross sectional area of the narrowest point in the airflow pathway between the tissue acquisition chamber and the applicator chamber. Opening the expandable aperture facilitates the flow of air between the tissue acquisition chamber and the vacuum trap and reduces the chances that airflow between the tissue acquisition chamber and vacuum trap would be blocked by, for example, tissue, bodily fluids or lubricants.

In embodiments employing a flexible bio-barrier, the tissue interface module facilitates the efficient transfer of energy between the applicator and the tissue by ensuring that the flexible bio-barrier is pulled against the distal end of the applicator in a manner which minimizes discontinuities (e.g., bubbles) which could form between the distal end of the applicator and the flexible bio-barrier. The elimination of discontinuities is important because such discontinuities could: prevent the efficient cooling of the skin by insulating the skin under the discontinuity from the cooling plate; result in the creation of "hot spots" which might cause patient burns; change the "load" characteristics of the skin/cooling plate interface at the frequency of interest, thus reducing the efficiency of energy transfer and, potentially, the effectiveness of the treatment.

Energy is transmitted to tissue through a method which includes a series of steps. The series of steps may include one or more of the following: positioning a tissue interface module at a distal end of an applicator; attaching the tissue interface module to the applicator by closing a magnetic circuit, channeling magnetic flux through an engagement mechanism on the tissue interface module; positioning the tissue interface module so that the distal end of the tissue interface module is in contact with tissue such as, for example, skin; evacuating air from an applicator chamber at a proximal end of the tissue interface module; evacuating air from a tissue acquisition chamber through the applicator chamber; creating a pressure differential such that the air pressure in the applicator chamber is, during the tissue acquisition period (the period during which tissue is being pulled into the acquisition chamber), lower than the air pressure in the tissue acquisition chamber; pulling air through a filter as the air passes from the tissue acquisition chamber into the applicator chamber; pulling a flexible bio-barrier against a distal side of a cooling plate positioned at the distal end of the applicator; forming a substantially defect-, bubble- and void-free interface between the flexible bio-barrier and the distal end of the applicator; opening an expandable aperture positioned between the tissue acquisition chamber and the applicator chamber; pulling tissue into the tissue acquisition chamber by continuing to evacuate air from the applicator chamber.

Energy is transmitted through an applicator and a tissue interface module. The energy transmission path in the applicator may include: an antenna; at least one field spreader; a fluid channel; and a cooling plate. The energy transmission path in the tissue interface module may include: a vacuum interface, an applicator chamber; a flexible bio-barrier and a tissue acquisition chamber. In this embodiment, the energy is radiated through the center of the vacuum interface.

Applicator engages by placing engagement plates positioned in the applicator chamber against parallel surfaces at the end of magnetic extenders on the applicator such that magnetic the engagement plates close a magnetic circuit which includes a magnet, two magnetic extenders and the engagement plates. The engagement plates are positioned at an angle of 22.5 degrees to ensure that they will be parallel to and contact the ends of the magnetic extenders, creating the closed magnetic circuit. With the tissue interface module properly positioned and the engagement plates closing the magnetic circuit, the magnet may be positioned to enable magnetic flux to flow through the closed magnetic circuit exerting a magnetic force which holds the tissue interface module in place.

To facilitate the proper positioning of the tissue interface module prior to full engagement, the magnet may be positioned to generate a first magnetic force until the tissue interface module is properly seated, at which time, the magnet is moved in a manner which results in the application of a second magnetic force, wherein the second magnetic force is greater than the first magnetic force.

To facilitate the proper placement of the tissue interface module prior to full engagement, the flux density in the magnetic circuit may be set at a first level until the tissue interface module is properly positioned and may be increased once the tissue interface module is properly positioned.

Removal of the tissue interface module may be accomplished by reducing the magnetic force exerted on the tissue interface module. Removal of the tissue interface module may be accomplished by reducing the magnetic flux density through the magnetic circuit formed when the tissue interface module is attached to the applicator.

Air may be evacuated from the applicator chamber when the applicator and/or system detects the presence of a tissue interface module. A vacuum may be used to initially position and hold the tissue interface module prior to activation of the magnetic circuit.

One aspect of the invention provides a tissue interface module for use with an applicator in a microwave-based tissue modification system. The tissue interface module has an applicator chamber on a proximal side of the tissue interface module and a tissue acquisition chamber on a distal side of the tissue interface module. The applicator chamber may include: an opening adapted to receive the applicator; an attachment mechanism positioned in the applicator chamber and adapted to attach the tissue interface module to the applicator; a sealing member positioned at a proximal side of the applicator chamber; and a vacuum interface positioned at a proximal side of the applicator chamber and adapted to receive a vacuum inlet positioned on a distal end of the applicator. The tissue acquisition chamber may include a tissue acquisition opening on a distal side of the tissue interface module. The system may also include a flexible bio-barrier positioned between, and in fluid communication with, the applicator chamber and the tissue acquisition chamber, the flexible bio-barrier being substantially impermeable to air or fluids; an airflow pathway within the tissue interface module, the airflow pathway connecting the applicator chamber and the tissue acquisition chamber; and a filter disposed in the airflow pathway connecting the applicator chamber and the tissue acquisition chamber, the filter being permeable to air and substantially impermeable to fluids.

In some embodiments, the tissue interface module may also include a variable flow restrictor between, and in communication with, the tissue acquisition chamber and the filter. The variable flow restrictor may be positioned in the airflow pathway. The variable flow restrictor may be a flexible element adapted to expand a flow opening in the airflow pathway in response to a pressure difference between the tissue acquisition chamber and the filter.

In some embodiments, the sealing member forms at least a portion of the vacuum interface and is adapted to provide a substantially air tight seal against a sealing surface on the applicator when the tissue interface module is attached to the applicator with the attachment mechanism.

Another aspect of the invention provides a tissue interface module for use with an applicator in a microwave-based tissue modification system. The tissue interface module has an applicator chamber on a proximal side of the tissue interface module and a tissue acquisition chamber on a distal side of the tissue interface module. The applicator chamber may include: an opening adapted to receive an applicator; at least one attachment plate positioned in the applicator chamber, the attachment plate adapted to magnetically attach to elements of a magnetic circuit positioned on a distal end of the applicator; a sealing member positioned at a proximal side of the applicator chamber; a vacuum interface positioned at a proximal side of the applicator chamber and adapted to connect to a vacuum source. The tissue acquisition chamber may include a tissue acquisition opening on a distal side of the tissue interface module. The tissue interface module may also have a flexible bio-barrier positioned between, and in fluid communication with, the applicator chamber and the tissue acquisition chamber, the flexible bio-barrier being substantially impermeable to air or fluids; an airflow pathway within the tissue interface module, the airflow pathway connecting the applicator chamber and the tissue acquisition chamber; and a filter disposed in the airflow pathway connecting the applicator chamber and the tissue acquisition chamber, the filter being permeable to air and substantially impermeable to fluids.

In some embodiments, the attachment plate has a magnetic element adapted to form a magnetic circuit with magnetic elements in the applicator. The attachment plate may be, e.g., a ferromagnetic plate.

In some embodiments, the tissue interface module has a tissue interface module engagement surface adapted to engage with a corresponding applicator engagement surface on the applicator, the tissue interface module engagement surface being disposed at an angle of approximately 17.5 degrees to 27.5 degrees, such as approximately 22.5 degrees, with respect to the flexible bio-barrier. In some such embodiments, the attachment mechanism includes a ferromagnetic plate and the tissue interface module engagement surface includes a surface of the ferromagnetic plate.

Yet another aspect of the invention provides a tissue interface module for use with an applicator in a microwave-based tissue modification system. The tissue interface module has an applicator chamber on a proximal side of the tissue interface module and a tissue acquisition chamber on a distal side of the tissue interface module. The applicator chamber may include: an opening adapted to receive an applicator; an attachment mechanism positioned in the applicator chamber and adapted to attach the tissue interface module to the applicator; a sealing member positioned at a proximal side of the applicator chamber; and a vacuum interface positioned at the proximal side of the applicator chamber and adapted to connect to a vacuum source. The tissue acquisition chamber may have a tissue acquisition opening on a distal side of the tissue interface module. The tissue interface module may also have a flexible bio-barrier positioned between, and in fluid communication with, the applicator chamber and the tissue acquisition chamber, the flexible bio-barrier being substantially impermeable to air or fluids and may also be substantially transparent to microwave energy; a vacuum pathway within the tissue interface module, the vacuum pathway including an exit opening at a proximal end of the tissue acquisition chamber; and a filter disposed between the exit opening and the vacuum interface, the filter being permeable to air and substantially impermeable to fluids.

In some embodiments, the vacuum pathway extends from the distal end of the tissue acquisition chamber to the vacuum interface. The tissue interface module may also include a second filter disposed between, and communicating with, the applicator chamber and the tissue acquisition chamber, the second filter being permeable to air and substantially impermeable to fluids. In some such embodiments, the filter and the second filter are positioned on opposing sides of the bio-barrier. The functional surface area of the bio-barrier may also be approximately the same as the functional surface area of the filter and the second filter combined.

Still another aspect of the invention provides a tissue interface module having an applicator chamber on a proximal side and a tissue acquisition chamber on a distal side; a bio-barrier positioned between, and in fluid communication with, the applicator chamber and the tissue acquisition chamber, the bio-barrier being substantially impermeable, flexible, and microwave transparent; a vacuum path extending from a distal end of the tissue acquisition chamber to a proximal end of the applicator chamber and including a filter, a vacuum trap and an expandable aperture; the vacuum path being adapted to facilitate the flow of air from the tissue acquisition chamber, through the expandable aperture, through the vacuum trap, through the filter and into the applicator chamber when the applicator chamber is attached to a vacuum source.

In some embodiments, the tissue interface module also includes: an outer shell; an inner insert positioned in the outer shell to form a body of the tissue interface module; a gasket positioned on the inner insert and (i) providing a vacuum seal between the inner insert and the outer shell on a distal side of the gasket, (ii) being shaped to provide a vacuum seal to an applicator on a proximal side of the gasket, and (iii) forming a portion of the vacuum trap. The tissue interface module may also include a reflector (i) reflecting at least a portion of any microwave energy entering the applicator chamber; (ii) electrically isolated from an applicator positioned in the applicator chamber; (iii) positioned between the outer shell and the inner insert; and (iv) having a distal end surrounding at least a portion of the tissue acquisition chamber.

In some embodiments, the tissue interface module also has a latch plate positioned in the applicator chamber on the inner insert and including an attachment surface forming a predetermined angle with the bio-barrier when the bio-barrier is in a first position. The predetermined angle may be between 17.5 degrees and 27.5 degrees, such as approximately 22.5 degrees.

Yet another aspect of the invention provides a method of treating a patient including the following steps: attaching a tissue interface module to an applicator, wherein the distal end of the applicator is positioned in an applicator chamber of the tissue interface module; placing a distal opening of a tissue acquisition chamber of the tissue interface module against a tissue surface; pulling a portion of the patient's skin into the tissue acquisition chamber by creating a vacuum in the tissue acquisition chamber, the vacuum being created by drawing air from the tissue acquisition chamber to a vacuum source in the applicator through a vacuum path including the applicator chamber and a filter between the applicator chamber and the tissue acquisition chamber; and applying microwave energy to tissue positioned in the tissue acquisition chamber.

In some embodiments, the method also includes the step of cooling tissue in the tissue acquisition chamber during the application of microwave energy. In some embodiments, air is pulled from the tissue acquisition chamber, through the filter, into the applicator chamber and into a vacuum interface positioned on the distal end of the applicator.

In some embodiments, the applicator chamber and the tissue acquisition chamber are separated by, and in fluid communication with, a flexible bio-barrier. In such embodiments, the step of applying microwave energy can include the step of applying such energy through the flexible bio-barrier, and the step of pulling a portion of the patient's skin into the tissue acquisition chamber pulls the flexible bio-barrier against a distal end of the applicator.

In some embodiments, the method includes the step of varying a size of an opening between the tissue acquisition chamber and the filter during the step of creating a vacuum, such as by pulling the flexible bio-barrier against the distal end of the applicator.

Yet another aspect of the invention provides a method of treating a patient including the following steps: attaching a tissue interface module to an applicator, wherein the distal end of the applicator is positioned in an applicator chamber of the tissue interface module; placing a distal opening of a tissue acquisition chamber of the tissue interface module against a tissue surface; pulling a portion of the patient's skin into the tissue acquisition chamber by reducing the air pressure in the applicator chamber below the air pressure in the tissue acquisition chamber; and applying microwave energy to tissue positioned in the tissue acquisition chamber.

In some embodiments, the method also includes the step of drawing air from the tissue acquisition chamber to a vacuum source in the applicator through a vacuum path including the applicator chamber and a filter between the applicator chamber and the tissue acquisition chamber. In some such embodiments, air pressure in the applicator chamber is maintained at a pressure below the air pressure in the tissue acquisition chamber for at least as long as air continues to pass through the filter. Some embodiments also add the step of cooling tissue adjacent the bio-barrier during the application of microwave energy.

In some embodiments, the applicator chamber and the tissue acquisition chamber are separated by, and in fluid communication with, a flexible bio-barrier. In such embodiments, the step of applying microwave energy may include the step of applying such energy through the flexible bio-barrier, and the step of pulling a portion of the patient's skin into the tissue acquisition chamber may pull the flexible bio-barrier against a distal end of the applicator. In some embodiments, the step of reducing the air pressure in the applicator chamber includes the step of drawing air from the applicator chamber through a vacuum inlet at a proximal end of the applicator chamber via a vacuum interface at a distal end of the applicator.

Another aspect of the invention provides a method of treating a patient including the steps of: magnetically coupling a tissue interface module to an applicator, wherein the distal end of the applicator is positioned in an applicator chamber of the tissue interface module; placing a distal opening of a tissue acquisition chamber of the tissue interface module against a tissue surface; pulling a portion of the patient's skin into the tissue acquisition chamber by creating a vacuum in the tissue acquisition chamber, the vacuum being created by drawing air from the tissue acquisition chamber to a vacuum source in the applicator through a vacuum path that includes the applicator chamber and a filter between the applicator chamber and the tissue acquisition chamber; and applying microwave energy to tissue positioned in the tissue acquisition chamber.

In some embodiments, the step of magnetically coupling includes the steps of: sensing the presence of the tissue interface module in the proximity of the distal end of the applicator; evacuating air from the applicator chamber to position the tissue interface module on the applicator; and energizing a magnetic circuit to engage the tissue interface module to the applicator.

In some embodiments, the tissue interface module may have at least one engagement plate, and the applicator may include a magnetic circuit with at least two magnetic extenders arranged at a distal end of the applicator. In such embodiments, the step of positioning the tissue interface module may include the steps of placing the engagement plate in the proximity of the magnetic extenders and activating a magnetic circuit.

In some embodiments, the step of placing the engagement plate in the proximity of the magnetic extenders includes the step of placing an engagement surface of the engagement plate in contact with the magnetic extenders such that the engagement plate forms at least a portion of a magnetic circuit with the magnetic extenders. In some such embodiments, the step of activating the magnetic circuit includes the step of increasing the magnetic force applied to the engagement surface.

In some embodiments, a bio-barrier separates the applicator chamber from the tissue acquisition chamber, the tissue interface module engagement surface being disposed at an angle of approximately 22.5 degrees with respect to the flexible bio-barrier.

Yet another aspect of the invention provides a method of treating tissue of a patient, the method including the following steps: mating a tissue interface module to an applicator to place the distal end of a microwave antenna, a cooling plate, and a vacuum inlet within an applicator chamber of the tissue interface module; actuating a magnet to complete a magnetic circuit between an attachment mechanism of the tissue interface module and the applicator; placing a distal opening of a tissue acquisition chamber of the tissue interface module against a tissue surface; drawing a vacuum from a vacuum source in the applicator through the applicator chamber, a filter between the applicator chamber and the tissue acquisition chamber; and applying microwave energy to the patient's tissue.

Still another aspect of the invention provides a method of pulling air through a consumable medical device, the method including the steps of: creating a vacuum in an applicator chamber of said consumable medical device, the applicator chamber being separated from a tissue acquisition chamber by a bio-barrier, the bio-barrier being flexible and impermeable to bodily fluids and air; pulling air into the applicator chamber from a vacuum trap through a filter, the filter being permeable to air but substantially impermeable to bodily fluids; pulling air into the vacuum trap through an expandable aperture, wherein the expandable aperture (i) substantially surrounds the tissue acquisition chamber, (ii) is formed at least in part by the bio-barrier, (iii) opens upon the application of vacuum to the applicator chamber, which pulls said bio-barrier into the applicator chamber and against a cooling plate; creating a vacuum in said tissue acquisition chamber; and pulling tissue positioned outside said tissue acquisition chamber into said tissue acquisition chamber using said vacuum created in said tissue acquisition chamber.

Another aspect of the invention provides a tissue interface module for use with an applicator in a microwave-based tissue modification system. The tissue interface module may include an applicator chamber adapted to receive the applicator; a vacuum interface adapted to connect the applicator chamber with a vacuum source; a tissue acquisition chamber with an opening adapted to be applied to a patient's tissue; an airflow path between the tissue acquisition chamber and the vacuum interface; and a flow restrictor (such as, e.g., an air filter) disposed in the airflow path such that air pressure in the tissue acquisition chamber is greater than air pressure in the applicator chamber when air is moving from the applicator chamber through the vacuum interface to a vacuum source.

In some embodiments, the tissue interface module also includes a flexible bio-barrier positioned between, and in fluid communication with, the applicator chamber and the tissue acquisition chamber, with the flexible bio-barrier being substantially impermeable to air or fluids. In some such embodiments, the tissue interface module may also include an expandable aperture disposed in the airflow path, the expandable aperture formed at least in part by the flexible bio-barrier. The expandable aperture may be disposed in a portion of the airflow path between the tissue acquisition chamber and the flow restrictor.

Yet another aspect of the invention provides a method of treating a patient including the following steps: placing a distal end of an applicator into an applicator chamber of a tissue interface module; placing a distal opening of a tissue acquisition chamber of the tissue interface module against a skin surface of the patient; applying vacuum from a vacuum source to the applicator chamber; applying vacuum to the tissue acquisition chamber from the applicator chamber through a flow restrictor so that the air pressure in the tissue acquisition chamber is higher than the air pressure in the applicator chamber while air is flowing out of the tissue interface module through the vacuum interface; and applying microwave energy from the applicator to the skin surface.

In some embodiments, the applicator chamber and the tissue acquisition chamber are separated by, and in fluid communication with, a flexible bio-barrier, and the method further includes the step of moving the flexible bio-barrier against a distal end of the applicator. The flexible bio-barrier may also form part of an aperture between the tissue acquisition chamber and the applicator chamber, and the step of moving the flexible bio-barrier may include the step of expanding the aperture.

In some embodiments, the flow restrictor includes a filter disposed in an airflow path between the tissue acquisition chamber and the applicator chamber. The method may also include the step of pulling a portion of the skin surface into the tissue acquisition chamber prior to the step of applying microwave energy.

Still another aspect of the invention provides a method of treating a patient including the following steps: placing a distal end of an applicator into an applicator chamber of a tissue interface module; placing a distal opening of a tissue acquisition chamber of the tissue interface module against a skin surface of the patient; reducing air pressure in the applicator chamber at a first rate; reducing air pressure in the tissue acquisition chamber at a second rate slower than the first rate so that the air pressure in the tissue acquisition chamber is higher than the air pressure in the applicator chamber; and applying microwave energy from the applicator to the skin surface.

In some embodiments, the applicator chamber and the tissue acquisition chamber are separated by, and in fluid communication with, a flexible bio-barrier, and the method further includes the step of moving the flexible bio-barrier against a distal end of the applicator. The flexible bio-barrier may also form part of an aperture between the tissue acquisition chamber and the applicator chamber, and the step of moving the flexible bio-barrier may include the step of expanding the aperture.

In some embodiments, the flow restrictor includes a filter disposed in an airflow path between the tissue acquisition chamber and the applicator chamber. The method may also include the step of pulling a portion of the skin surface into the tissue acquisition chamber prior to the step of applying microwave energy.

Another aspect of the invention provides a tissue interface module for use with an applicator in a microwave-based tissue modification system, the tissue interface module having an applicator chamber on a proximal side of the tissue interface module, the applicator chamber having an opening adapted to receive the applicator; an attachment mechanism positioned in the applicator chamber and adapted to attach the tissue interface module to the applicator; a proximal sealing member positioned at a proximal side of the applicator chamber and adapted to provide a first seal between the tissue interface module and the applicator when the tissue interface module is attached to the applicator; a vacuum interface positioned at a proximal side of the applicator chamber; a tissue acquisition chamber including a tissue acquisition opening on a distal side of the tissue interface module; a central opening between the applicator chamber and the tissue acquisition chamber; an intermediate sealing member surrounding the central opening and adapted to provide a second seal between the tissue interface module and the applicator and to prevent fluid flow through the central opening; an airflow pathway within the tissue interface module, the airflow pathway connecting the applicator chamber and the tissue acquisition chamber, the airflow pathway bypassing the intermediate sealing member and the central opening; and a filter disposed in the airflow pathway, the filter being permeable to air and substantially impermeable to fluids.

In some embodiments, the vacuum interface is adapted to receive a vacuum inlet positioned on a distal end of the applicator. The proximal sealing member may optionally form at least a portion of the vacuum interface.

In some embodiments, the second seal includes a seal between the tissue interface module and a cooling plate positioned at a distal end of the applicator. The tissue interface module may also include a distal sealing member positioned at the tissue acquisition opening.

Yet another aspect of the invention provides a tissue interface module for use with an applicator in a microwave-based tissue modification system. The tissue interface module may include: an applicator chamber on a proximal side of the tissue interface module, the applicator chamber having an opening adapted to receive an applicator; at least one attachment plate positioned in the applicator chamber, the attachment plate positioned to engage with elements of a magnetic circuit positioned on a distal end of the applicator; a proximal sealing member positioned at a proximal side of the applicator chamber and adapted to provide a first seal between the tissue interface module and the applicator when the tissue interface module is attached to the applicator; a vacuum interface positioned at a proximal side of the applicator chamber and adapted to connect to a vacuum source; a tissue acquisition chamber including a tissue acquisition opening on a distal side of the tissue interface module; a central opening between the applicator chamber and the tissue acquisition chamber; an intermediate sealing member surrounding at least a portion of the central opening and adapted to provide a second seal between the tissue interface module and the applicator and to prevent fluid flow through the central opening; an airflow pathway within the tissue interface module, the airflow pathway connecting the applicator chamber and the tissue acquisition chamber, the airflow pathway bypassing the intermediate sealing member and the central opening; and a filter disposed in the airflow pathway, the filter being permeable to air and substantially impermeable to fluids.

In some embodiments, the attachment plate includes a magnetic element (such as, e.g., a ferromagnetic plate) adapted to form a magnetic circuit with magnetic elements in the applicator.

In some embodiments, the tissue interface module has a tissue interface module engagement surface adapted to engage with a corresponding applicator engagement surface on the applicator, the tissue interface module engagement surface being disposed at an angle of approximately 22.5 degrees with respect to a plane containing the intermediate sealing member. In some such embodiments, the attachment plate mechanism includes a ferromagnetic plate and the tissue interface module engagement surface includes a surface of the ferromagnetic plate.

In some embodiments, the tissue interface has a tissue interface module engagement surface adapted to engage with a corresponding applicator engagement surface on the applicator, the tissue interface module engagement surface being disposed at an angle of between approximately 17.5 degrees and approximately 27.5 degrees with respect to a plane containing the intermediate sealing member.

Still another aspect of the invention provides a tissue interface module for use with an applicator in a microwave-based tissue modification system, the tissue interface module including: an applicator chamber on a proximal side of the tissue interface module, the applicator chamber having an opening adapted to receive an applicator; an attachment mechanism positioned in the applicator chamber and adapted to attach the tissue interface module to the applicator; a proximal sealing member positioned at a proximal side of the applicator chamber and adapted to provide a first seal between the tissue interface module and the applicator when the tissue interface module is attached to the applicator; a vacuum interface positioned at a proximal side of the applicator chamber; a tissue acquisition chamber on a distal side of the tissue interface module, the tissue acquisition chamber having a tissue acquisition opening on a distal side of the tissue interface module and a central opening between the applicator chamber and the tissue acquisition chamber; an intermediate sealing member surrounding at least a portion of the central opening and adapted to provide a second seal between the tissue interface module and the applicator and to prevent fluid flow through the central opening; a vacuum pathway within the tissue interface module, the vacuum pathway including a first opening on a first side of the intermediate sealing member, a second opening on a second side of the intermediate sealing member; and a filter disposed between the first and second openings, the filter being permeable to air and substantially impermeable to fluids; wherein the vacuum pathway extends through the filter from a first side of the intermediate sealing member to a second side of the intermediate sealing member when fluid flow through the central opening is prevented. In some embodiments, with the tissue interface module affixed to the applicator, the vacuum flow path begins at the distal end of the tissue acquisition chamber and terminates at the vacuum interface.

Another aspect of the invention provides a tissue interface module having: an applicator chamber positioned on a proximal side of said tissue interface module; a tissue acquisition chamber positioned on a distal side of said tissue interface module; a central opening; an intermediate sealing member surrounding at least a portion of the central opening and adapted to provide a seal between the tissue interface module and the applicator and to prevent fluid flow through the central opening; a vacuum path extending from a proximal side of the intermediate sealing member to a distal side of the intermediate sealing member, the vacuum path including a filter and a vacuum trap; wherein the vacuum path is adapted to facilitate the flow of air from the tissue acquisition chamber, through the vacuum trap, through the filter and into the applicator chamber when the applicator chamber is attached to the applicator vacuum port when fluid flow through the central opening is prevented.

Yet another aspect of the invention provides a method of treating a patient including the following steps: positioning a distal end of an applicator in an applicator chamber of a tissue interface module; sealing a central opening between the applicator chamber and a tissue acquisition chamber of the tissue interface module against the distal end of the applicator; applying a vacuum to the applicator chamber; placing a distal opening of a tissue acquisition chamber of the tissue interface module against a tissue surface; pulling a portion of the patient's tissue into the tissue acquisition chamber by creating a vacuum in the tissue acquisition chamber, the vacuum being created by drawing air from the tissue acquisition chamber to a vacuum source in the applicator through a vacuum path comprising the applicator chamber and a filter between the applicator chamber and the tissue acquisition chamber; and applying microwave energy to tissue positioned in the tissue acquisition chamber.

In some embodiments, the method also includes the step of cooling the tissue in the acquisition chamber. The method may also include the step of sealing the applicator chamber against the applicator at a vacuum interface.

In some embodiments, the method includes the step of magnetically attaching the tissue interface module to the applicator such as, e.g., by forming a magnetic circuit between elements of the applicator and the tissue interface module.

Another aspect of the invention provides a tissue interface module for use with an applicator in a microwave-based tissue modification system, the tissue interface module including: an attachment mechanism on a proximal side of the tissue interface module adapted to attach to an applicator; an applicator chamber adapted to receive a microwave antenna, a cooling element, and a vacuum port of the applicator, the applicator chamber comprising a bio-barrier on a distal side; a tissue acquisition chamber having a tissue acquisition opening on a distal side of the tissue interface module; and a filter disposed between, and communicating with, the applicator chamber and the tissue acquisition chamber, the filter having openings configured to permit air to pass and to prevent liquid from passing.

In some embodiments, the tissue interface module also has a variable flow restrictor between, and in communication with, the tissue acquisition chamber and the filter. The variable flow restrictor may have a flexible element adapted to expand a flow opening between the tissue acquisition chamber and the filter in response to a pressure difference between the tissue acquisition chamber and the filter.

In some embodiments, the attachment mechanism has a magnetic element (such as, e.g., a ferromagnetic plate) adapted to magnetically attach to a corresponding element in the applicator. The tissue interface module may also have a tissue interface module engagement surface adapted to engage with a corresponding applicator engagement surface on the applicator, the tissue interface module engagement surface being disposed at an angle of approximately 12.5 degrees to 32.5 degrees, or approximately 17.5 degrees to 27.5 degrees, or approximately 22.5 degrees, with respect to the bio-barrier.

In some embodiments, the tissue interface module also has a vacuum flow path from the tissue acquisition chamber, through the filter, into the applicator chamber. In some embodiments, the tissue interface module has a vacuum flow path from the tissue acquisition chamber, through the filter, through the applicator chamber, into the vacuum port of the applicator.

In some embodiments, the tissue interface module may also have a second filter disposed between, and communicating with, the applicator chamber and the tissue acquisition chamber, the second filter having openings configured to permit air to pass and to prevent liquid from passing. In some such embodiments, the filter and the second filter are positioned on opposing sides of the bio-barrier. The bio-barrier may have approximately the same surface area as the filter and the second filter combined.

Another aspect of the invention provides a method of treating tissue of a patient including the following steps: attaching a tissue interface module to an applicator to place a microwave antenna, a cooling plate, and a vacuum port within an applicator chamber of the tissue interface module; placing a distal opening of a tissue acquisition chamber of the tissue interface module against a tissue surface; drawing a vacuum from a vacuum source in the applicator through the applicator chamber, a filter between the applicator chamber and the tissue acquisition chamber; and applying microwave energy to the patient's tissue.

Some embodiments add the step of varying a size of an opening between the tissue acquisition chamber and the filter during the step of drawing a vacuum, such as by moving a flexible member to change the size of the opening. In some embodiments, the attaching step includes the step of magnetically coupling the tissue interface module to the applicator.

In some embodiments, the applicator chamber has a bio-barrier on a distal side, and the attaching step includes the step of engaging a magnetic tissue interface module engagement surface with a corresponding applicator engagement surface on the applicator, the tissue interface module engagement surface being disposed at an angle of approximately 17.5 degrees to 27.5 degrees with respect to the bio-barrier.

Still another aspect of the invention provides a microwave-based tissue modification system having: a microwave applicator with a microwave antenna, a cooling element, and a vacuum port; and a tissue interface module with: an attachment mechanism on a proximal side of the tissue interface module adapted to attach to the microwave applicator; an applicator chamber adapted to connect to the microwave antenna, the cooling element, and the vacuum port of the microwave applicator, the applicator chamber having a bio-barrier on a distal side; a tissue acquisition chamber having a tissue acquisition opening on a distal side of the tissue interface module; and a filter disposed between, and communicating with, the applicator chamber and the tissue acquisition chamber, the filter having openings configured to permit air to pass and to prevent liquid from passing.

In some embodiments, the tissue modification system also has a variable flow restrictor between, and in communication with, the tissue acquisition chamber and the filter. In some embodiments, the attachment mechanism includes a magnetic element adapted to magnetically attach to a corresponding element in the applicator. The tissue modification system may also include a tissue interface module engagement surface adapted to engage with a corresponding applicator engagement surface on the microwave applicator, the tissue interface module engagement surface being disposed at an angle of approximately 17.5 degrees to 27.5 degrees with respect to the bio-barrier.

In some embodiments, the tissue modification system has a vacuum flow path from the tissue acquisition chamber, through the filter, through the applicator chamber, into the vacuum port of the microwave applicator. The tissue interface module may also have a second filter disposed between, and communicating with, the applicator chamber and the tissue acquisition chamber, the second filter having openings configured to permit air to pass and to prevent liquid from passing. In some such embodiments, the filter and the second filter are positioned on opposing sides of the bio-barrier.

Yet another aspect of the invention provides a tissue interface module for use with an applicator in a microwave-based tissue modification system, the tissue interface module having: an attachment mechanism on a proximal side of the tissue interface module adapted to attach to an applicator, the attachment mechanism including an engagement surface that forms an angle of approximately 17.5 degrees to 27.5 degrees from horizontal; an applicator chamber adapted to connect to a microwave antenna, a cooling element, and a vacuum port of the applicator, the applicator chamber comprising a bio-barrier on a distal side, wherein the bio-barrier is configured to prevent air and liquid from passing; a tissue acquisition chamber having a tissue acquisition opening defined by a skirt on a distal side of the tissue interface module; and a filter disposed between, and communicating with, the applicator chamber and the tissue acquisition chamber, the filter having openings configured to permit air to pass and to prevent liquid from passing.

In some embodiments, the tissue interface module has a vacuum flow path from the tissue acquisition chamber, through the filter, through the applicator chamber, into the vacuum port of the microwave applicator. The tissue interface module may also include a second filter disposed between, and communicating with, the applicator chamber and the tissue acquisition chamber, the second filter having openings configured to permit air to pass and to prevent liquid from passing. In some such embodiments, the filter and the second filter are positioned on opposing sides of the bio-barrier. In some embodiments, the tissue interface module also has a fluid trap disposed between the tissue acquisition chamber and the filter, the fluid trap configured to capture tissue and liquid.

Another aspect of the invention provides a consumable medical device having: an applicator chamber positioned on a proximal side of said consumable; a tissue chamber positioned on a distal side of said consumable medical device; a first bio-barrier positioned between the applicator chamber and the tissue chamber, the first bio-barrier being: substantially impermeable, flexible and microwave transparent; a vacuum path extending from a distal end of the applicator chamber to a proximal end of the tissue chamber and including a second bio-barrier, a vacuum trap, and an expandable aperture, the vacuum path being adapted to facilitate the flow of air from the tissue chamber, through the expandable aperture, through the vacuum trap, through the second bio-barrier and into the applicator chamber.

In some embodiments, the consumable also includes a shell; an insert positioned in the shell to form a body of said consumable; a gasket positioned on the insert, providing a vacuum seal between the insert and the shell on a distal side of the gasket, being shaped to provide a vacuum seal to an applicator on a proximal side of the gasket and forming a portion of the vacuum trap.

In some embodiments, the consumable also includes a reflector reflecting at least a portion of any microwave energy entering the applicator chamber, the reflector being electrically isolated from an applicator positioned in said applicator chamber, being positioned between the shell and the insert, and having a distal end surrounding at least a portion of the tissue chamber.

In some embodiments, the consumable also has a latch plate positioned in the applicator chamber on said insert, forming a predetermined angle with the first bio-barrier when the first bio-barrier is in a first position.

Still another aspect of the invention provides a method of transmitting energy to a patient for the purpose of reducing sweat, the method including the steps of: transmitting the energy through an applicator having: an antenna; a field spreader, a fluid channel, and a cooling plate; and transmitting the energy through a consumable having: an applicator chamber; a flexible bio-barrier; and a tissue chamber.

Yet another aspect of the invention provides a consumable including a flexible bio-barrier and a cooling plate configured to cooperate to form expandable channel connecting a tissue chamber to an applicator chamber, the consumable including a vacuum path wherein air from a the tissue chamber passes through: the expandable channel; a fluid trap; a second bio-barrier; vacuum channels separating second bio-barrier from an attachment mechanism (such as, e.g., a magnetic plate); and an applicator chamber.

Another aspect of the invention provides a multifunctional connector adapted to connect an applicator to a microwave generator console through a cable assembly, the connector having: a cooling fluid connector; a cooling fluid return connector; a microwave connector; electronic connectors; and vacuum connectors.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:
1. A method of treating a patient comprising:
   positioning a distal end of an applicator in an applicator chamber of a tissue interface module;
   sealing a central opening between the applicator chamber and a tissue acquisition chamber of the tissue interface module against the distal end of the applicator;
   applying a vacuum to the applicator chamber;

placing a distal opening of a tissue acquisition chamber of the tissue interface module against a tissue surface;

pulling a portion of the patient's tissue into the tissue acquisition chamber by creating a vacuum in the tissue acquisition chamber, the vacuum being created by drawing air from the tissue acquisition chamber to a vacuum source in the applicator through a vacuum path comprising the applicator chamber and a filter between the applicator chamber and the tissue acquisition chamber; and applying microwave energy to tissue positioned in the tissue acquisition chamber.

2. The method of claim 1 further comprising cooling the tissue positioned in the acquisition chamber.

3. The method of claim 1 further comprising sealing the applicator chamber against the applicator at a vacuum interface.

4. The method of claim 1 further comprising magnetically attaching the tissue interface module to the applicator.

5. The method of claim 4 wherein the step of magnetically attaching comprises forming a magnetic circuit between elements of the applicator and the tissue interface module.

\* \* \* \* \*